United States Patent
Ray et al.

(10) Patent No.: US 10,683,272 B2
(45) Date of Patent: Jun. 16, 2020

(54) METAL/RADIOMETAL-LABELED PSMA INHIBITORS FOR PSMA-TARGETED IMAGING AND RADIOTHERAPY

(71) Applicants: THE JOHNS HOPKINS UNIVERSITY, Baltimore, MD (US); NORTHWESTERN UNIVERSITY, Evanston, IL (US)

(72) Inventors: Sangeeta Ray, Ellicott City, MD (US); Martin G. Pomper, Baltimore, MD (US); Thomas J. Meade, Evanston, IL (US); Ronnie C. Mease, Fairfax, VA (US); Ying Chen, Timmonium, MD (US); Xing Yang, Baltimore, MD (US); Matthew Rotz, Carlsbad, CA (US)

(73) Assignees: THE JOHNS HOPKINS UNIVERSITY, Baltimore, MD (US); NORTHWESTERN UNIVERSITY, Evanston, IL (US)

( * ) Notice: Subject to any disclaimer, the term of this patent is extended or adjusted under 35 U.S.C. 154(b) by 317 days.

(21) Appl. No.: 15/309,009

(22) PCT Filed: May 6, 2015

(86) PCT No.: PCT/US2015/029504
§ 371 (c)(1),
(2) Date: Nov. 4, 2016

(87) PCT Pub. No.: WO2015/171792
PCT Pub. Date: Nov. 12, 2015

(65) Prior Publication Data
US 2017/0081298 A1 Mar. 23, 2017

Related U.S. Application Data

(60) Provisional application No. 62/117,603, filed on Feb. 18, 2015, provisional application No. 61/989,428, filed on May 6, 2014.

(51) Int. Cl.
| | |
|---|---|
| *A61K 51/00* | (2006.01) |
| *A61M 36/14* | (2006.01) |
| *C07D 257/02* | (2006.01) |
| *A61K 49/10* | (2006.01) |
| *A61K 51/04* | (2006.01) |
| *C07D 403/14* | (2006.01) |
| *A61K 49/12* | (2006.01) |
| *A61K 51/06* | (2006.01) |
| *A61K 49/00* | (2006.01) |

(52) U.S. Cl.
CPC ........ *C07D 257/02* (2013.01); *A61K 49/0002* (2013.01); *A61K 49/106* (2013.01); *A61K 49/12* (2013.01); *A61K 51/0402* (2013.01); *A61K 51/0482* (2013.01); *A61K 51/0497* (2013.01); *A61K 51/06* (2013.01); *C07D 403/14* (2013.01); *A61K 49/108* (2013.01)

(58) Field of Classification Search
None
See application file for complete search history.

(56) References Cited

U.S. PATENT DOCUMENTS 9,776,977 B2 * 10/2017 Pomper ................ C07D 209/14

FOREIGN PATENT DOCUMENTS

| WO | 2009-002529 A2 | 12/2008 |
|---|---|---|
| WO | 2010-108125 A2 | 9/2010 |
| WO | 2013/022797 A1 | 2/2013 |
| WO | 2013082338 | 6/2013 |
| WO | 2014/110372 A1 | 7/2014 |
| WO | 2014110372 | 7/2014 |

OTHER PUBLICATIONS

Banerjee et al., "Preclinical evaluation of 86Y-labeled inhibitors of prostate-specific membrane antigen for dosimetry estimates," J Label Compd Radiopharm. 2011; 54:S65.
European Patent Office Supplementary Search Report for Application No. 15790006.9 dated Nov. 21, 2017, 15 pages.
European Patent Office Extended Search Report for Application No. 15790006.9 dated Mar. 12, 2018 (18 pages).
De Leon-Rodriguez et al., "MRI detection of VEGFR2 in vivo using a low molecular weight peptoid-(Gd)8-dendron for targeting," Journal of the American Chemical Society, 2010, 132(37):12829-12831.
Wu et al., "Synthesis and Evaluation of a Peptide Targeted Small Molecular Gd-DOTA Monoamide Conjugate for MR Molecular Imaging of Prostate Cancer," Bioconjugate Chemistry, 2012, 23(8):1548-1556.
International Search Report and Written Opinion dated Aug. 3, 2015, from related PCT Patent Application No. PCT/US2015/029504.
Zhuxian Zhou et al., "Gadolinium-based contrast agents for MR cancer imaging", Wiley Interdisciplinary Reviews Nanomedine and Nanobiotechnolology, vol. 5, No. 1, pp. 1-18 (Jan. 2013).
Graeme J. Stasiuk et al., "The ubiquitous DOTA and its derivatives: the impact of 1,4,7,10-tetraazacyclododecane-1,4,7,10-tetraacetic acid on biomedical imaging". Chemical Communications, vol. 49, pp. 2732-2746 (Jan. 30, 2013: On-line).
Sachin S. Chandran et al., "Characterization of a targeted nanoparticle functionalized with a urea-based inhibitor of prostate-specific membrane antigen (PSMA)" Cancer Biology & Therapy, vol. 7, No. 6, pp. 974-982 (Jul. 1, 2008: On-line).

(Continued)

*Primary Examiner* — Michael G. Hartley
*Assistant Examiner* — Melissa J Perreira
(74) *Attorney, Agent, or Firm* — Casimir Jones, S.C.; Jeffrey W. Childers

(57) ABSTRACT

Low-molecular weight gadolinium (Gd)-based MR contrast agents for PSMA-specific Ti-weighted MR imaging are disclosed. The (Gd)-based MR contrast agents exhibit high binding affinity for PSMA and exhibit specific Ti contrast enhancement at PSMA+ cells. The PSMA-targeted Gd-based MR contrast agents can be used for PSMA-targeted imaging in vivo. 86Y-labeled PSMA-binding ureas also are provided, wherein the PSMA-binding ureas also are suitable for use with other radiotherapeutics.

20 Claims, 35 Drawing Sheets

(56) References Cited

OTHER PUBLICATIONS

Ying Chen et al., "Radiohalogenated prostate-specific membrane antigen (PSMA)-based ureas as imaging agents for prostate cancer", Journal of Medicinal Chemistry, vol. 51, Issue 24, pp. 7933-7943 (Dec. 25, 2008).
Sangeeta R. Banerjee et al., Synthesis and evaluation of technetium-99m-and rhenium-labeled inhibitors of the prostate-specific membrane antigen (PSMA), Journal of Medicinal Chemistry, vol. 51, Issue 15, pp. 4504-4517 (Aug. 14, 2008).
Banerjee et al., $^{64}$Cu-labeled inhibitors of prostate-specific membrane antigen for PET imaging of prostate cancer. J Med Chem. Mar. 27, 2014;57(6):2657-69.
Extended European Search Report for EP16169083.3 dated Aug. 9, 2019, 12 pages.

* cited by examiner

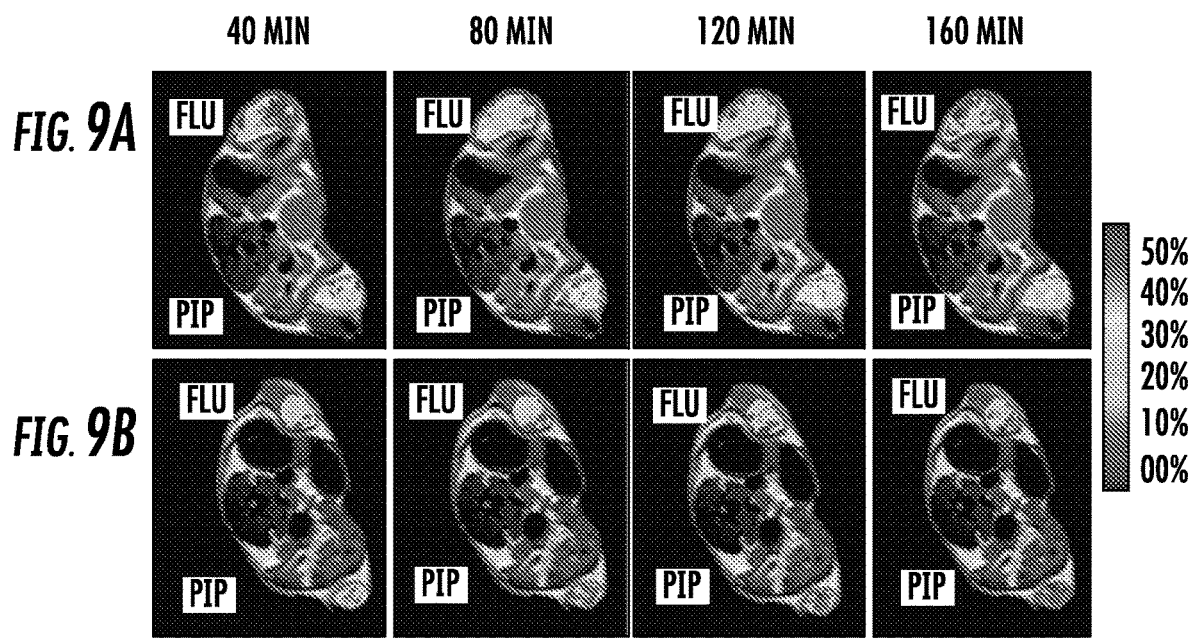

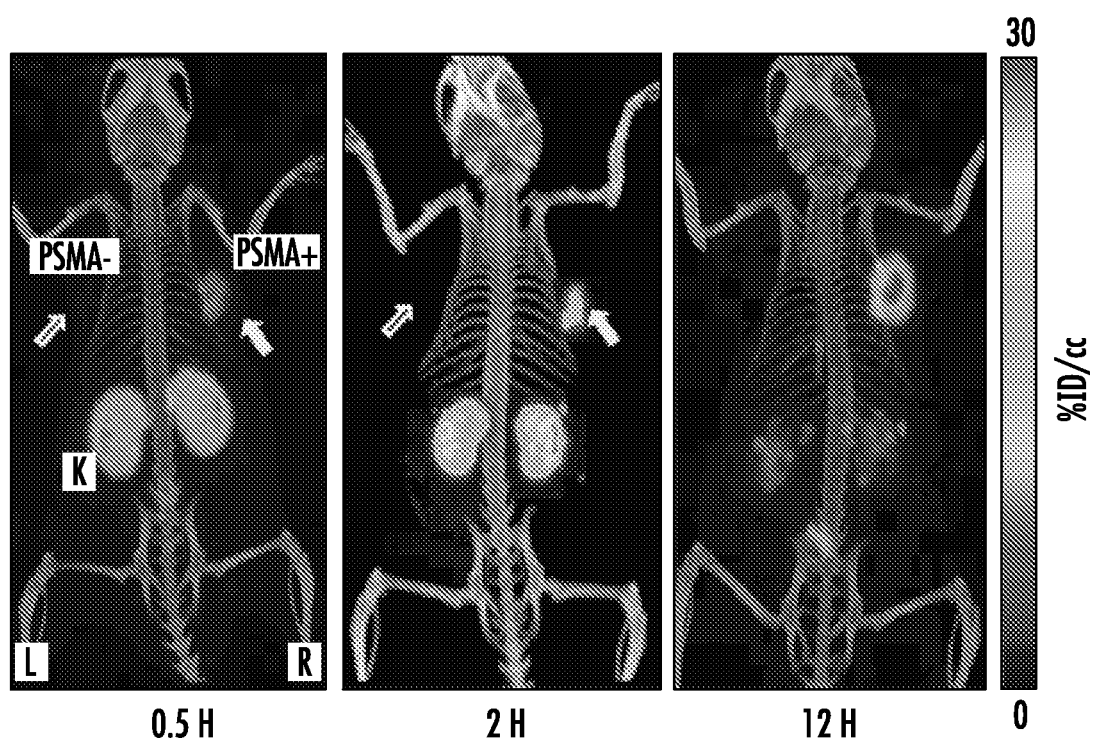
FIG. 20A  0.5 H
FIG. 20B  2 H
FIG. 20C  12 H

60 MIN

120 MIN

240 MIN

METAL/RADIOMETAL-LABELED PSMA INHIBITORS FOR PSMA-TARGETED IMAGING AND RADIOTHERAPY

CROSS-REFERENCE TO RELATED APPLICATIONS

This application is a 35 U.S.C. § 371 National Stage Entry of International Application No. PCT/US2015/029504 having an international filing date of May 6, 2015, which claims the benefit of U.S. Provisional Application Nos. 61/989,428, filed May 6, 2014, and 62/117,603, filed Feb. 18, 2015, each of which are incorporated herein by reference in their entirety.

FEDERALLY SPONSORED RESEARCH OR DEVELOPMENT

This invention was made with government support under K25CA148901-01A1 and U54CA1346751 awarded by the National Institutes of Health (NIH). The government has certain rights in the invention.

BACKGROUND

The prostate-specific membrane antigen (PSMA) is increasingly recognized as a viable target for imaging and therapy of prostate and other forms of cancer (Ghosh and Heston, 2004; Milowsky et al., 2007; Olson et al., 2007). PSMA is significantly over-expressed in PCa and metastases, particularly with respect to the hormone-refractory form (Ghosh and Heston, 2004; Milowsky et al., 2007). PSMA also is known to express by most solid tumors and tumor neovasculature (Haffner et al., 2012; Haffner et al., 2009). Imaging PSMA can provide insight into androgene signaling (Evans et al., 2011) and response to taxane therapy (Hillier et al., 2011). Previous studies have demonstrated PSMA-targeted radionuclide imaging in experimental models of prostate cancer (Schulke et al., 2003; Mease et al., 2013; Banerjee et al., 2010) and in the clinic (Cho et al., 2012; Kulkarni et al., 2014; Zechmann et al., 2014) using functionalized cysteine-glutamate or lysine-glutamate ureas. For the attachment of large molecular fragments, such as radiometal ($^{99m}$Tc, $^{68}$Ga, $^{111}$In, $^{86}$Y, $^{203}$Pb, $^{64}$Cu) complexes (Banerjee, Pullambhatla, Shallal, et al., 2011; Banerjee, Pullambhatla, Byun, et al., 2011; Banerjee et al., 2008) and nanoparticles (Chandran et al., 2008; Kam et al., 2012), a long linker was placed between the large molecule and the targeting urea to retain PSMA-targeted binding. Without wishing to be bound to any one particular theory, it was thought that PSMA would be a suitable biomarker for MR molecular imaging because of the extra-cellular location of the ligand binding site and the estimated high receptor concentration per cell (~3.2 μM/cell volume).

MR imaging is a clinically relevant, noninvasive diagnostic tool for providing high resolution anatomic and functional imaging. Molecular MR imaging enables the visualization of biological markers in vivo (Artemov, Mori, Okollie et al., 2003; Artemov, Mori, Ravi, Bhujwalla, et al., 2003; Konda et al., 2001; Lanza et al., 2004; Huang, et al., 2013). Gd(III)-based contrast agents are widely accepted by clinicians because they are easy to administer and provide $T_1$-weighted, positive contrast. Although progress has been made in the design of contrast agents with high relaxivity, sensitivity remains a limiting factor for molecular MR imaging. For use in molecular imaging applications (specifically, for imaging receptors or protein expression), Gd(III)-based contrast agents seldom exceed the limit of detection (Artemov, Mori, Okollie et al., 2003; Artemov, Mori, Ravi, Bhujwalla, et al., 2003; Konda et al., 2001; Lanza et al., 2004; Huang, et al., 2013). With signal amplification strategies, MR might offer a sensitive modality for molecular imaging complementary to radionuclide-based techniques (Aime et al., 2004; Major et al., 2009; Song et al., 2008; Artemov, 2003). Although amplification strategies could improve the sensitivity of a targeted agent, shifting from a simple, low-molecular-weight compound to a larger, multiplexed entity may significantly alter the pharmacokinetic profile of the agent (Artemov, Mori, Okollie et al., 2003; Artemov, Mori, Ravi, Bhujwalla, et al., 2003; Konda et al., 2001; Lanza et al., 2004; Huang, et al., 2013). Sherry et al. have addressed the issue of sensitivity by generating contrast agents with very high binding affinities ($K_d$) such that the amount of agent needed for detection by MR could be minimized (Hanaoka et al., 2008; De Leon-Rodriguez et al., 2010). Combining a receptor-specific high affinity ligand together with multimeric Gd(III) agents for detection has been devised as one solution for enabling MR-based receptor imaging (Wu et al. 2012).

An example of that approach includes molecular imaging of VEGFR2 by preparing a multimeric Gd-dendron with high longitudinal relaxivity ($r_1$) values (De Leon-Rodriguez et al., 2010). Other multimeric agents have been reported with improved $r_1$ values at higher field strengths since MR imaging, both experimental and clinical, are moving to higher fields (Mastarone 2011). Optimizing relaxivity at high field provides the advantages of greater signal-to-noise and contrast to noise ratios (SNR/CNR) and the attendant benefits of higher spatial resolution and reduced acquisition times (Rooney 2007). Combination of these concepts, namely use of high-affinity targeting moieties with sensitive multimeric contrast agents, provides rationale to investigate targeted MR imaging of cells and tissues expressing the prostate-specific membrane antigen (PSMA).

Further, it has been reasoned that urea-based agents could also be used for radiotherapy of PSMA-containing lesions using radionuclides. In fact, clinical studies using that approach with [$^{131}$I]MIP1095 ((S)-2-(3-((S)-1-carboxy-5-(3-(4-[$^{131}$I]iodophenyl)ureido)pentyl)ureido)pentanedioicacid) (Zechmann et al., 2014) and $^{177}$Lu-labeled PSMA-targeted agents (Kulkarni et al., 2014) are under way for the treatment of castrate-resistant prostate cancer. This will be in analogy with radioimmunotherapy (RIT), which has proved remarkably successful in the treatment of lymphoma with two commercial products routinely integrated into clinical practice. However, RIT is fraught with difficulties due to the use of radiolabeled antibodies for imaging, including prolonged circulation times, unpredictable biological effects and the occasional need for pre-targeting strategies. Furthermore, antibodies may have less access to tumor than low molecular weight agents, which can be manipulated pharmacologically. Therefore a need remains for low molecular weight compounds with high binding affinity to PSMA for the imaging and radiotherapy of tumors.

The positron-emitting radionuclide $^{86}$Y (half-life [$t_{1/2}$]=14.74 h, $\beta^+$=33%, $E_{\beta+}$=664 keV) is an attractive isotope for molecular imaging (Nayak and Brechbiel, 2011). Yttrium-86 can readily be prepared on a small biomedical cyclotron employing the $^{86}$Sr(p, n)$^{86}$Y nuclear reaction (Yoo et al., 2005). The extensive use of the high-energy $\beta^-$-emitter $^{90}$Y ($t_{1/2}$=64.06 h, $\beta^-$=72%, $E_{\beta-}$=2.288 MeV) for endoradiotherapy (Witzig et al., 2003; Bodei et al., 2004) makes $^{86}$Y ideal for dosimetry estimates of $^{90}$Y-labeled radiotherapeutics (Helisch et al., 2004). Antibodies and peptides radiolabeled with [86]Y have identical properties to those labeled with $^{90}$Y, enabling accurate absorbed dose estimates for $^{90}$Y for radiotherapeutics (Nayak and Brechbiel, 2011; Palm et al., 2003). Although $^{177}$Lu has a shorter β-particle range ($t_{1/2}$=6.7 days, $E_{β-}$=0.5 MeV) than $^{90}$Y, is because they have similar chelation chemistry, [86]Y proposed as a suitable imaging surrogate to investigate potential $^{177}$Lu-based radiotherapeutics, as well as those radiolabeled with [90]Y. A similar rationale has been applied to agents for neuroendocrine-targeted peptide receptor radionuclide therapy (Chen et al., 2012). Using similar approach, a potential matched-pair imaging radioisotope [203]Pb (half-life, 51.9 h, $E_{β-}$=279-keV γ-ray, 81%) suitable for SPECT imaging can be used for therapeutic radionuclide [212]Pb for α-particle therapy (Chappell, et al. 2000; Yong, et al. 2011; Yong, et al. 2012; Yong, et al. 2013). The decay scheme of [212]Pb includes [212]Bi, which yields an α-particle, two β-particles, and several γ-emissions upon decay. α-Particle emitters are particularly attractive for targeted radiotherapy due to high linear energy transfer properties such as localized dense ionization, which results in irreparable DNA double-strand breaks and cytotoxicity that is independent of tissue oxygen content or dose rate (McDevitt, et al., 1998). [212]Pb and [212]Bi are both promising α-particle emitting sources that have well-described radiochemistry for antibody linkage and are readily obtained from a [224]Ra generator.

Radiohalogenated carbamate based PSMA inhibitors that also demonstrated high binding affinity to PSMA in-vitro also have been developed and when radiolabeled with the positron emitter F-18 showed high uptake in PSMA positive mouse tumor xenografts with fast clearance from normal tissues. Because of the favorable pharmacokinetic profile of this class of compounds, i.e., low nonspecific binding, lack of metabolism in vivo and reasonable tumor residence times, the imaging studies have been extended to molecular radiotherapy. Moreover, carbamate-based inhibitor can be coupled to metal-chelating agent employing a linker functionality similar as urea-based metal/radiometal-based agents to maintain high binding affinity for PSMA. Consequently, metal or radiometal comjugated carbamate scaffold can also be utilized for imaging and therapy of PSMA-expressing cells and tissues.

SUMMARY

In some aspects, the presently disclosed subject matter provides compounds of Formula (I):

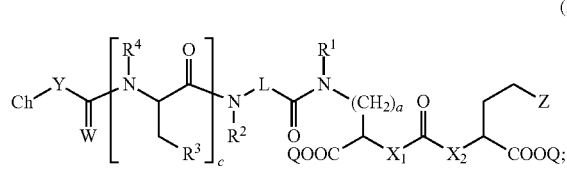

wherein: Z is tetrazole or $CO_2Q$; Q is H or a protecting group; $X_1$ and $X_2$ are each independently NH or O; a is an integer selected from the group consisting of 1, 2, 3 and 4; c is an integer selected from the group consisting of 0, 1, 2, 3 and 4; each $R^1$, $R^2$ and $R^4$ is independently H or $C_1$-$C_4$ alkyl; each $R^3$ is independently H, $C_1$-$C_6$ alkyl or $C_2$-$C_{12}$ aryl; W is independently O or S; Y is —NH— and can be present or absent; L is a linker, wherein the linker is selected from the group consisting of:

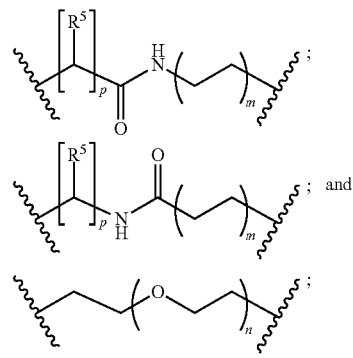

wherein: m is an integer selected from the group consisting of 1, 2, 3, 4, 5, 6, 7 and 8; each $R^5$ is independently H or —$COOR^6$ wherein each $R^6$ is independently H or a $C_1$-$C_6$ alkyl; n is an integer selected from the group consisting of 1, 2, 3, 4, 5, 6, 7, 8, 9, 10, 11 and 12; p is an integer selected from the group consisting of 1, 2, 3, 4, 5, 6, 7 and 8; Ch is a chelating moiety that can comprise one or more metals or radiometals; or a pharmaceutically acceptable salt thereof.

In other aspects, the presently disclosed subject matter provides a method for imaging or treating one or more prostate-specific membrane antigen (PSMA) tumors or cells, the method comprising contacting the one or more tumors or cells with an effective amount of a compound of formula (I) and making an image.

Certain aspects of the presently disclosed subject matter having been stated hereinabove, which are addressed in whole or in part by the presently disclosed subject matter, other aspects will become evident as the description proceeds when taken in connection with the accompanying Examples and Figures as best described herein below.

BRIEF DESCRIPTION OF THE FIGURES

Figure 1A:
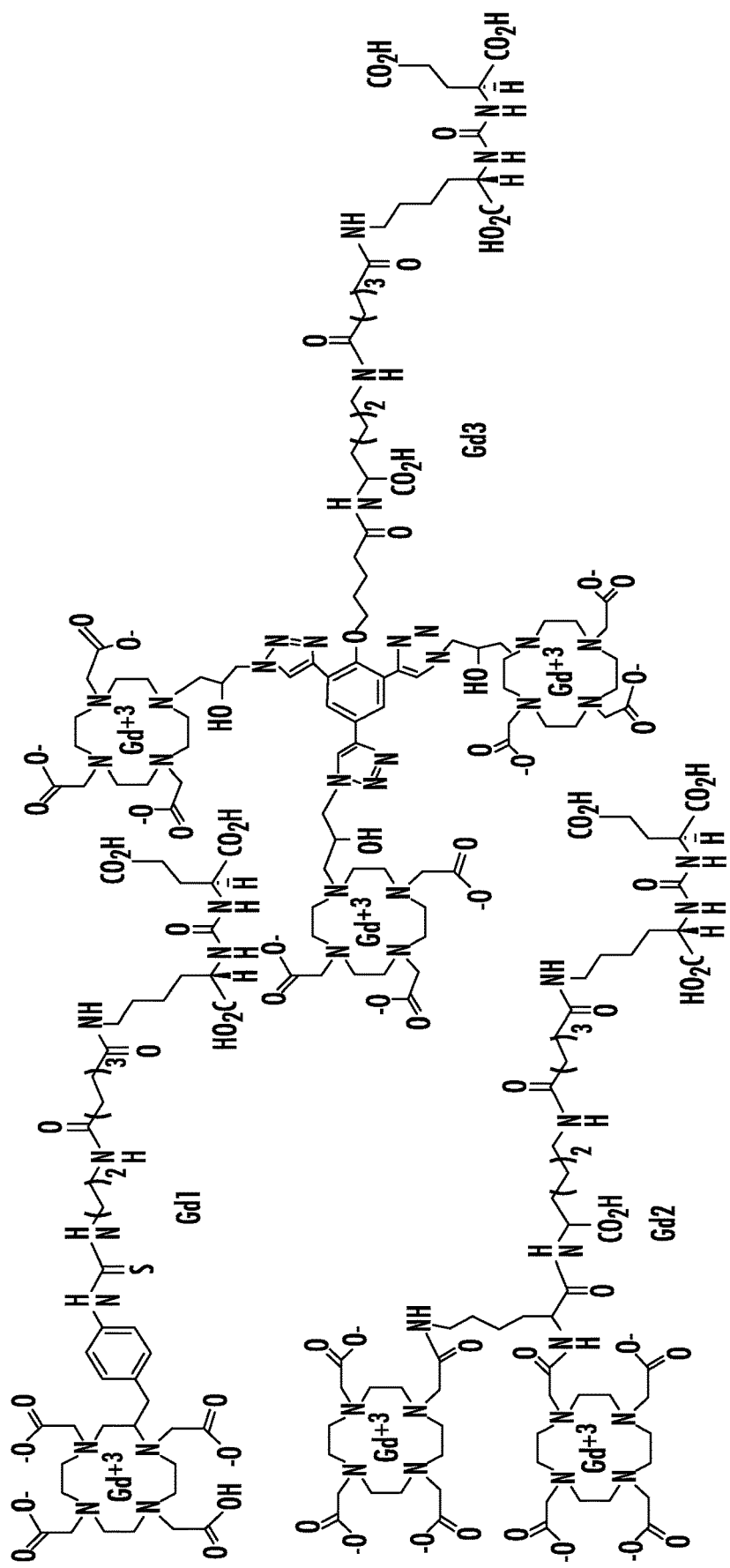
Figure 1B:
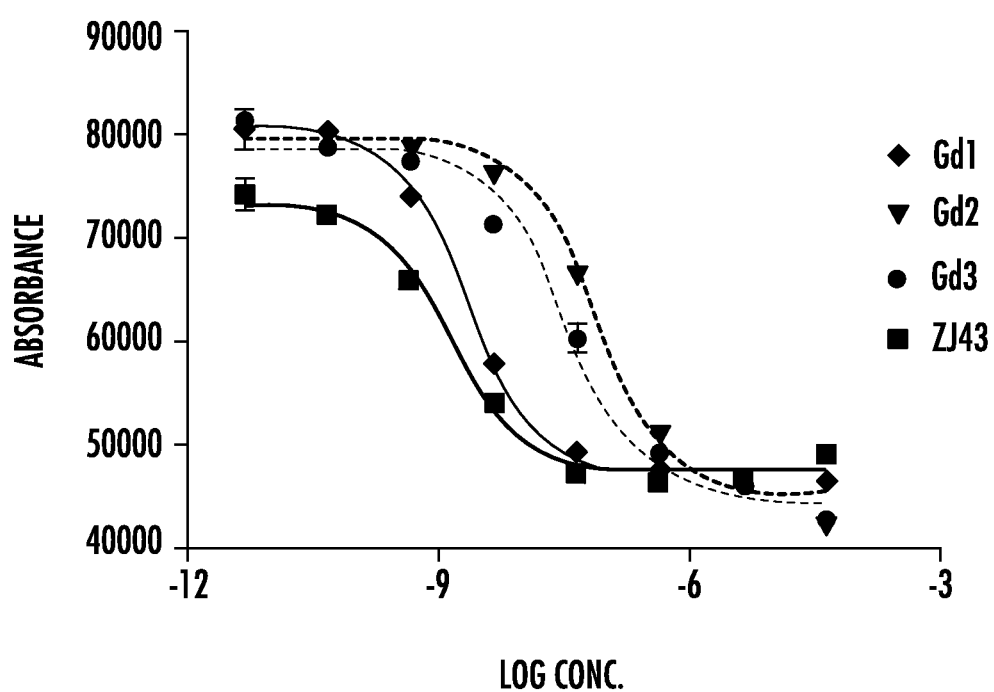
Figure 2:
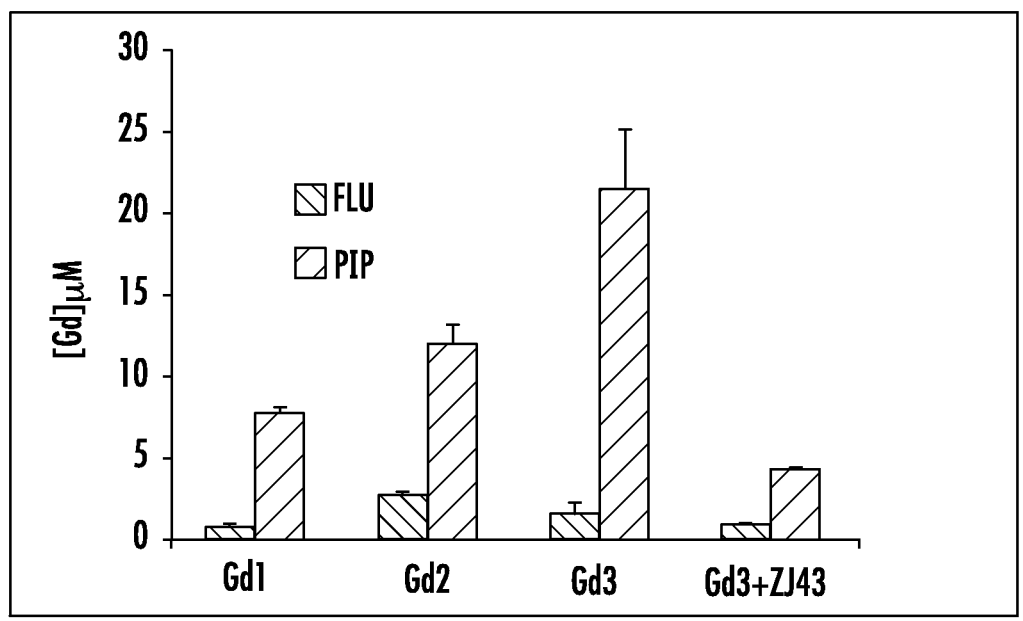
Figure 3:
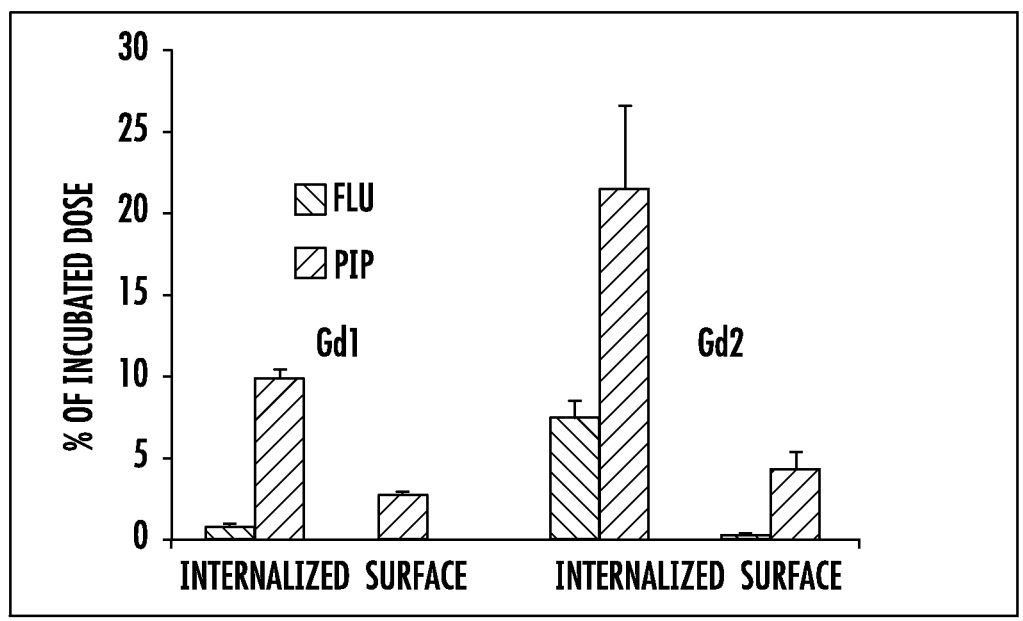
Figure 4A:
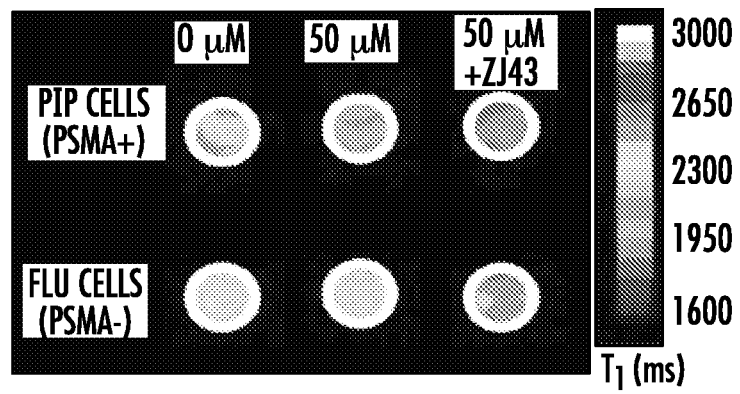
Figure 4B:
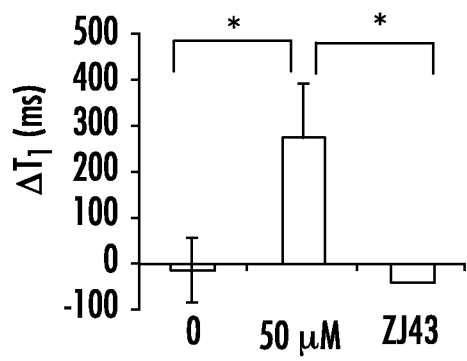
Figure 4C:
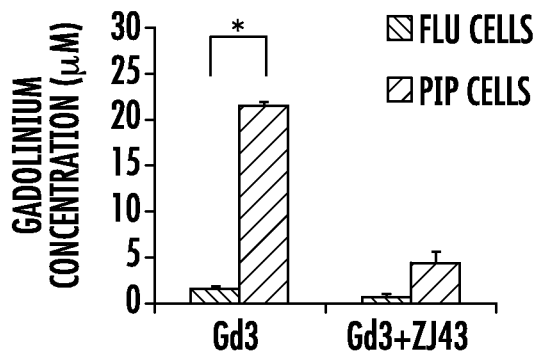
Figure 6A:
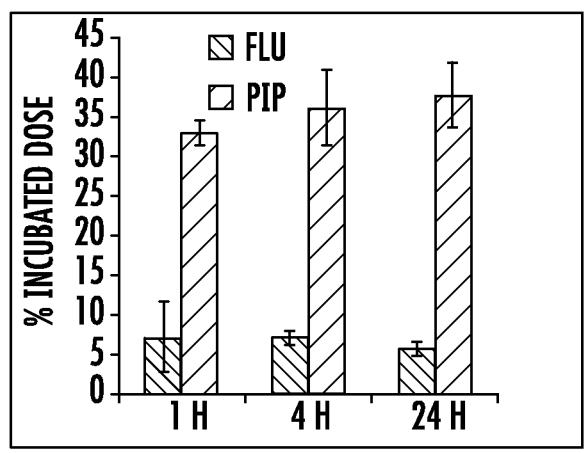
Figure 6B:
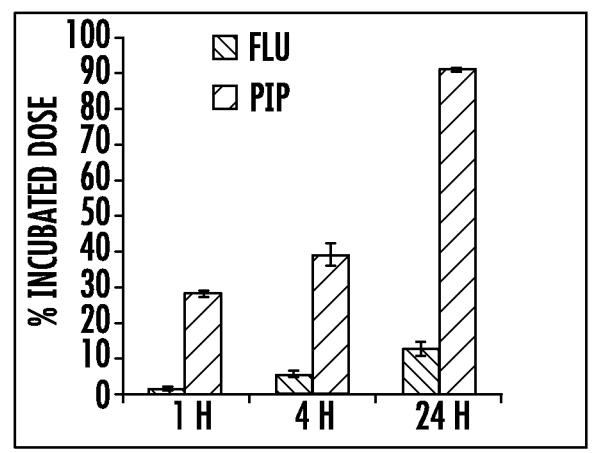
Figure 7:
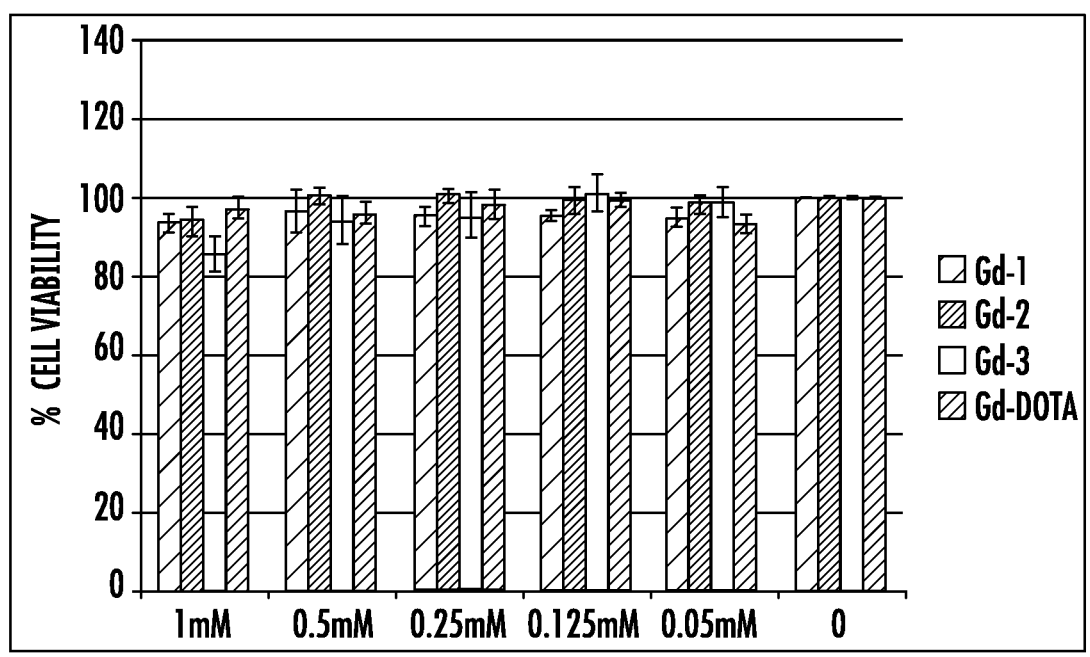
Figure 8:
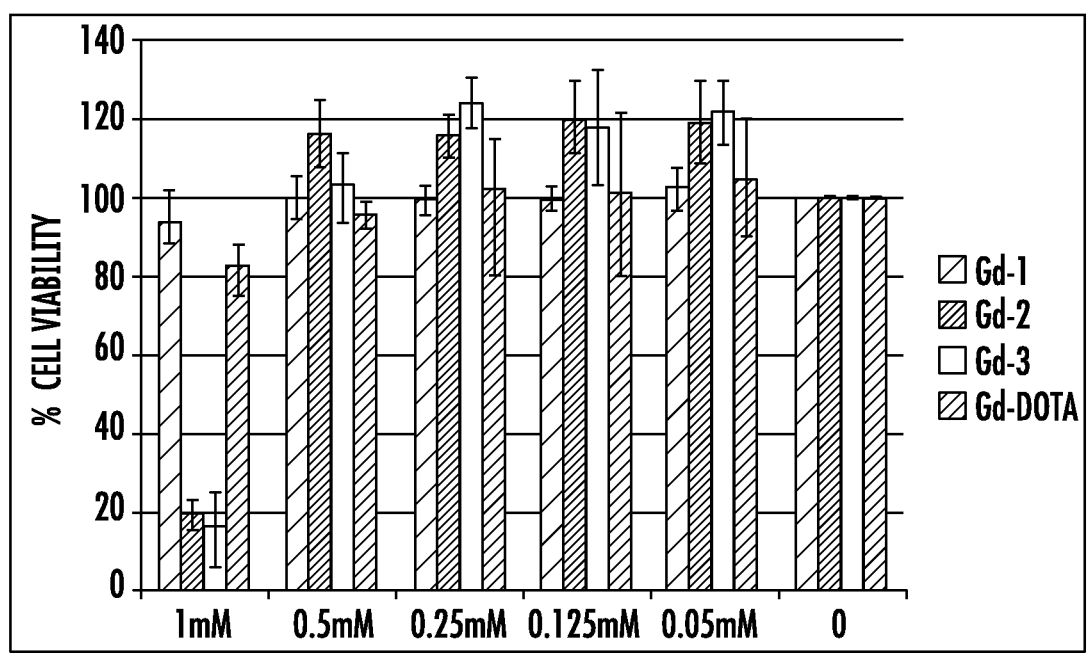
Figure 10A:
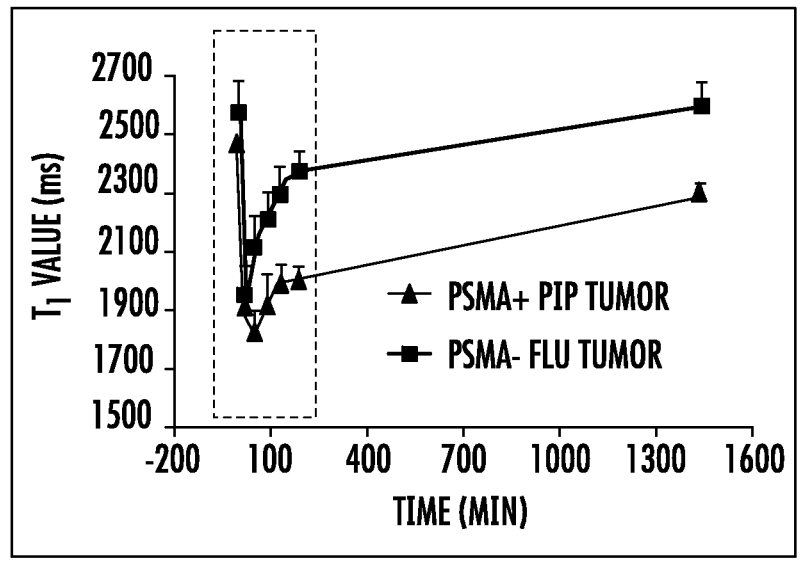
Figure 10B:
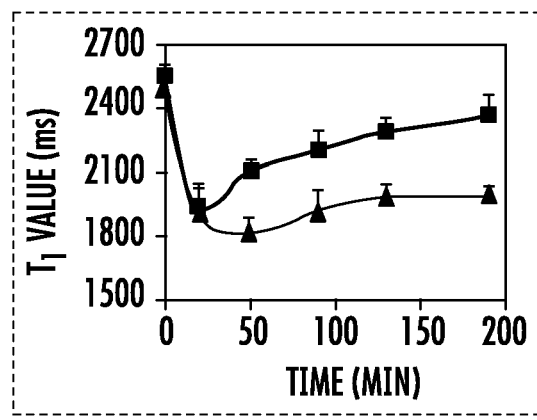
Figure 11:
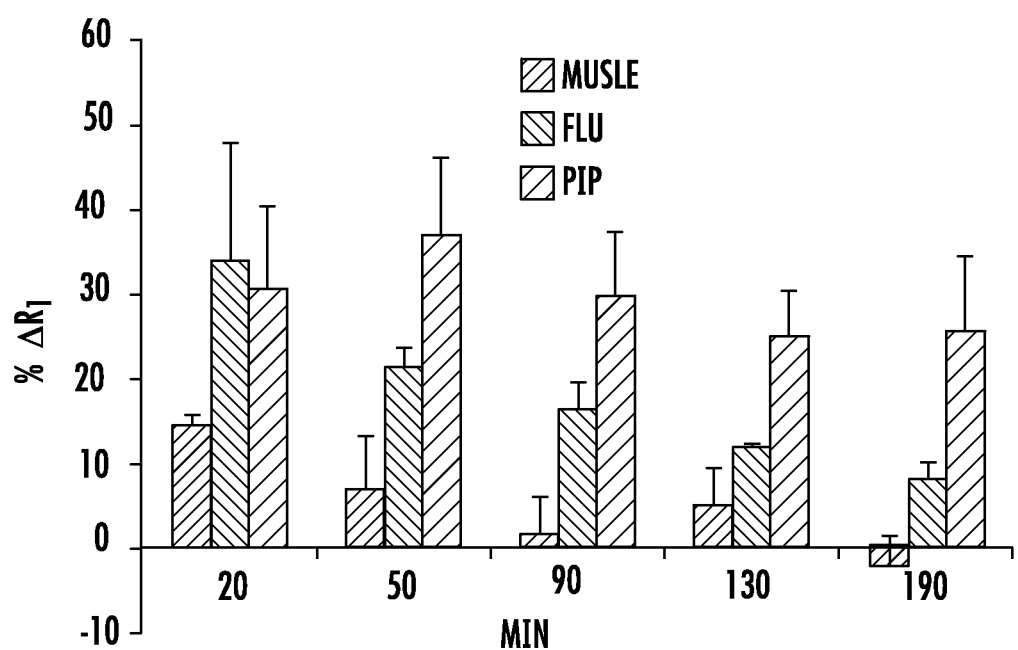
Figure 12:
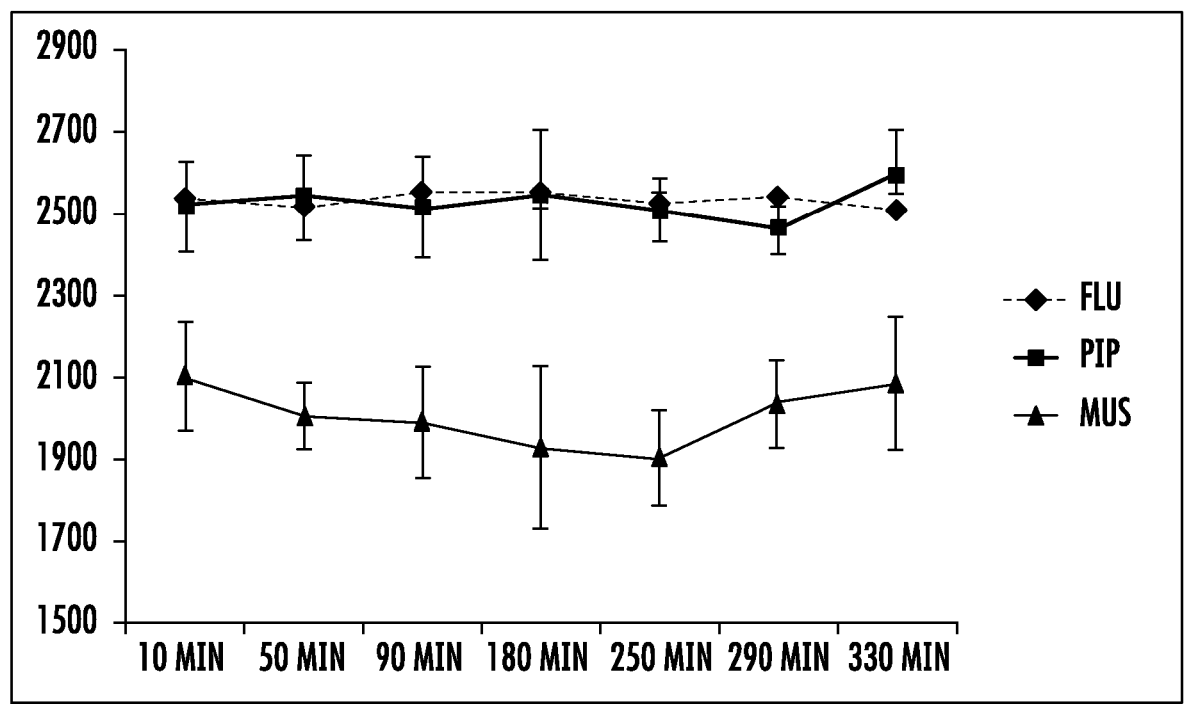
Figure 13A:
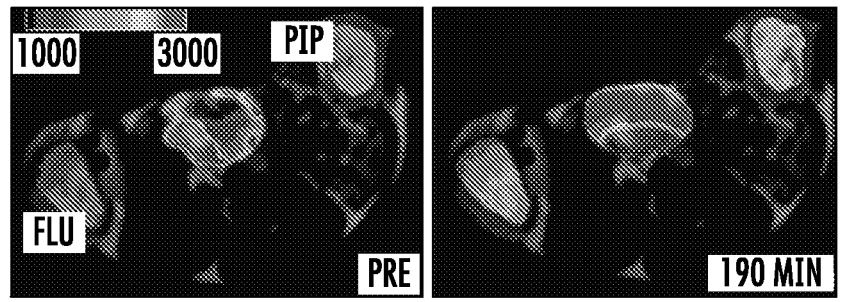
Figure 13B:
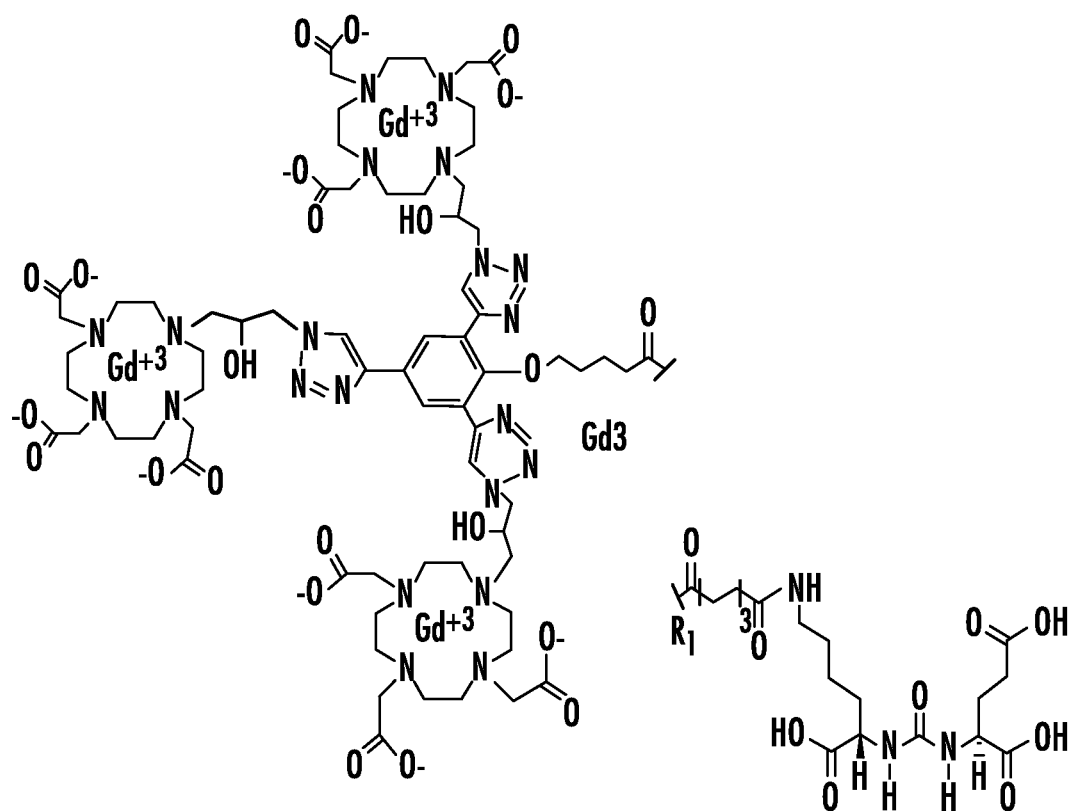
Figure 14:
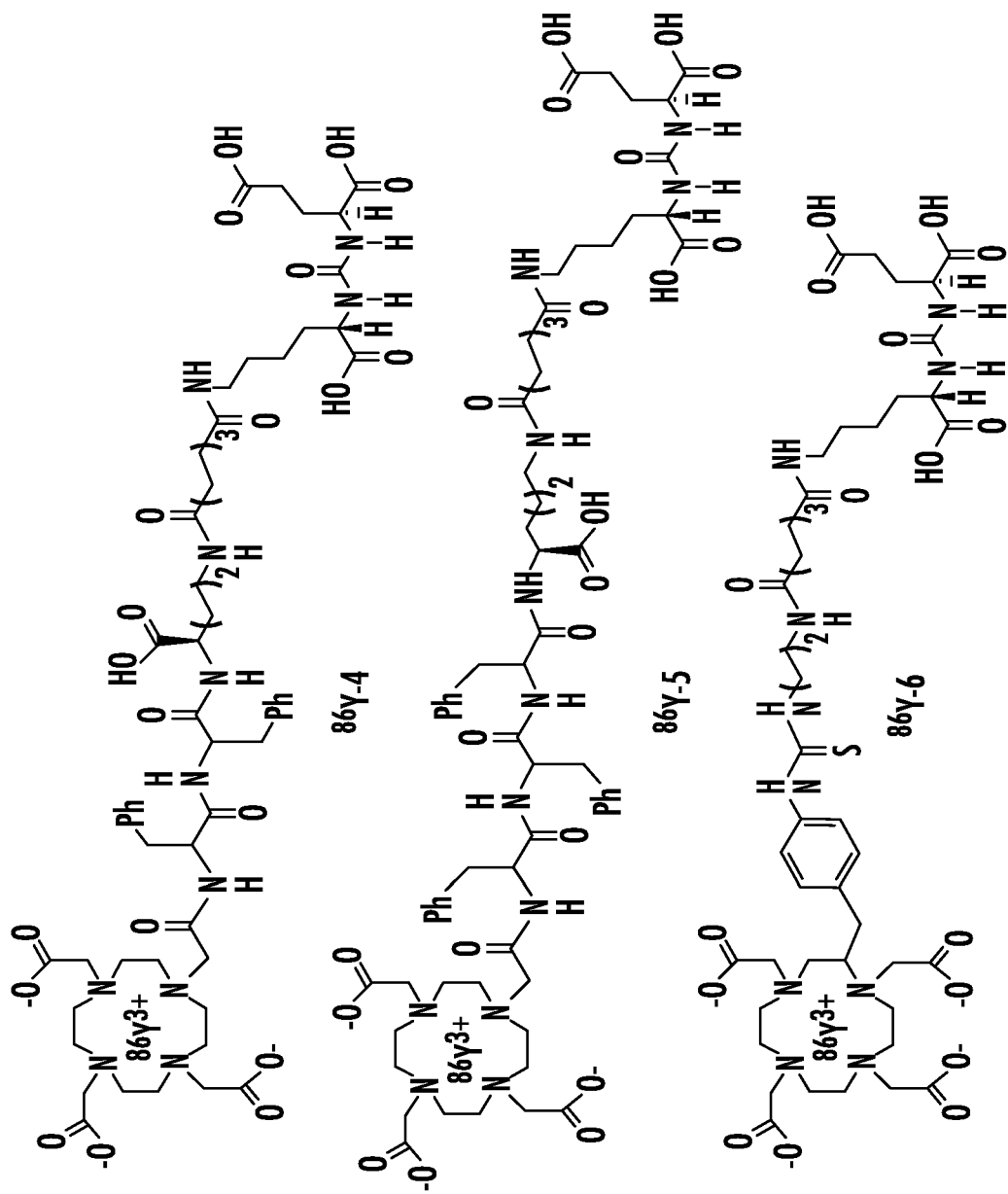
Figure 15A:
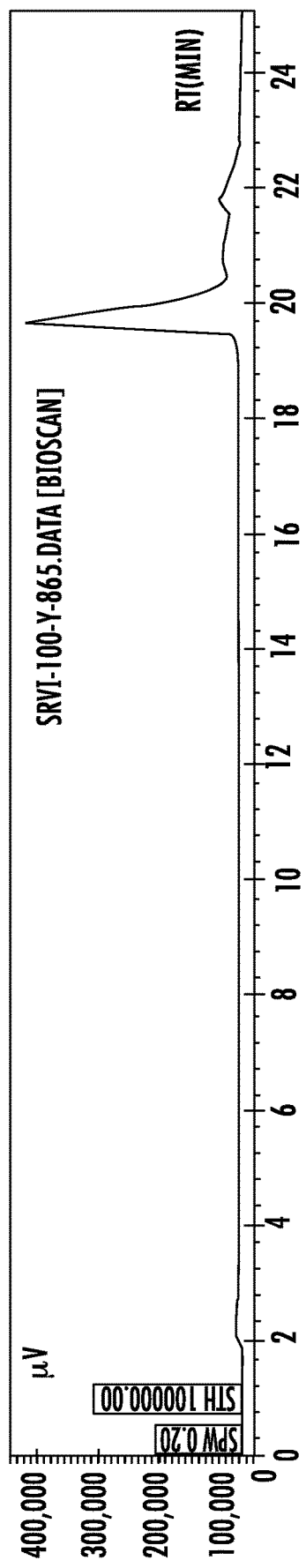
Figure 15B:
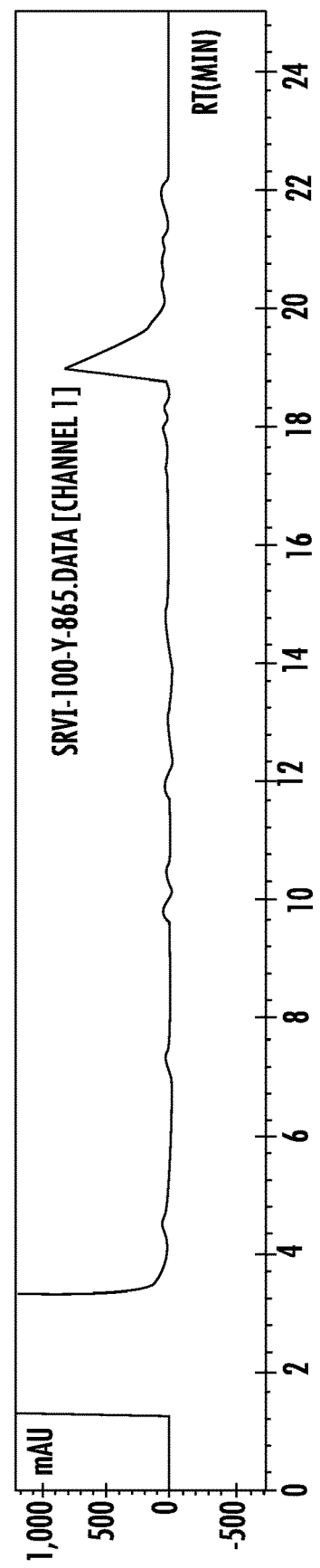
Figure 16A:
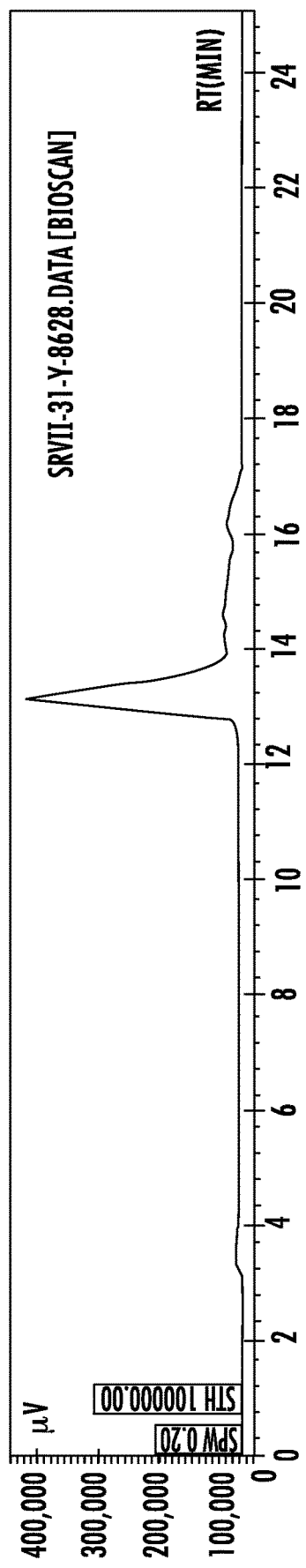
Figure 16B:
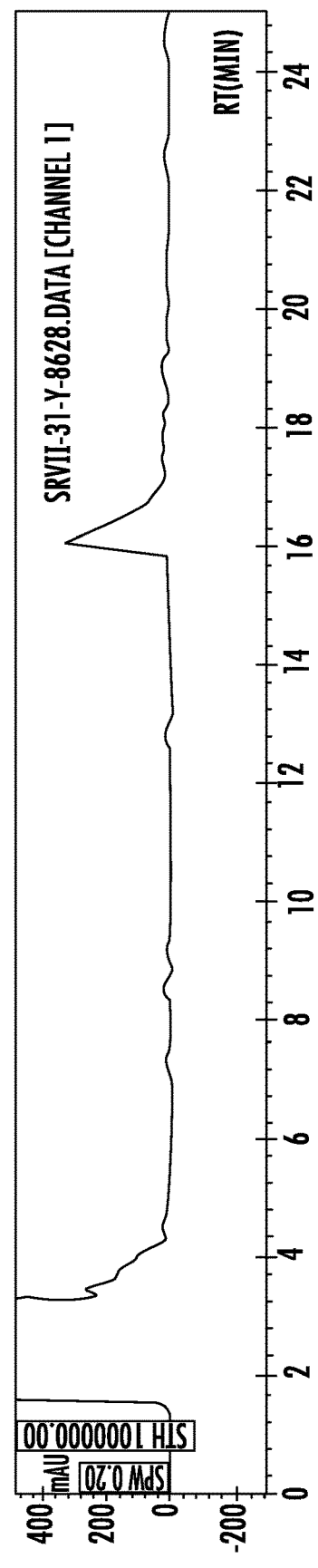
Figure 17A:
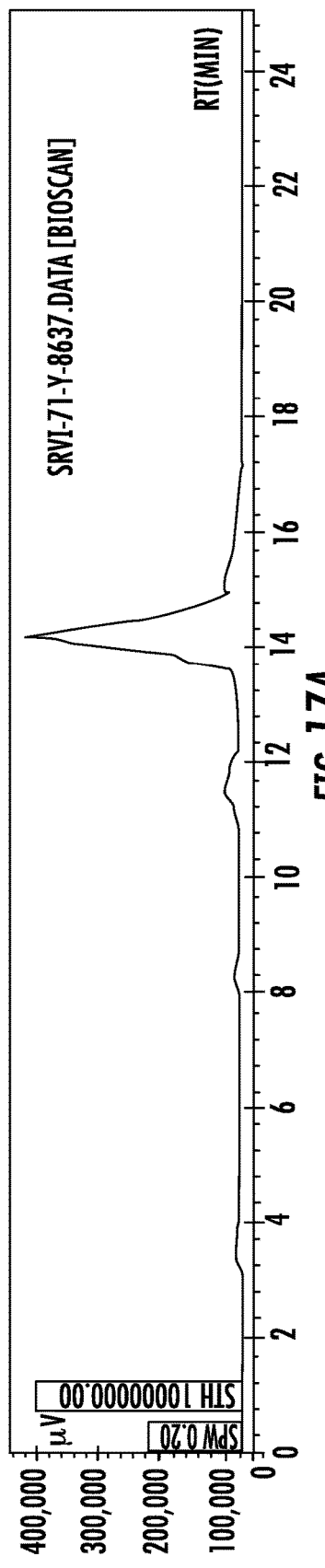
Figure 17B:
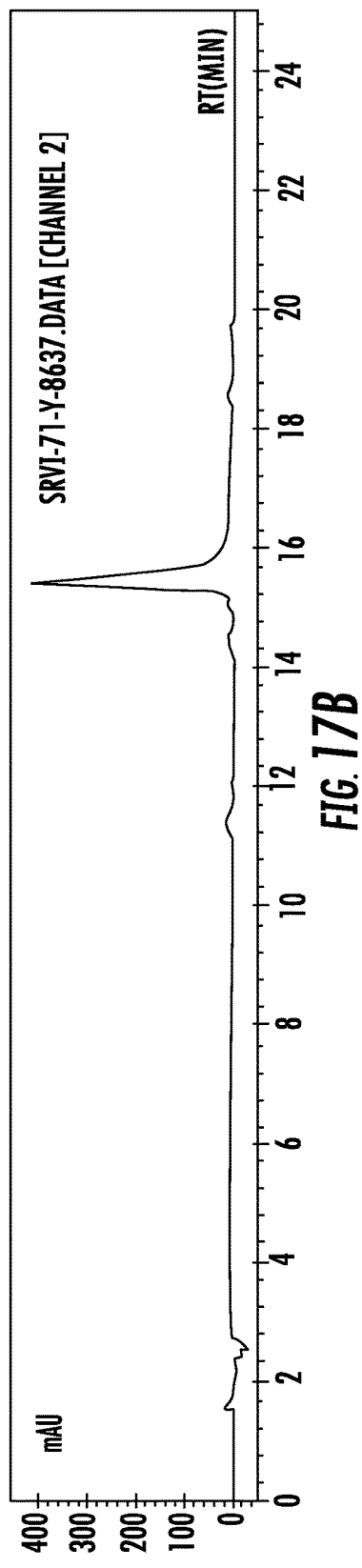
Figure 17C:
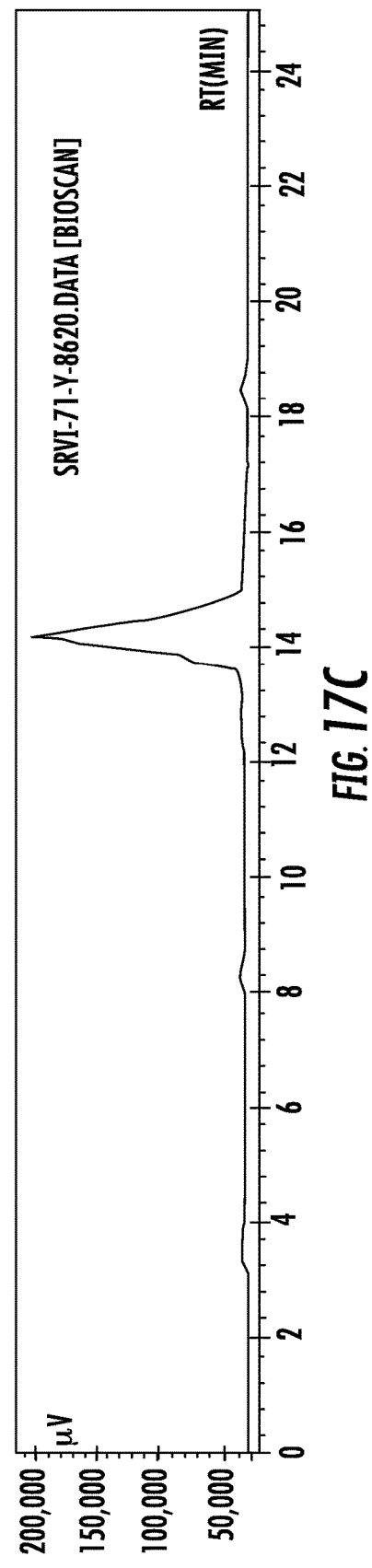
Figures 18A, 18B, 18C:
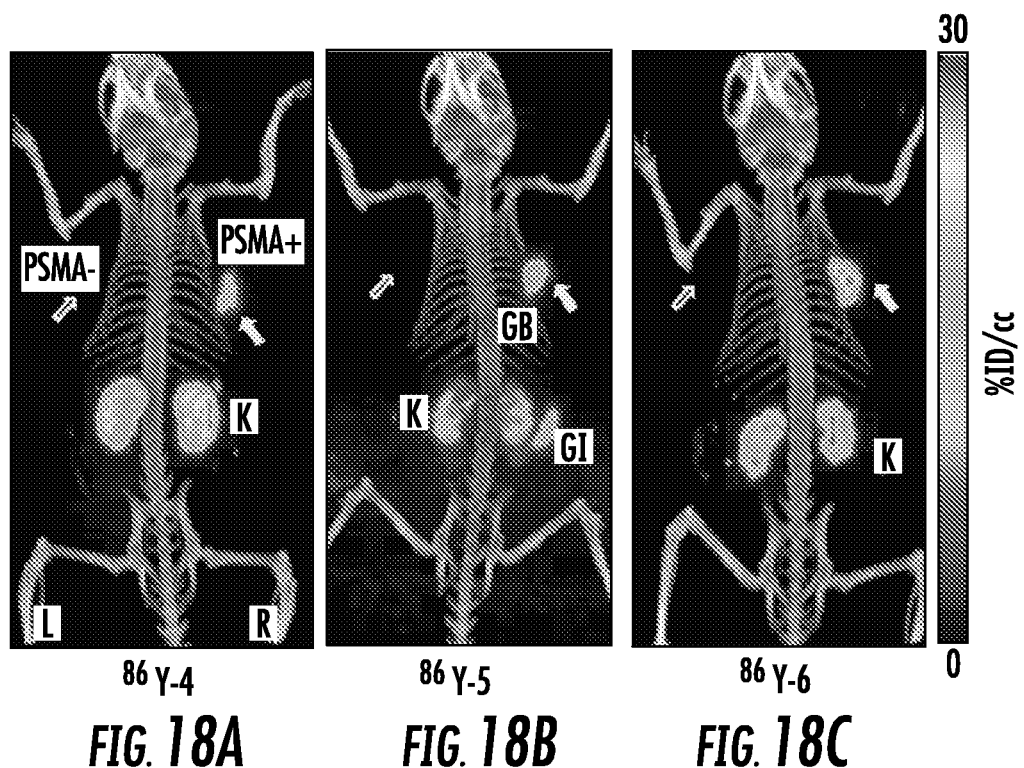
Figures 19A, 19B:
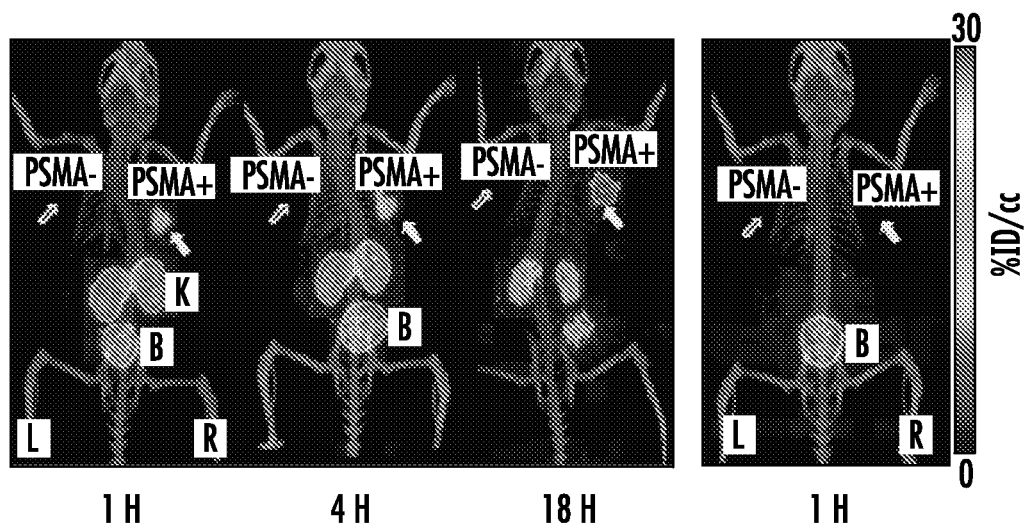
Figure 19C:
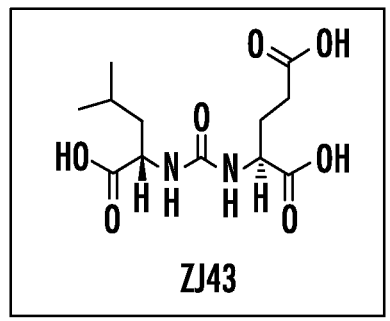
Figures 21A, 21B:
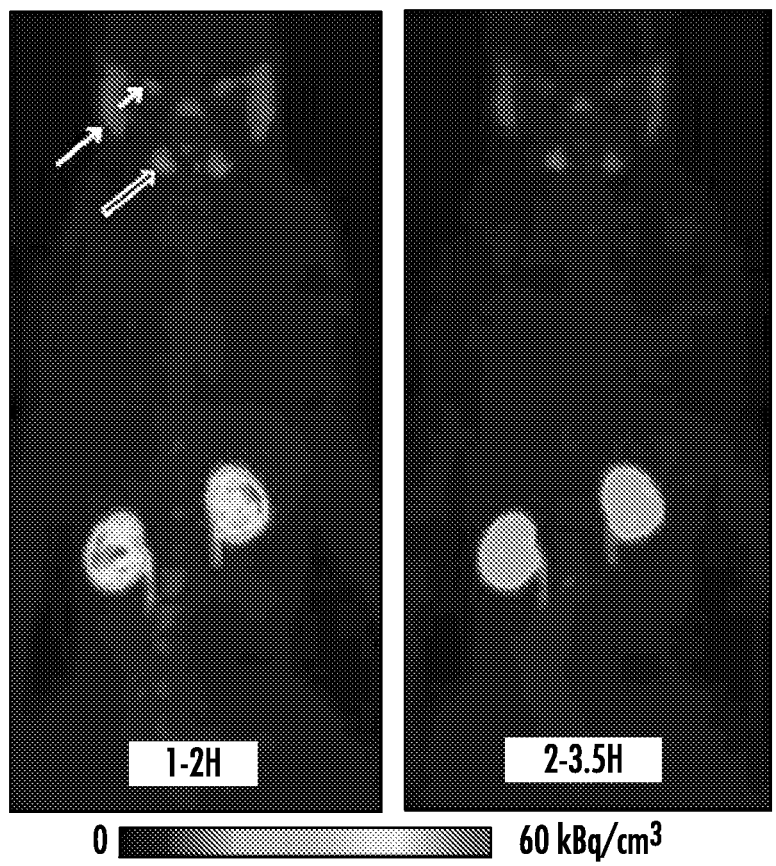
Figure 22:
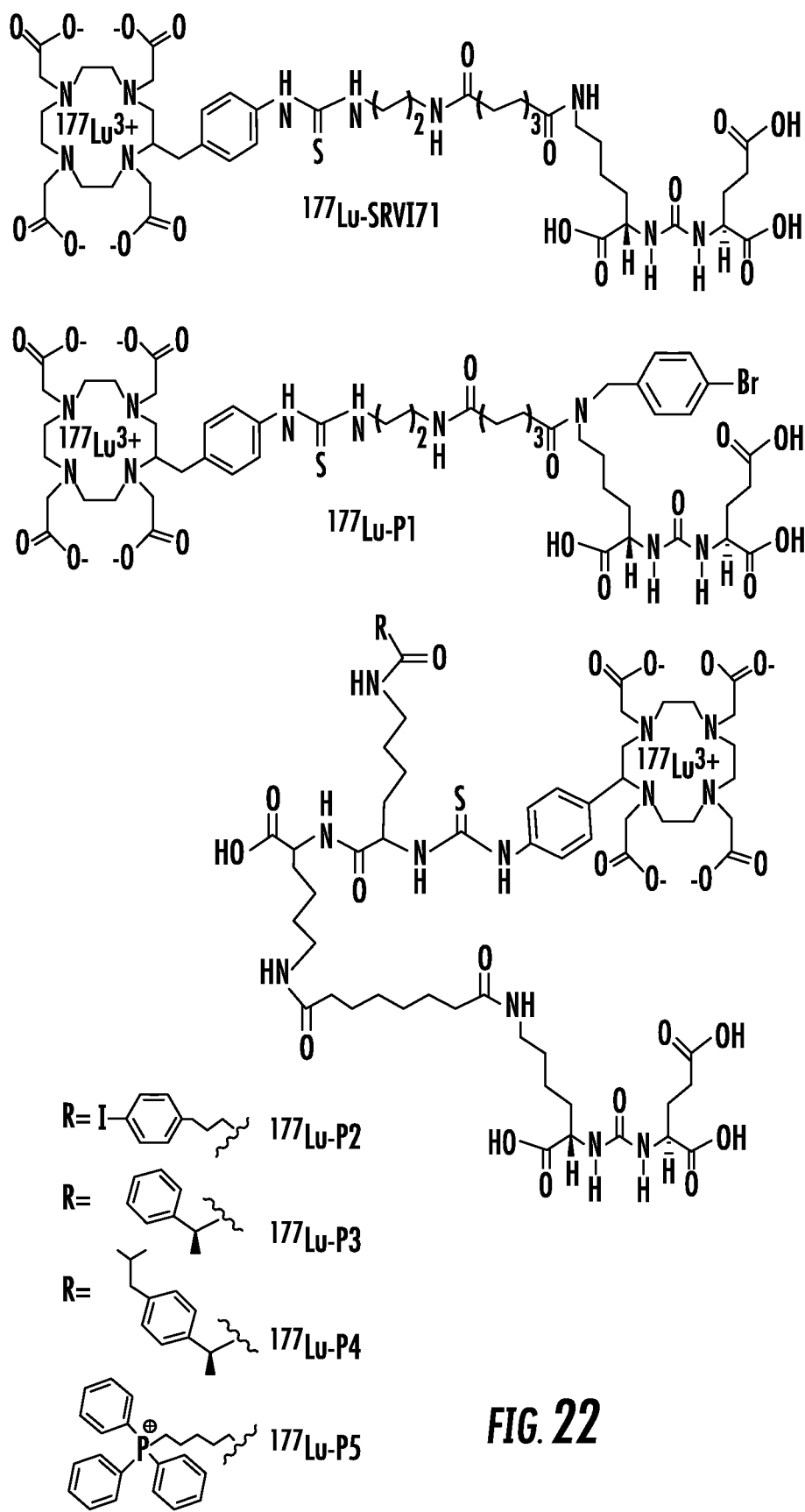
Figure 23:
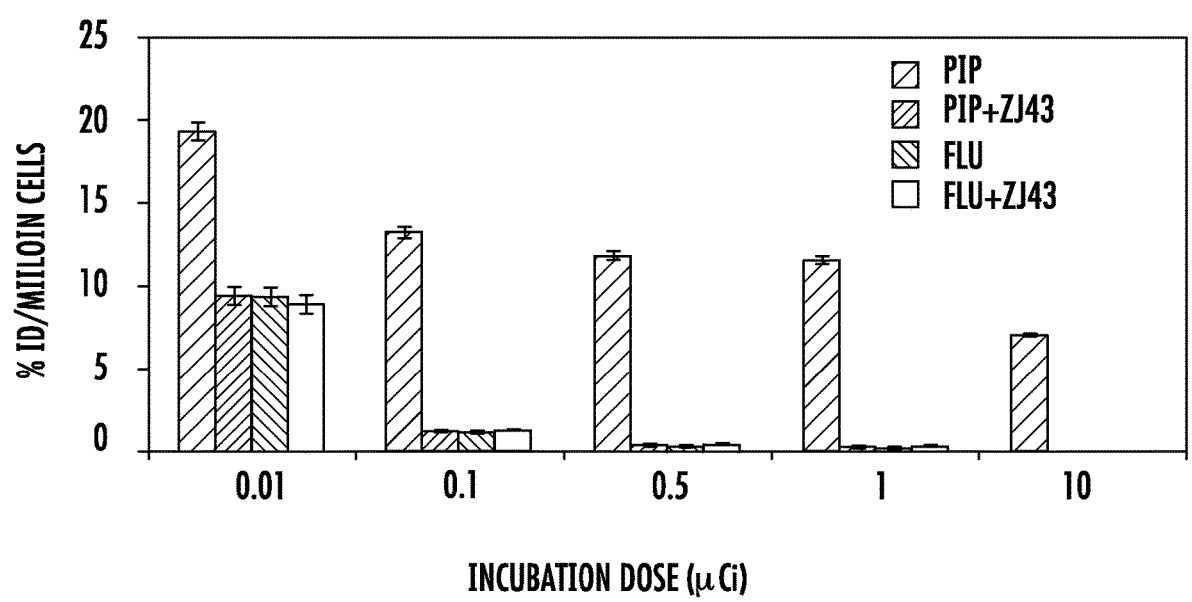
Figure 24:
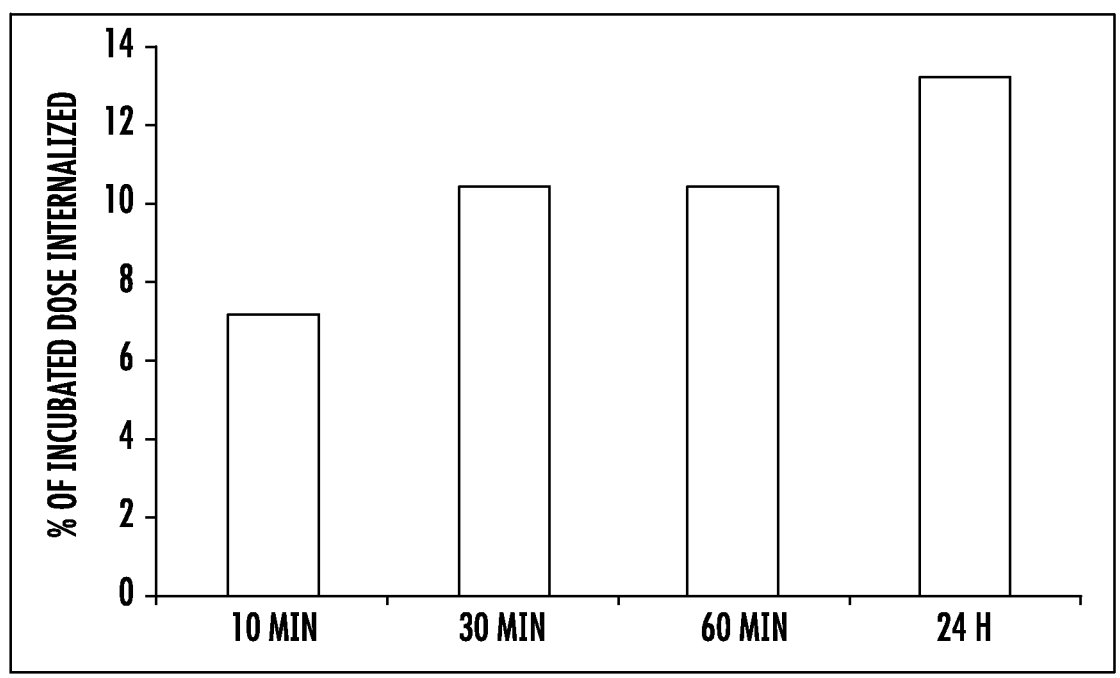
Figure 25A:
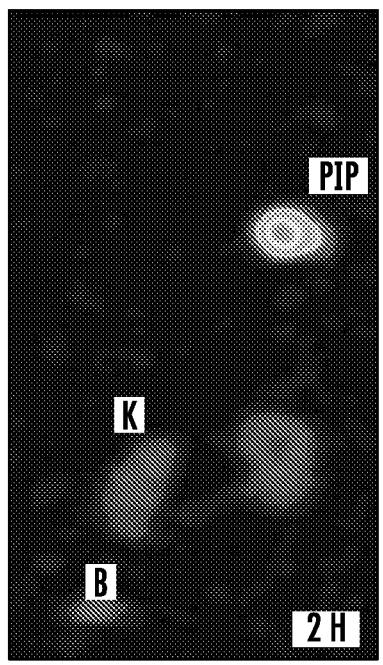
Figure 25B:
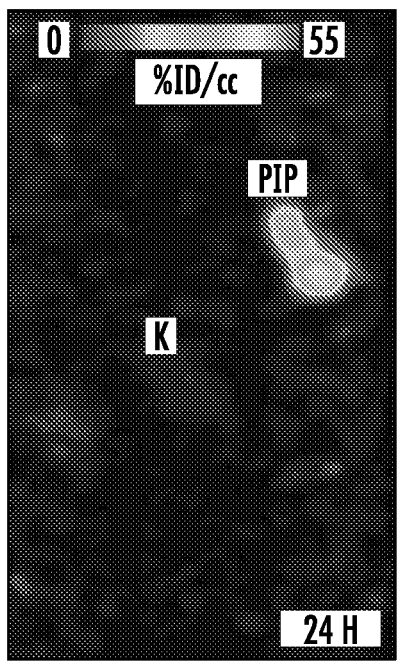
Figure 25C:
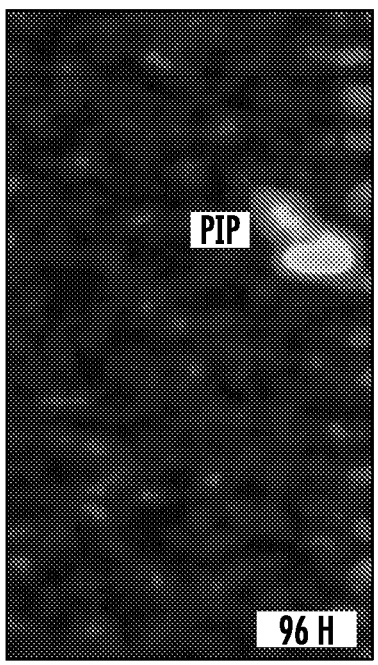

Having thus described the presently disclosed subject matter in general terms, reference will now be made to the accompanying Figures, which are not necessarily drawn to scale, and wherein:

FIGS. 1A and 1B are: (A) structures of Gd1, Gd2 and Gd3 and (B) $IC_{50}$ curves;

FIG. 2 shows the concentration of Gd1-Gd3 in PC3 PSMA− flu (blue) and PC3 PSMA+ PIP (red) cell pellets; the data were obtained from ICP-MS analyses;

FIG. 3 shows the percent of incubated dose (% ID) internalized and cell surface bound for Gd1 and Gd2; the data were obtained from ICP-MS analyses;

FIG. 4A through FIG. 4C show $T_1$ contrast enhancement generated by Gd3 in an isogenic human PC3 prostate cancer cell pair, PSMA+ PIP and PSMA− flu cells; (A) Color coded $T_1$ maps of PIP and flu cells. Relaxation rates were determined at 25° C. at 9.4 T; (B) Quantification of $T_1$ changes ($ΔT_1$) in PIP and flu cells (n=4, P<0.05) following treatment with Gd3; (C) cellular uptake of Gd3 in PIP and flu cells. The amount of Gd(III) associated with PIP cell pellets was significantly higher than for the flu cell pellets. The accumulation of Gd3 in PIP cells was blocked by pre-incubating with ZJ43 (n=4, P<0.05);

FIG. 5A through FIG. 5D show (A) the cellular uptake and internalization of Gd1-Rh by fluorescence imaging; PSMA+PC3 PIP and PSMA− PC3 flu cells were incubated with a serially diluted solution of Gd1-Rh (4 μM-4 nM) for 30 min at 37° C. followed by removal of excess contrast agents with cold PBS; the enlarged view of PC3 PIP (B) and PC3 flu (C) at 4 nM concentration of the contrast agent; rhodamine fluorescence is shown in red, and nuclei counter stained with DAPI are displayed in blue; (D) the structure of Gd1-Rh;

FIG. 6A and FIG. 6B show the % ID of Gd3 cell surface bound (A) and internalized (B) at 1, 4 and 24 h;

FIG. 7 shows the viability of PSMA− PC3 flu cells incubated with Gd1, Gd2, Gd3 and Prohance; contrast agents were incubated with cells at various Gd concentrations for 24 hours at 37° C. and viability was measured using an MTS assay; viability measurements were normalized to cells grown in the absence of any contrast agent;

FIG. 8 shows the viability of PSMA+PC3 PIP cells incubated with Gd1, Gd2, Gd3 and Prohance (Gd-DOTA); contrast agents were incubated with cells at various Gd concentrations for 24 hours at 37° C. and viability was measured using an MTS assay; viability measurements were normalized to cells grown in the absence of any contrast agent;

FIG. 9A and FIG. 9B show Gd3 MR imaging of human PC3 prostate cancer PSMA+ PIP and PSMA− flu tumor xenografts in male NOD/SCID mice. (A) Enhancement (ΔR1%) maps in PSMA+PC3 PIP and PSMA− PC3 flu tumors are superimposed upon T2-weighted images at 40 min, 80 min, 120 min and 160 min after a single bolus injection of Gd3 into the tail vein; (B) ΔR1% maps in PSMA+ and PSMA− tumors of a trimeric Gd contrast agent without a PSMA targeting moiety at 40 min, 80 min, 120 min and 160 min after a single bolus injection of Gd3 into the tail vein;

FIG. 10A and FIG. 10B show (A) $T_1$ time courses calculated for the entire volume of each tumor during 1-1600 min post-injection; and (B) the enlarged region of time-course at 0-200 min; high specific and persistent enhancement in the PSMA+PC3 PIP tumors was noted;

FIG. 11 shows the percent change in relaxivity (% $\Delta R_1$) for the mice after injection with 0.05 mmol/Kg dose (n=3) of Gd3. (p<0.03, PIP:flu);

FIG. 12 shows the in vivo time-dependent changes in $T_1$ values of the tumor (n=1) before and after injection of a 1×PBS (phosphate buffered saline);

FIG. 13A and FIG. 13B show (A) selected MR images presented in FIG. 11; and (B) the structure of Gd3;

FIG. 14 shows the structures of 86Y-Labeled inhibitors of PSMA;

FIG. 15A and FIG. 15B show preparative HPLC chromatograms for [$^{86}$Y]4; (A) radio-HPLC peak; and (B) and UV peak at 18.6 min is for unchelated 4 at λ=254 nm;

FIG. 16A and FIG. 16B show preparative HPLC chromatograms for [$^{86}$Y]5; (A) radio-HPLC peak and (B) UV peak at 34 min is for unchelated 5 at λ=254 nm;

FIG. 17A through 17C show preparative HPLC chromatograms for [$^{86}$Y]6: (A) radio-HPLC peak; (B) UV peak at 15.8 min is for unchelated 6 at λ=220 nm; and (C) HPLC chromatogram for pure [$^{86}$Y]6;

FIG. 18A through 18C show whole-body PET-CT imaging of (A)$^{86}$Y-4, (B)$^{86}$Y-5 and (C)$^{86}$Y-6 in mice bearing PSMA+PC3 PIP and PSMA− PC3 flu tumors at 2 h post-injection. Mice were injected with ~3.3 mBq (90 μCi) of radiotracer intravenously (IV). PSMA+PC3 PIP (solid arrow); PSMA− PC3 flu (unfilled arrow); K=kidney; GB=gallbladder; GI=gastrointestinal tract; L=left; R=right. Images are decay-corrected and scaled to the same maximum value;

FIGS. 19A and 19B show PET-CT imaging of [$^{86}$Y]-4 in mice bearing PSMA+PC3 PIP and PSMA− PC3 flu tumors. Images obtained (A) without, and (B) with blockade of PSMA using the potent, selective PSMA inhibitor, ZJ43, as the blocking agent (50 mg/kg). Reduction of radiotracer uptake in both the tumor and kidneys (another PSMA+ site) upon co-treatment with ZJ43 provided a further check on PSMA-specific binding. Mice were injected with ~6.2 MBq (168 μCi) of radiotracer IV. PSMA+PC3 PIP (solid arrow); PSMA− PC3 flu (unfilled arrow); K=kidney; B=bladder; L=left; R=right. Images are decay-corrected and scaled to the same maximum value; FIG. 19C shows the structure of the potent, selective PSMA inhibitor ZJ43;

FIG. 20A through FIG. 20C show PET-CT imaging of $^{86}$Y-6 in mice bearing PSMA+PC3 PIP and PSMA− PC3 flu tumors at (A) 0.5 h post-injection, (B) 2 h post-injection and (C) 12 h post-injection. Mice were injected with ~6.2 MBq (160 μCi) of radiotracer IV. PSMA+PC3 PIP (solid arrow); PSMA− PC3 flu (unfilled arrow); K=kidney; L=left; R=right. Images are decay-corrected and scaled to the same maximum value;

FIG. 21A and FIG. 21B show 3D time-course MIP (maximum intensity reprojection) display of $^{86}$Y-6 PET in a baboon at (A) 1-2 h post-injection and (B) 2-3.5 h post-injection. To enhance the visualization, bladder radioactivities were segmented semi-automatically using a thresholding method and subsequently removed. The MIP 3D rendering was employed to provide an overview of the whole-body radiotracer distribution. Little radiotracer was observed in most normal tissues except for bladder (not shown) and kidney (K). The animal was catheterized for this study. Mild uptake in the lacrimal glands, parotids and salivary glands was noted (short, long and unfilled arrows, respectively);

FIG. 22 shows the structures of $^{177}$Lu-SRV171 and related proposed agents to further improve the in-vivo pharmacokinetics;

FIG. 23 shows the percent of incubated of dose (ID) of $^{177}$Lu-SRV171 (0.01-10 μCi/million cells of PSMA+ PIP and PSMA− flu cells after 2 h at 37° C. Uptake specificity was further checked by co-incubation of 10 μM of ZJ43;

FIG. 24 shows the internalization study of $^{177}$Lu-SRV171 (1 μCi) up to 24 h;

FIG. 25A through FIG. 25C show SPECT images of male mouse bearing PIP and flu tumor using $^{171}$Lu-SRV171 (500 μCi) at (A)2 h post injection, (B) 24 h post-injection and (C) 96 h post-injection. Low uptake was found in kidney (K), bladder (B) and flu tumor.

Figure 26:
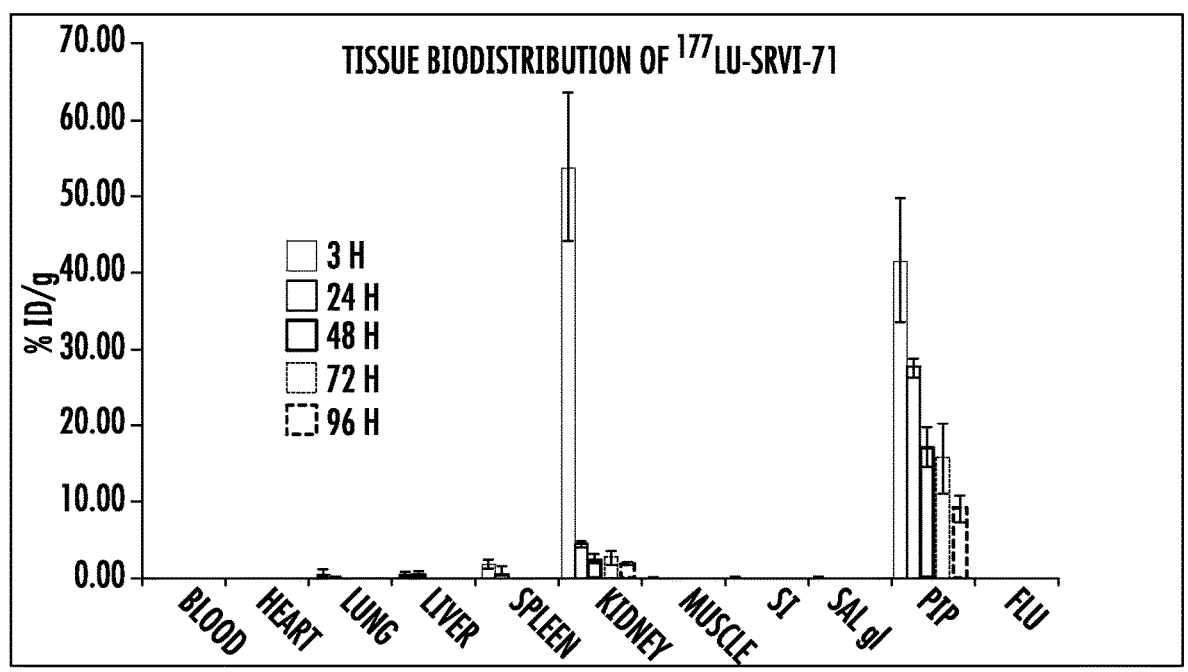
Figure 27:
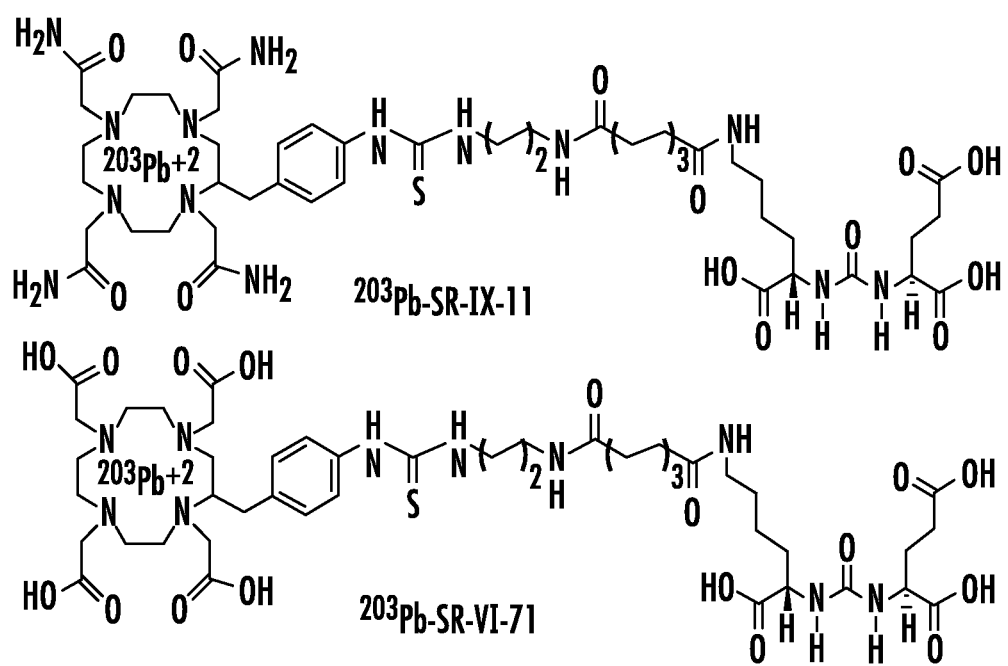
Figure 28A:
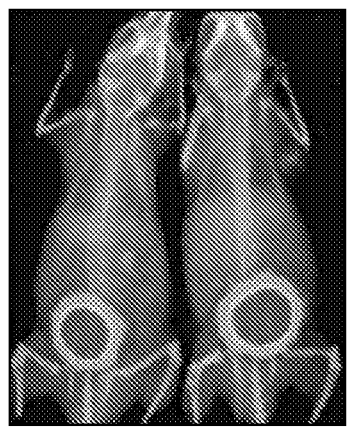
Figure 28B:
Figure 28C:
Figure 29:
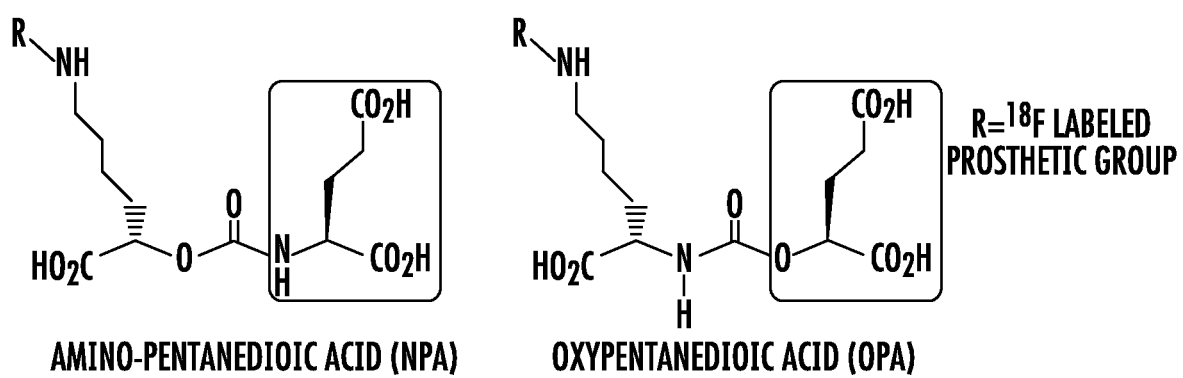
Figure 30:
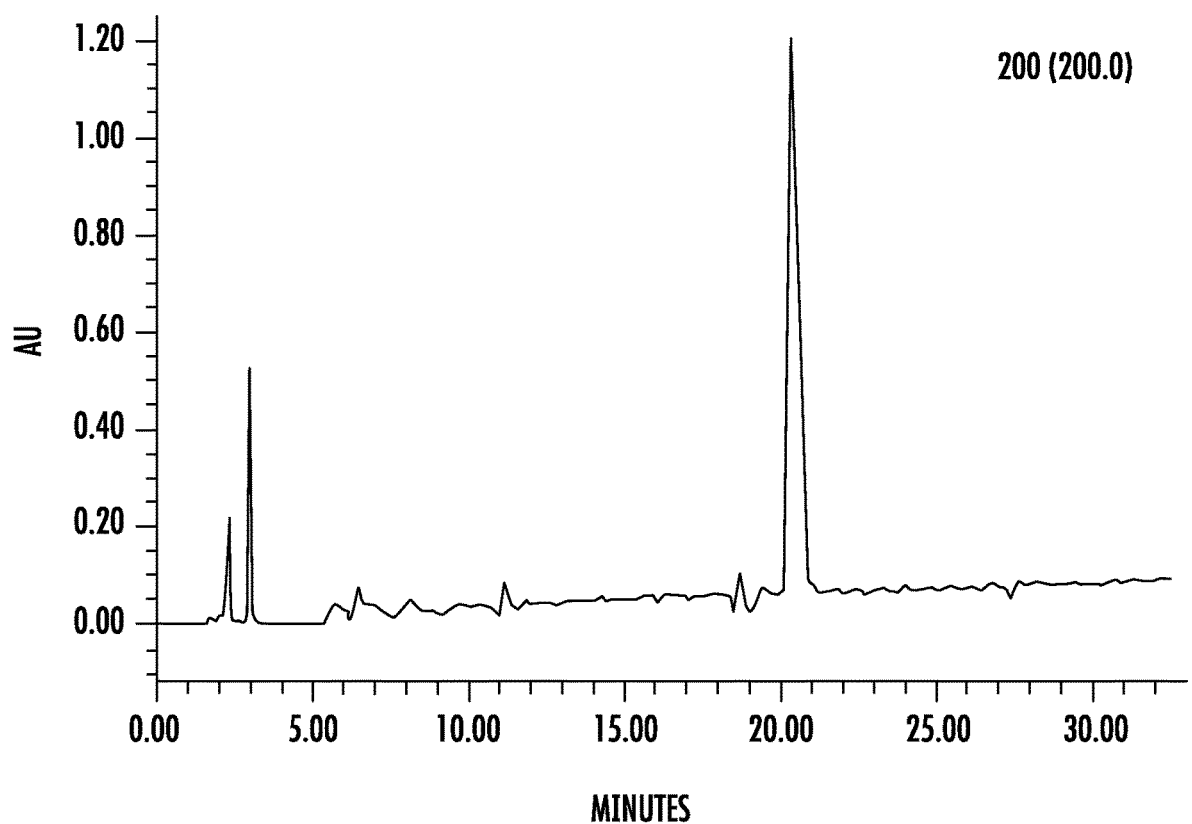
Figure 31:
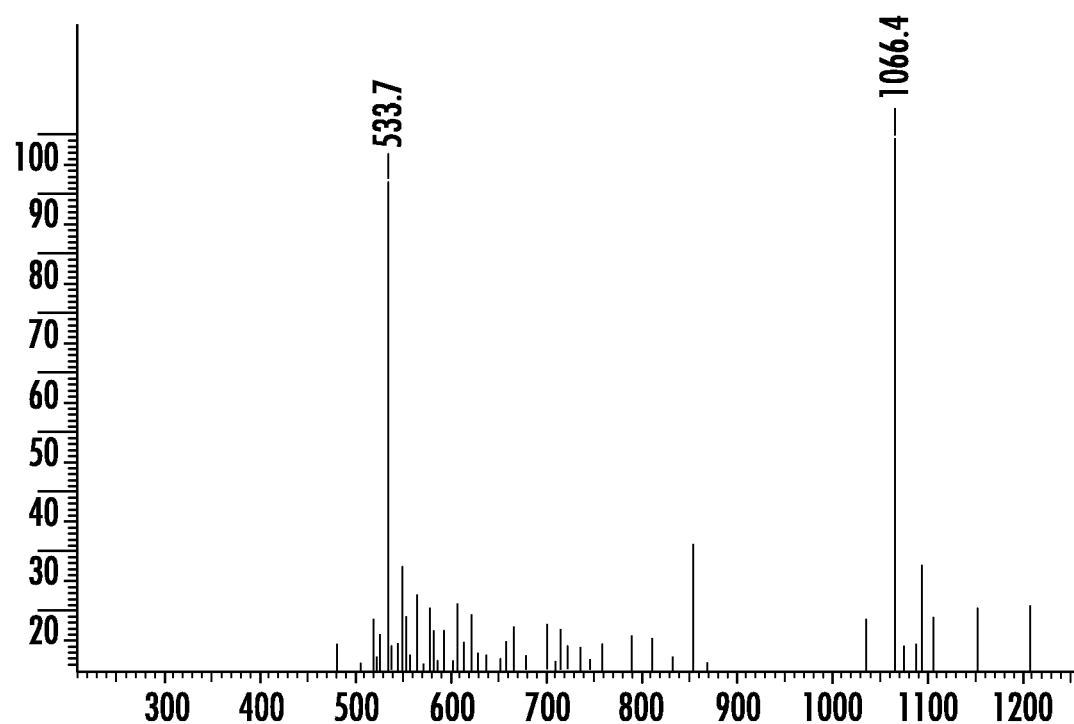
Figure 32:
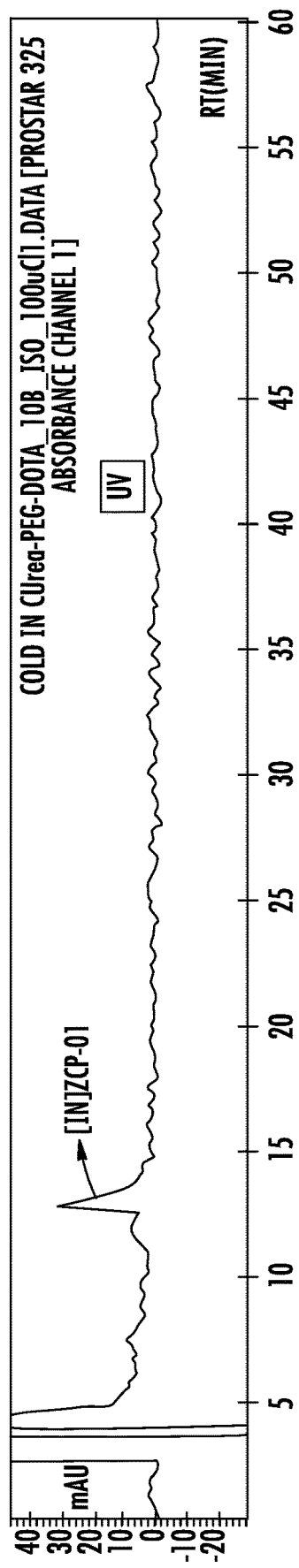
Figure 33A:
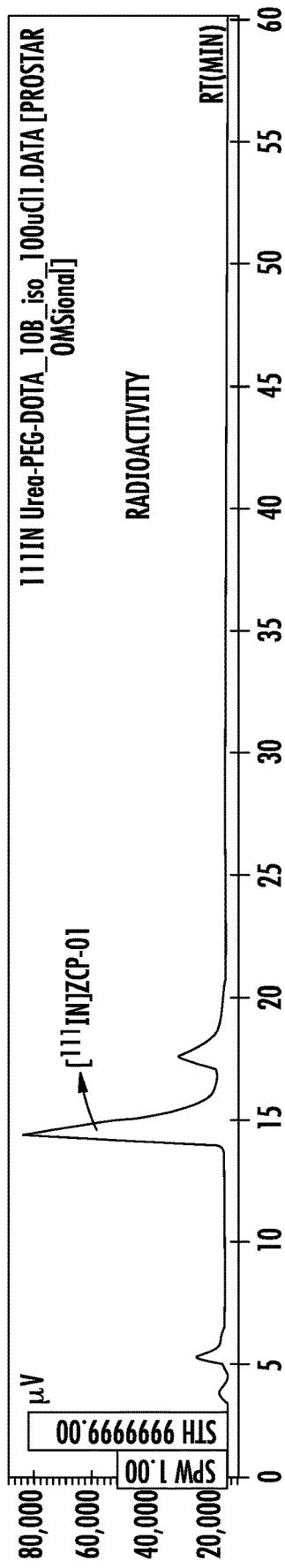
Figure 33B:
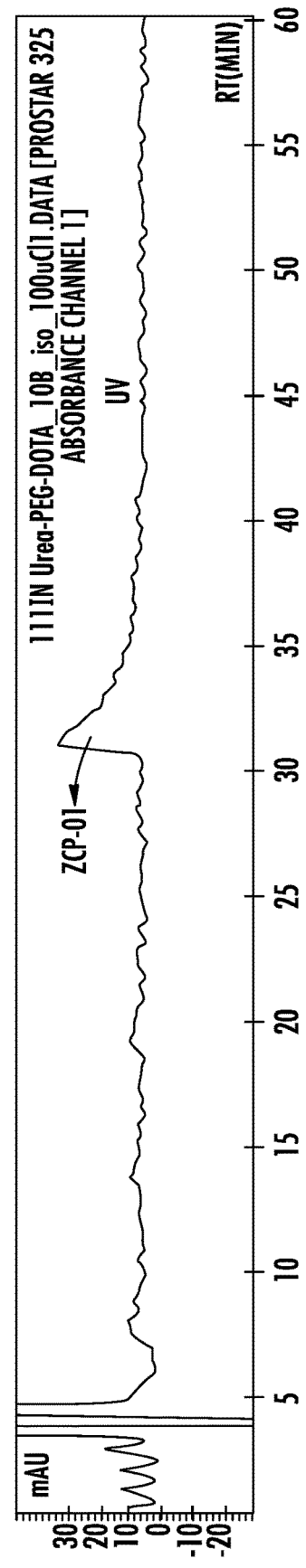
Figures 34A, 34B, 34C:
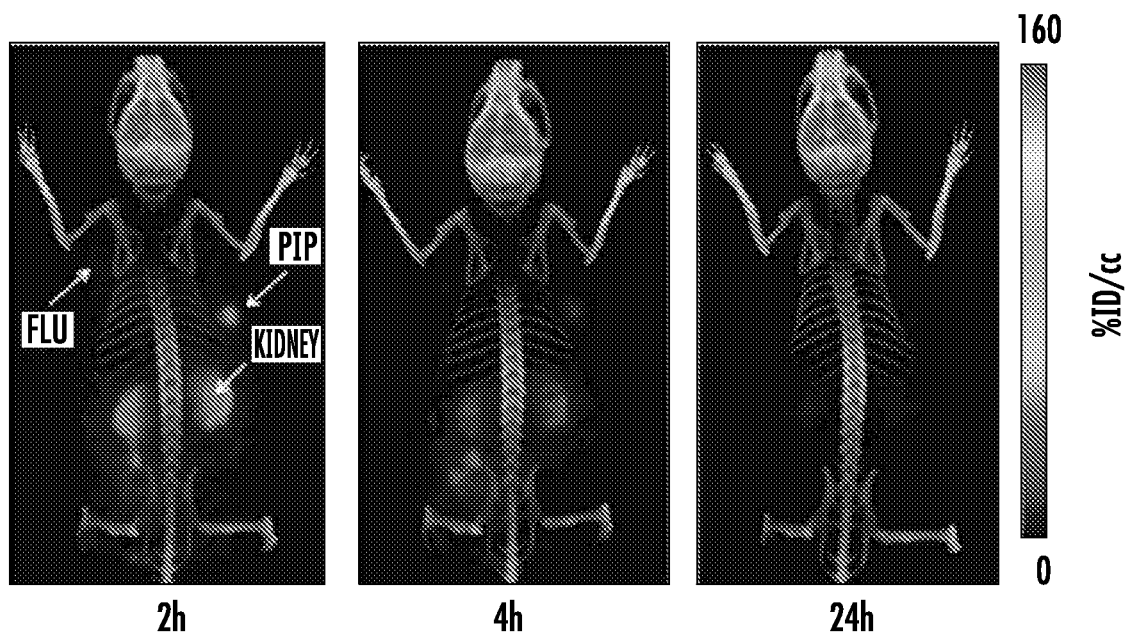

FIG. 26 shows the tissue biodistribution of $^{177}$Lu-SRV171 in different organs at 3 h, 24 h, 48 h, 72 h and 96 h post-injection;

FIG. 27 shows the structures of $^{203}$Pb-SR-IX-11 and $^{203}$Pb-SRV171;

FIG. 28A through 28C show SPECT-CT images of male mouse bearing PIP and flu tumor using $^{203}$Pb-SRV171 (left) and $^{203}$Pb-SR-IX-11 (right) at (A) 60 min. post-injection, (B) 120 min. post-injection and (C) 240 min. post-injection;

FIG. 29 shows two lysine-carbamate scaffolds used to design compounds of the presently disclosed subject matter: oxypentanedioic acid (OPA) corresponding to a carbamate scaffold and amino-pentanedioic acid (NPA) corresponding to a "reverse" carbamate scaffold;

FIG. 30 shows the HPLC chromatogram of ZCP-01;

FIG. 31 Shows the Electrospray Ionisation Mass Spectrometry (ESI-MS) of cold [In] ZPC-01;

FIG. 32 shows the HPLC chromatogram of cold [In] ZCP-01;

FIGS. 33A and 33B show preparative HPLC chromatograms for [In] ZCP-01; (A) radio-HPLC peak; and (B) and UV peak at 32 min is for unchelated ZCP-01 at λ=200 nm; and FIGS. 34A through 34C show the uptake of [$^{111}$In]ZCP-01 in mice bearing PSMA+PC3 Pip and PSMA− PC flu tumor xenografts (A) 2 h, (B) 4 h and (C) 24 h after injection.

DETAILED DESCRIPTION

The presently disclosed subject matter now will be described more fully hereinafter with reference to the accompanying Examples and Figures, in which some, but not all embodiments of the presently disclosed subject matter are illustrated. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions and the associated Examples and Figures. Therefore, it is to be understood that the presently disclosed subject matter is not to be limited to the specific embodiments disclosed and that modifications and other embodiments are intended to be included within the scope of the appended claims.

I. Metal/Radiometal-Labeled PSMA Inhibitors for PSMA-Targeted Imaging and Radiotherapy Magnetic resonance (MR) imaging is advantageous because it can provide anatomic, functional and molecular information concurrently. MR molecular imaging can combine the ubiquity of this established clinical modality and its high spatial resolution with molecular profiling in vivo. However, due to the intrinsically low sensitivity of MR, high local concentrations of biological targets are required to generate discernable MR contrast.

Without wishing to be bound to any one particular theory, it was thought that PSMA would be good target for MR molecular imaging agents because of the high target concentration per cell (approximately 3 μM/cell volume), as well as the extra-cellular location of the ligand binding site. The presently disclosed approach is directed toward improving the binding affinity (lowest $K_d$) of contrast agents for a specific molecular or cellular target so that the amount of agent needed for MR-detection will be much lesser. Accordingly, the presently disclosed approach combines a high binding affinity receptor specific ligand with multimeric Gd(III) agents as one possible solution for MR-based molecular imaging.

Previously, successful radiometal-based PET ($^{64}$Cu) and SPECT ($^{111}$In and $^{99m}$Tc) imaging was demonstrated using radiolabeled, urea-based PSMA inhibitors in mice. A tripartite strategy containing a: (i) PSMA targeting moiety, (ii) linker for pharmacokinetic tuning, and (iii) chelating agent to enable attachment of radionuclides was developed. This strategy included $^{86}$Y labeled DOTA conjugated agents for PET imaging and to serve as a model for radiotherapy with corresponding $^{90}$Y labeled agents. Because DOTA is a strong chelating agent for many metals the same DOTA conjugates can be used with other radiotherapeutic radionuclides, such as Lu-177, Ac-225, Bi-213, Bi-212, Pb-212, Cu-67, and Sc-47. In the presently disclosed subject matter, the same urea-linker construct was used and the number of Gd-chelates (mono-, di- and trimeric Gd) was increased to optimize relaxometric behavior or MR sensitivity as high field contrast agents as well as their binding affinity to investigate systematically the possibility of PSMA-based MR imaging of PCa.

A. Compounds of Formula (I)

Accordingly in some embodiments, the presently disclosed subject matter provides a compound of formula (I):

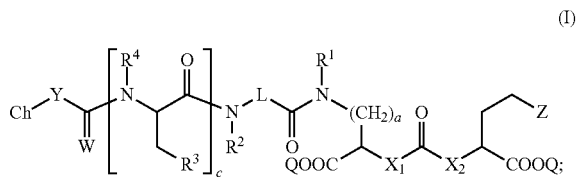

wherein: Z is tetrazole or $CO_2Q$; Q is H or a protecting group; $X_1$ and $X_2$ are each independently NH or O; a is an integer selected from the group consisting of 1, 2, 3 and 4; c is an integer selected from the group consisting of 0, 1, 2, 3 and 4; each $R^1$, $R^2$ and $R^4$ is independently H or $C_1$-$C_4$ alkyl; each $R^3$ is independently H, $C_1$-$C_6$ alkyl or $C_2$-$C_{12}$ aryl; W is independently O or S; Y is —NH— and can be present or absent; L is a linker selected from the group consisting of:

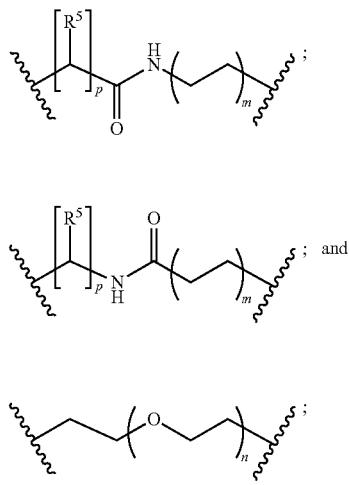

wherein: m is an integer selected from the group consisting of 1, 2, 3, 4, 5, 6, 7 and 8; each $R^5$ is independently H or —COOR$^6$ wherein each $R^6$ is independently H or a $C_1$-$C_6$ alkyl; n is an integer selected from the group consisting of 1, 2, 3, 4, 5, 6, 7, 8, 9, 10, 11 and 12; p is an integer selected from the group consisting of 1, 2, 3, 4, 5, 6, 7 and 8; Ch is a chelating moiety that can comprise one or more metals or radiometals; or a pharmaceutically acceptable salt thereof.

Formula (I) does not include compounds disclosed in WO 2009/002529, WO 2010/108125 and WO 2013/082338, in particular, the following compounds are expressly disclaimed from the composition of matter claims in the present application:

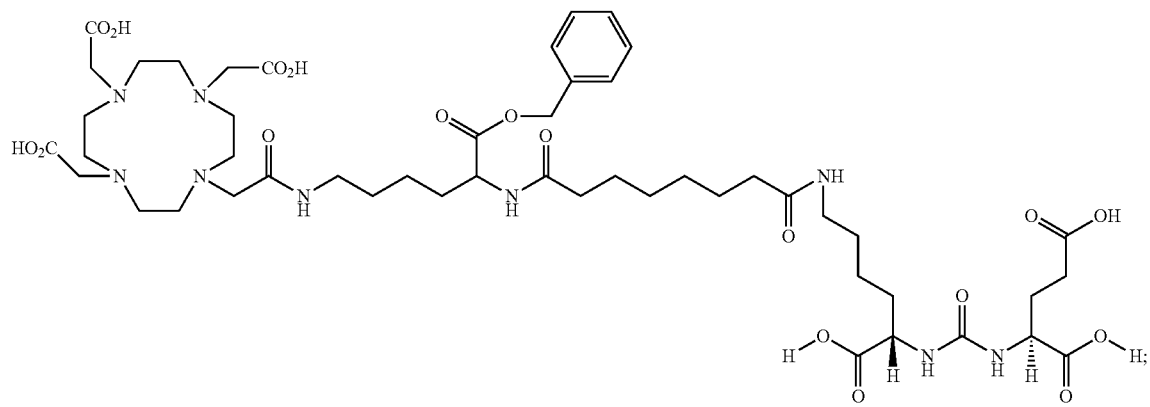
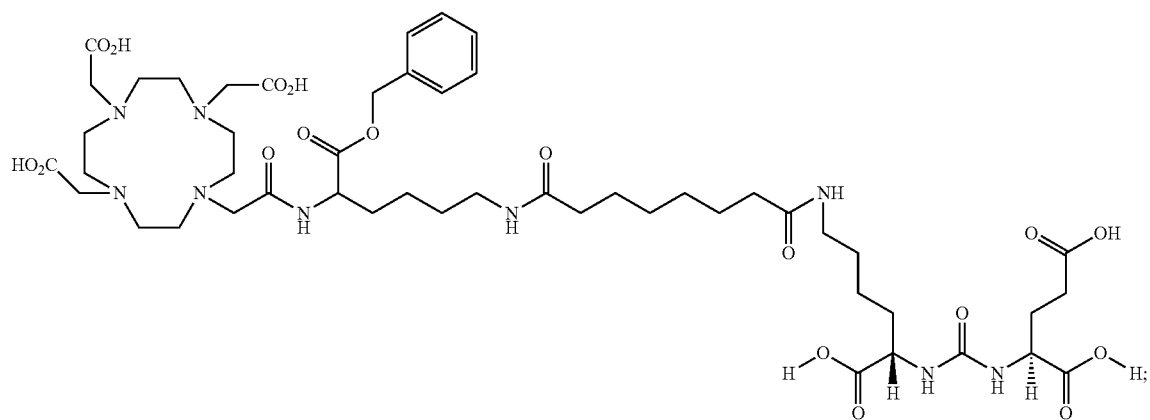
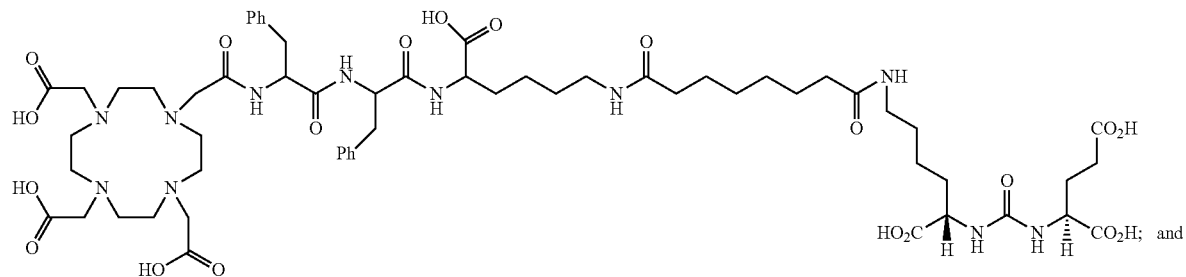
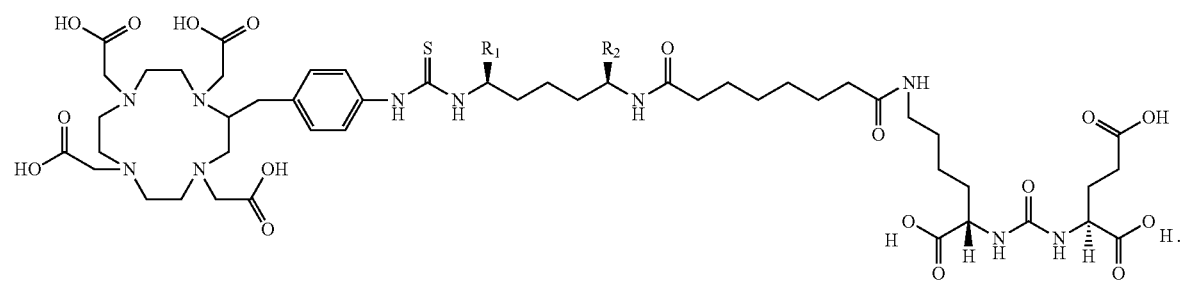
R₁ = H, R₂ = CO₂H, DOTA-L3

In more particular embodiments the chelating moiety is selected from the group consisting of:
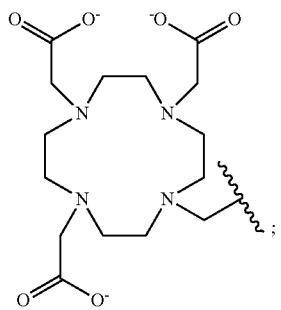
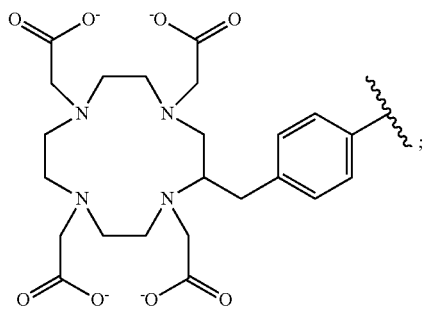
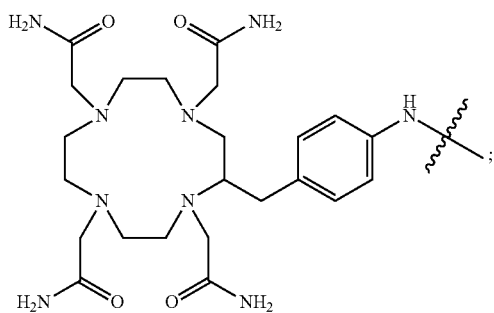
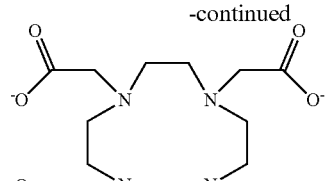
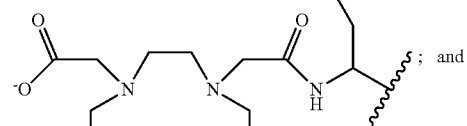
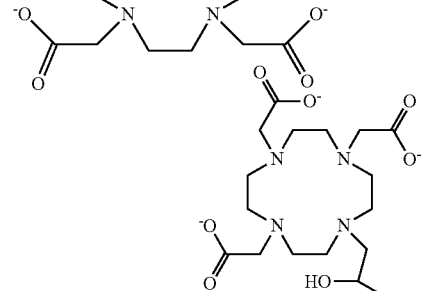
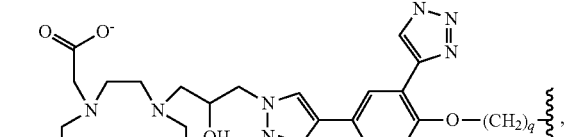
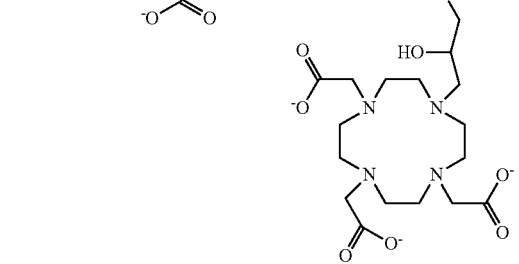
wherein q is an integer selected from the group consisting of 1, 2, 3, 4, 5, 6, 7 and 8.
In yet more particular embodiments, the compound of Formula (I) is selected from the group consisting of:
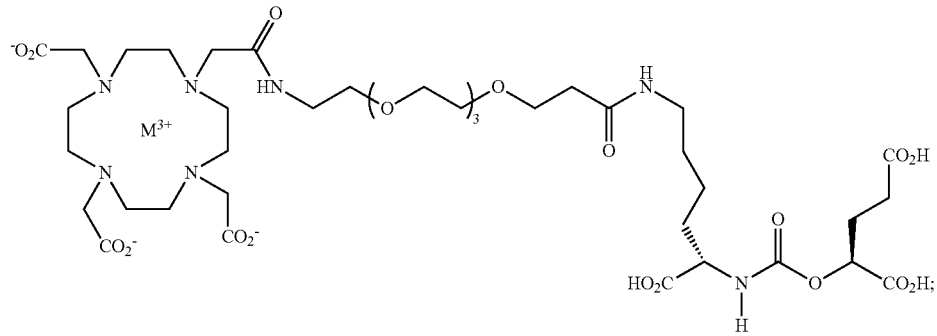

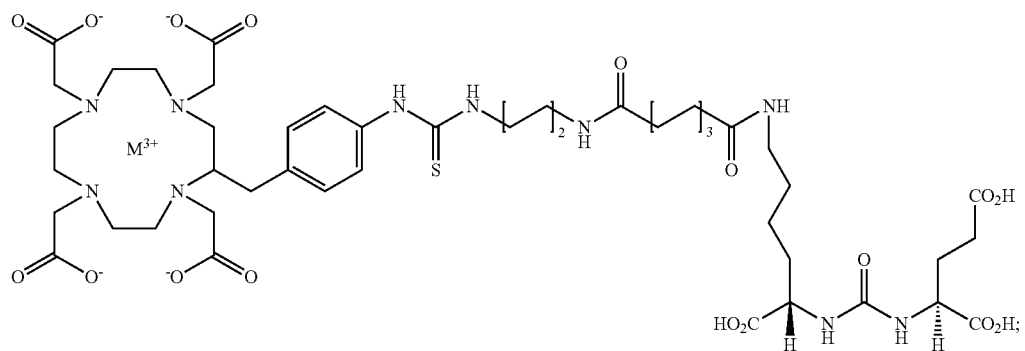
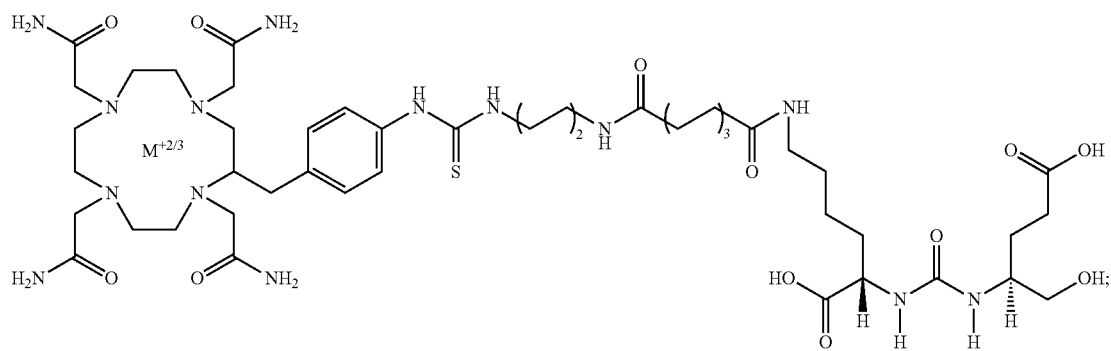
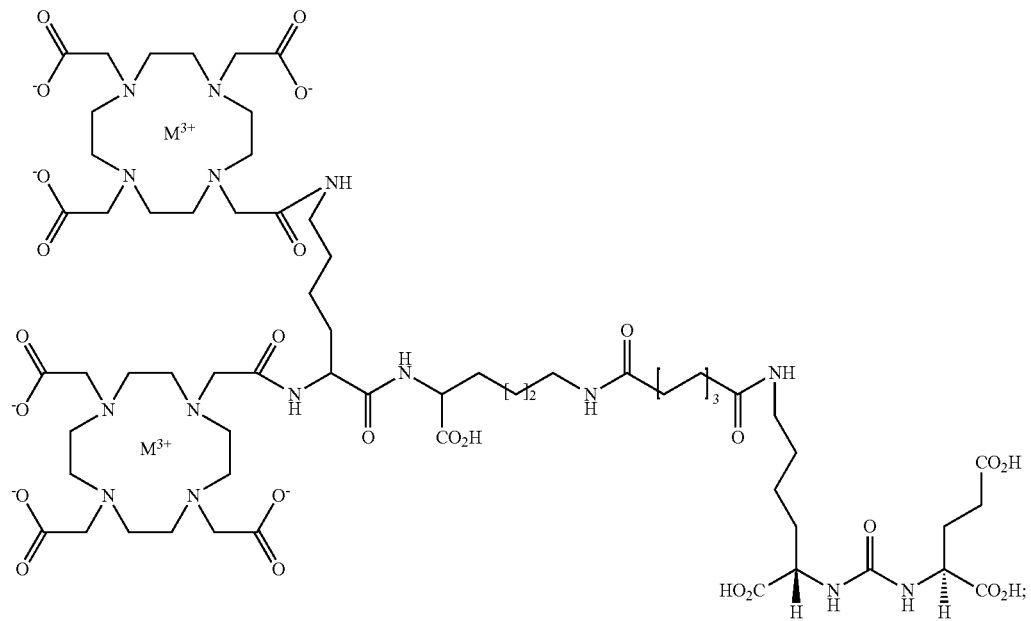

-continued

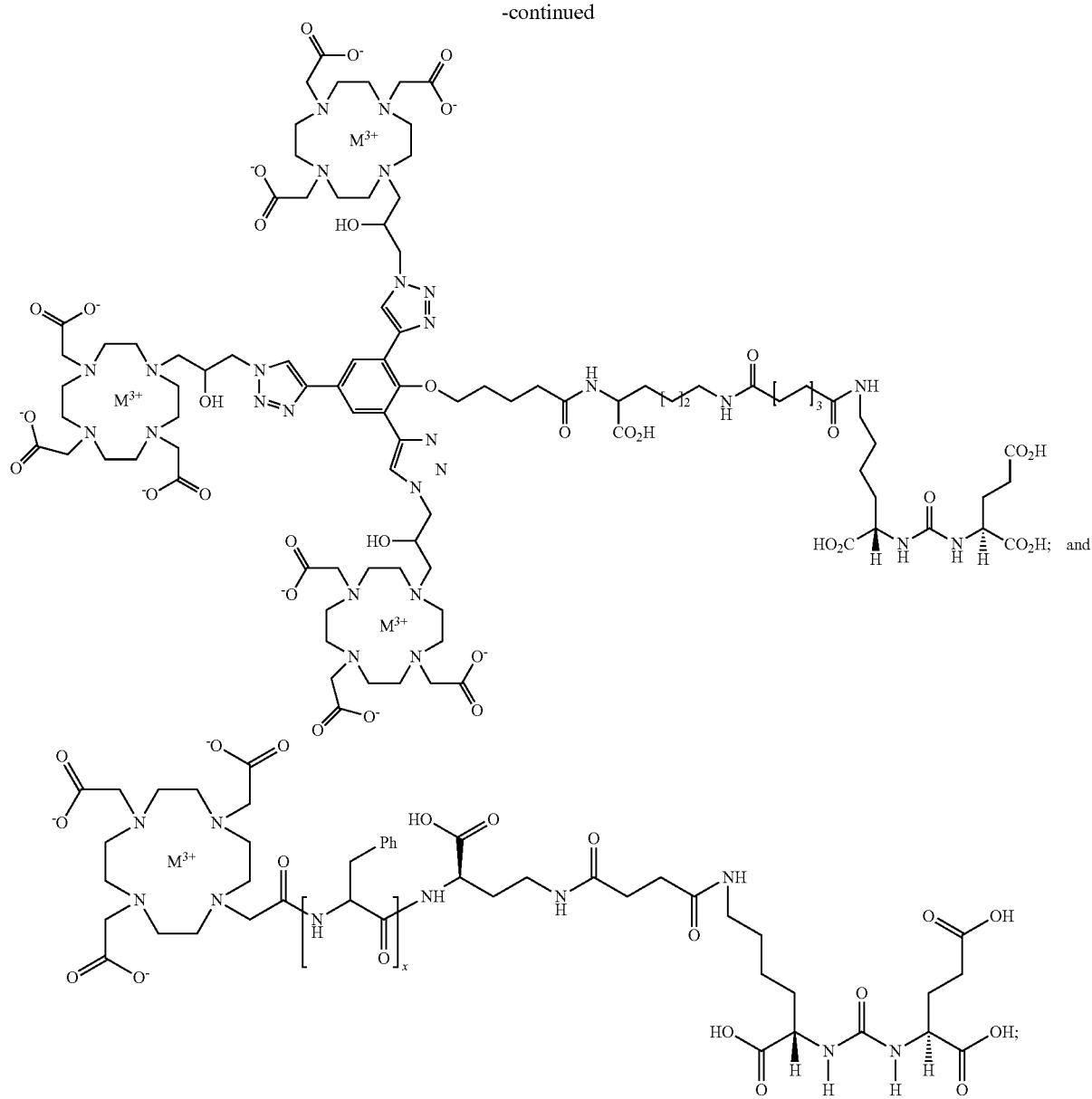

wherein:
- x is selected from the group consisting of 2 and 3;
- M is a metal or a radiometal; or
- a pharmaceutically acceptable salt thereof.

In some embodiments, the metal is selected from the group consisting of Gd, Lu, Ac, Bi, Pb, Cu, In, Sc, and Y. In particular embodiments, the metal or the radiometal is selected from the group consisting of Gd-157, Lu-177, Ac-225, Bi-212, Bi-213, Pb-203/Pb-212, Cu-67, In-111, Sc-44/Sc-47, and Y-90. In yet more particular embodiments, for MRI applications, the nonradioactive metal is Gd-157 (stable isotope); for radiotherapy applications, the radiometal is selected from the group consisting of Lu-177, Ac-225, Bi-203, Pb-210, Cu-67, In-111, Sc-47, and Y-90; for PET imaging, the radiometal is selected from the group consisting of Y-86 and Sc-44; and for SPECT application, the radiometal is selected from the group consisting of Lu-177 and In-111.

B. Methods of Using Compounds of Formula (I) for MR Imaging and/or Treating a PSMA-Expressing Tumor or Cell In some embodiments, the presently disclosed subject matter provides a method for imaging or treating one or more prostate-specific membrane antigen (PSMA) tumors or cells, the method comprising contacting the one or more tumors or cells with an effective amount of a compound of formula (I) and making an image, the compound of formula (I) comprising:

(I)

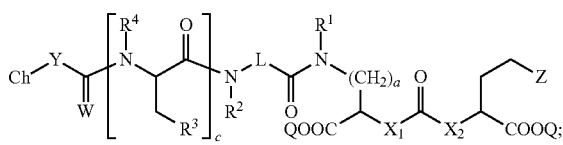

wherein: Z is tetrazole or $CO_2Q$; Q is H or a protecting group; $X_1$ and $X_2$ are each independently NH or O; a is an integer selected from the group consisting of 1, 2, 3 and 4; c is an integer selected from the group consisting of 0, 1, 2, 3 and 4; each $R^1$, $R^2$, $R^3$ and $R^4$ is independently H or $C_1$-$C_4$ alkyl; W is independently O or S; Y is —NH— and can be present or absent; L is a linker selected from the group consisting of:

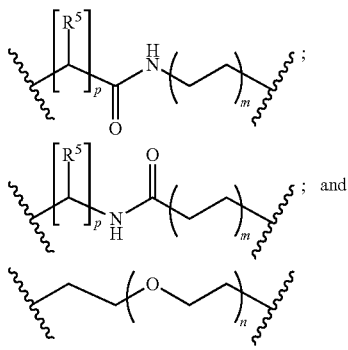

wherein: m is an integer selected from the group consisting of 1, 2, 3, 4, 5, 6, 7 and 8; each $R^5$ is independently H or —$COOR^6$ wherein each $R^6$ is independently H or a $C_1$-$C_6$ alkyl; n is an integer selected from the group consisting of 1, 2, 3, 4, 5, 6, 7, 8, 9, 10, 11 and 12; p is an integer selected from the group consisting of 1, 2, 3, 4, 5, 6, 7 and 8; Ch is a chelating moiety that can comprise one or more metals or radiometals; or a pharmaceutically acceptable salt thereof.

"Contacting" means any action which results in at least one compound comprising the imaging agent of the presently disclosed subject matter physically contacting at least one PSMA-expressing tumor or cell. Contacting can include exposing the cell(s) or tumor(s) to the compound in an amount sufficient to result in contact of at least one compound with at least one cell or tumor. The method can be practiced in vitro or ex vivo by introducing, and preferably mixing, the compound and cell(s) or tumor(s) in a controlled environment, such as a culture dish or tube. The method can be practiced in vivo, in which case contacting means exposing at least one cell or tumor in a subject to at least one compound of the presently disclosed subject matter, such as administering the compound to a subject via any suitable route. According to the presently disclosed subject matter, contacting may comprise introducing, exposing, and the like, the compound at a site distant to the cells to be contacted, and allowing the bodily functions of the subject, or natural (e.g., diffusion) or man-induced (e.g., swirling) movements of fluids to result in contact of the compound and cell(s) or tumor(s). In some embodiments, the tumor or cell is found in vitro, in vivo, or ex vivo.

By "making an image," it is meant using a magnetic resonance (MR)-based (magnets that polarize and excite hydrogen nuclei in water molecules in tissue to produce a detectable signal) to form an image of a cell, tissue, tumor, part of body, and the like.

Formula (I) does not include compounds disclosed in WO 2009/002529, WO 2010/108125 and WO 2013/082338, in particular, the following compounds are expressly disclaimed from imaging claims in the present application:

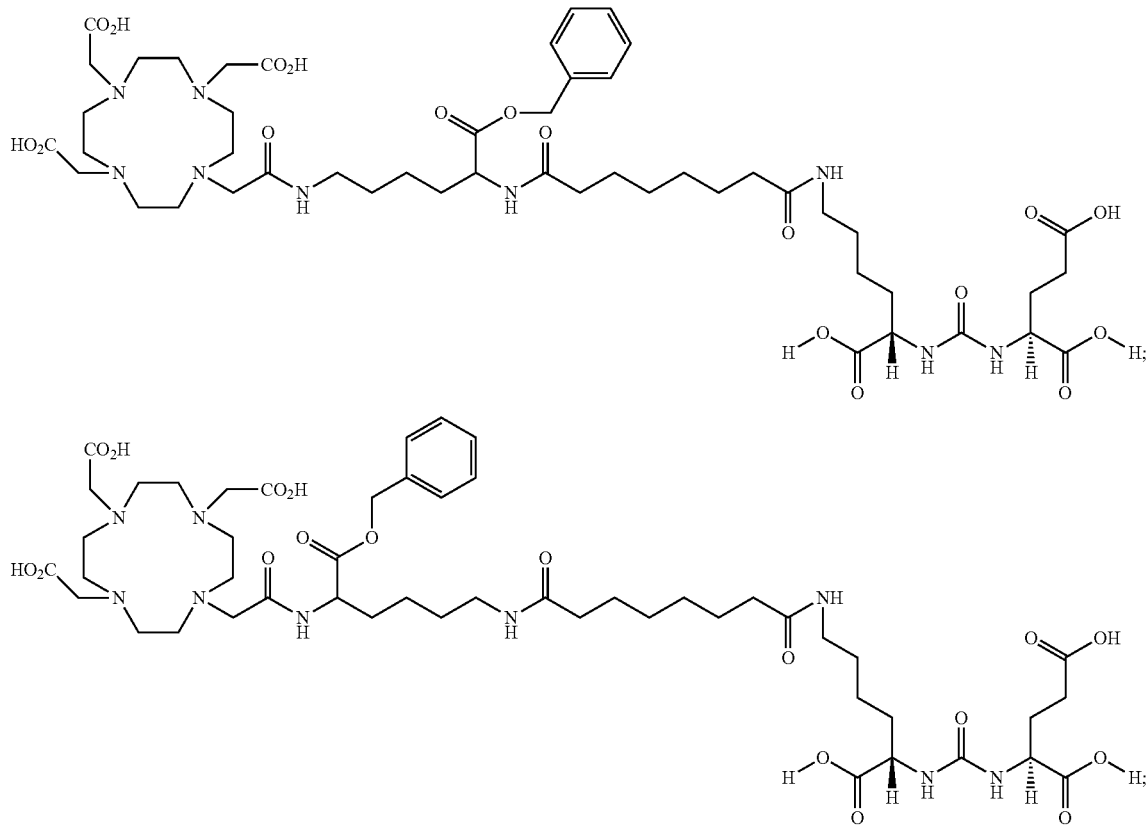

-continued
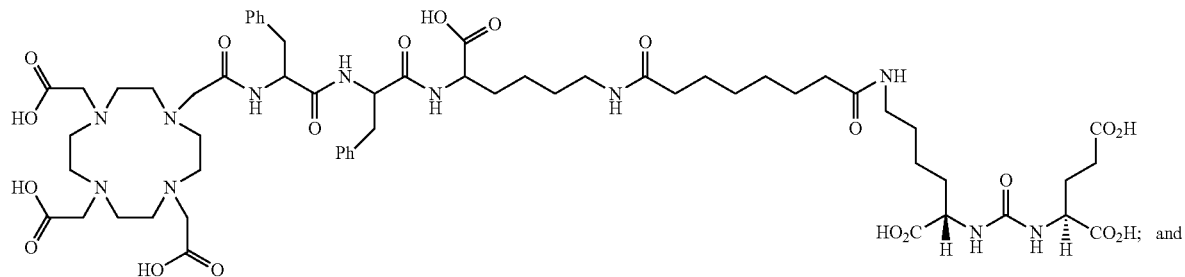
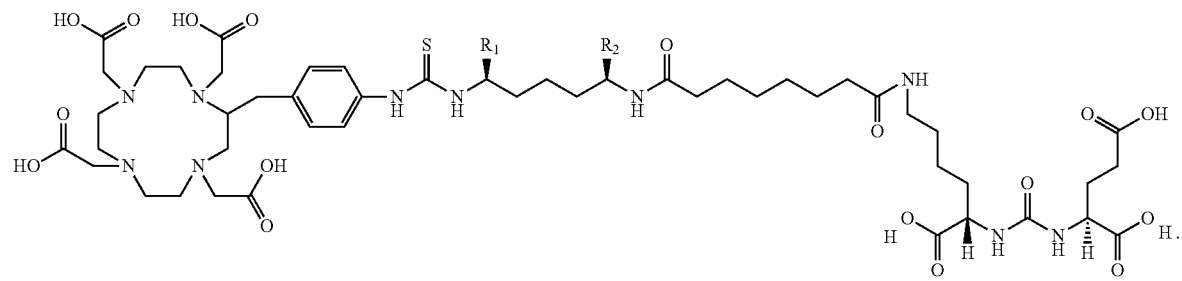
$R_1 = H, R_2 = CO_2H, DOTA-L3$
In more particular embodiments the chelating moiety is selected from the group consisting of:
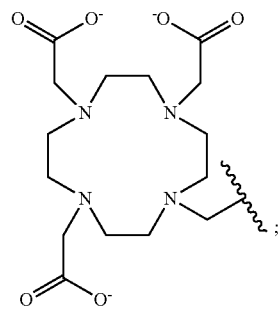
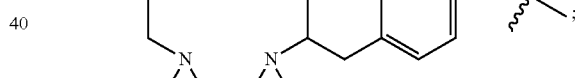
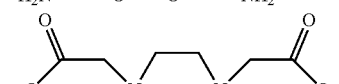
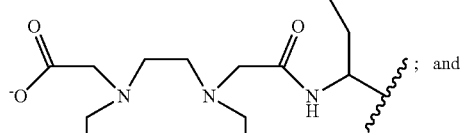
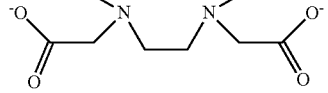

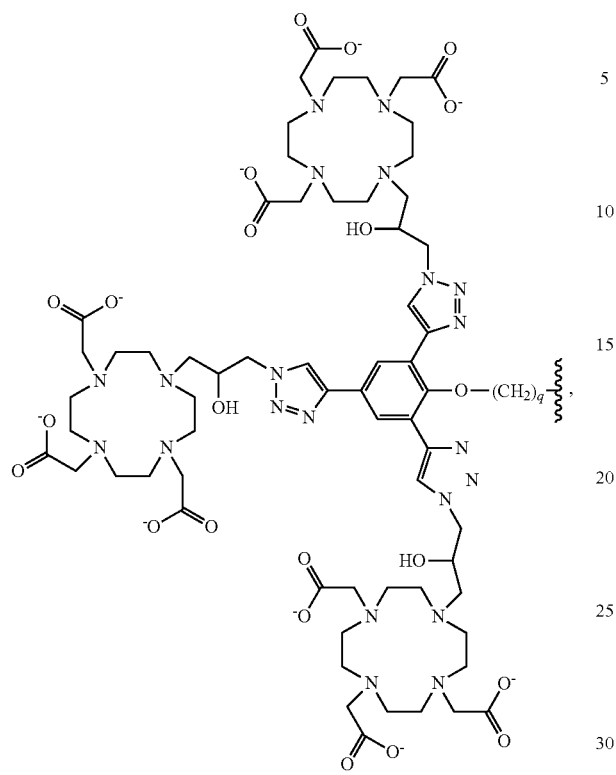
wherein q is an integer selected from the group consisting of 1, 2, 3, 4, 5, 6, 7, and 8.
In yet more particular embodiments the compound is selected from the group consisting of:
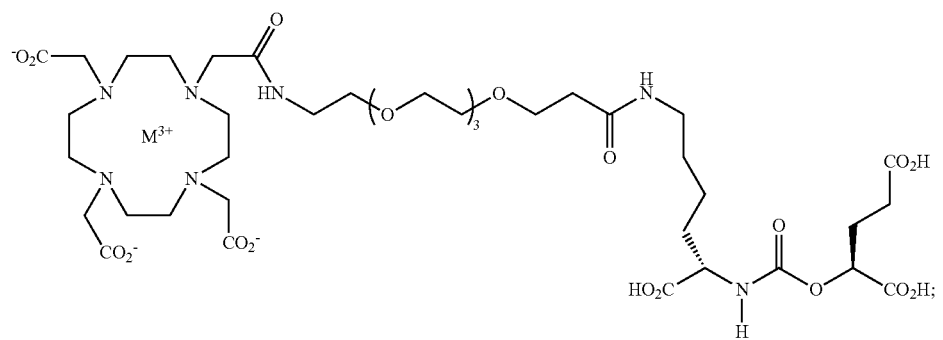
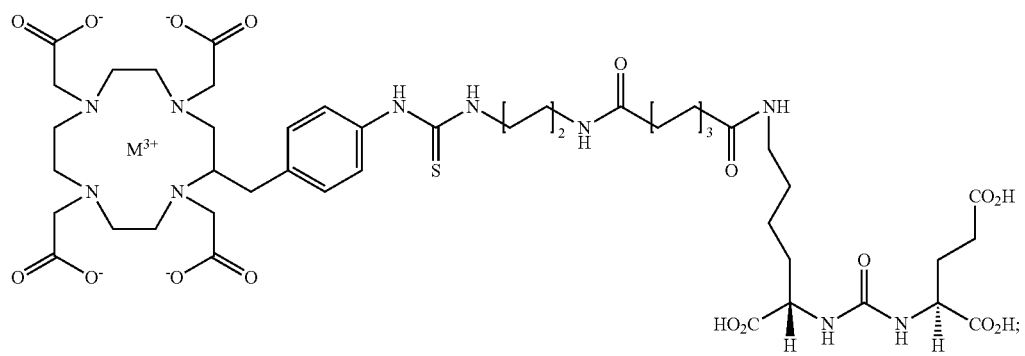

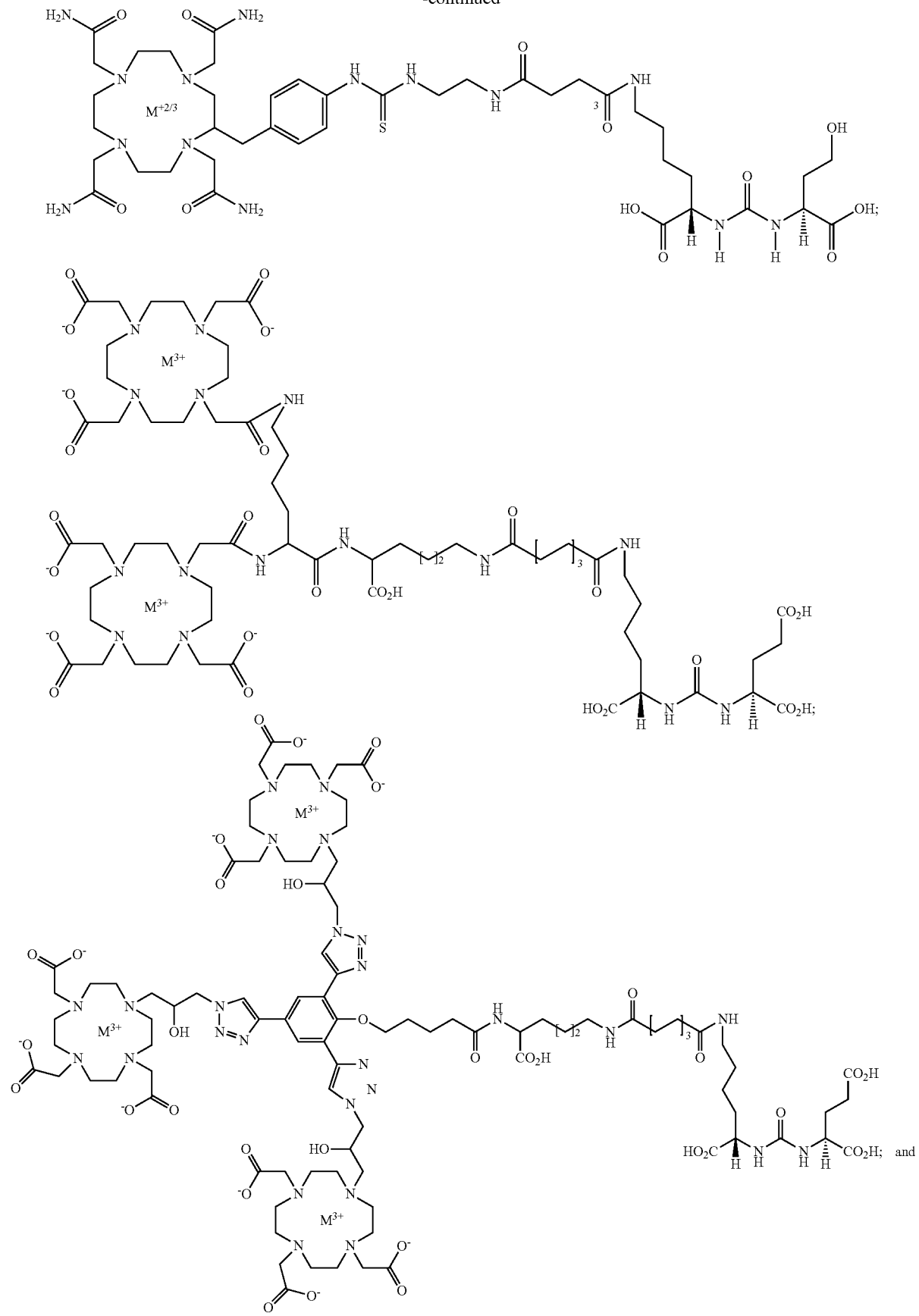

-continued

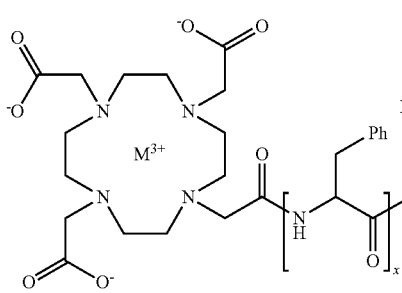 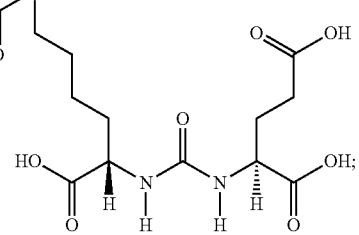

wherein:
x is selected from the group consisting of 2 and 3;
M is a metal or a radiometal; or
a pharmaceutically acceptable salt thereof.

In some embodiments, the metal is selected from the group consisting of Gd, Lu, Ac, Bi, Pb, Cu, In, Sc, and Y. In particular embodiments, the metal or the radiometal is selected from the group consisting of Gd-157, Lu-177, Ac-225, Bi-203, Pb-210, Cu-67, In-111, 44Sc-/47Sc, and Y-90. In yet more particular embodiments, for MRI applications, the nonradioactive metal is Gd-157 (stable isotope); for radiotherapy applications, the radiometal is selected from the group consisting of Lu-177, Ac-225, Bi-203, Pb-210, Cu-67, In-111, Sc-47, and Y-90; for PET imaging, the radiometal is selected from the group consisting of Y-86 and Sc-44; and for SPECT application, the radiometal is selected from the group consisting of Lu-177 and In-111.

In certain embodiments, the one or more PSMA-expressing tumors or cells is selected from the group consisting of: a prostate tumor or cell, a metastasized prostate tumor or cell, a lung tumor or cell, a renal tumor or cell, a glioblastoma, a pancreatic tumor or cell, a bladder tumor or cell, a sarcoma, a melanoma, a breast tumor or cell, a colon tumor or cell, a germ cell, a pheochromocytoma, an esophageal tumor or cell, a stomach tumor or cell, and combinations thereof. In yet more certain embodiments, the one or more PSMA-expressing tumors or cells is a prostate tumor or cell.

In some embodiments, the one or more PSMA-expressing tumors or cells is in vitro, in vivo, or ex vivo. In particular embodiments, the one or more PSMA-expressing tumors or cells is present in a subject.

In some embodiments, the tumor or cell is found in a subject. The subject treated by the presently disclosed methods in their many embodiments is desirably a human subject, although it is to be understood that the methods described herein are effective with respect to all vertebrate species, which are intended to be included in the term "subject." Accordingly, a "subject" can include a human subject for medical purposes, such as for the treatment of an existing condition or disease or the prophylactic treatment for preventing the onset of a condition or disease, or an animal (non-human) subject for medical, veterinary purposes, or developmental purposes. Suitable animal subjects include mammals including, but not limited to, primates, e.g., humans, monkeys, apes, and the like; bovines, e.g., cattle, oxen, and the like; ovines, e.g., sheep and the like; caprines, e.g., goats and the like; porcines, e.g., pigs, hogs, and the like; equines, e.g., horses, donkeys, zebras, and the like; felines, including wild and domestic cats; canines, including dogs; lagomorphs, including rabbits, hares, and the like; and rodents, including mice, rats, and the like. An animal may be a transgenic animal. In some embodiments, the subject is a human including, but not limited to, fetal, neonatal, infant, juvenile, and adult subjects. Further, a "subject" can include a patient afflicted with or suspected of being afflicted with a condition or disease. Thus, the terms "subject" and "patient" are used interchangeably herein. In some embodiments, the subject is human. In other embodiments, the subject is non-human.

In some embodiments, a detectably effective amount of the imaging agent of the presently disclosed methods is administered to a subject. In accordance with the presently disclosed subject matter, "a detectably effective amount" of the imaging agent is defined as an amount sufficient to yield an acceptable image using equipment which is available for clinical use. A detectably effective amount of the imaging agent may be administered in more than one injection. The detectably effective amount of the imaging agent can vary according to factors such as the degree of susceptibility of the individual, the age, sex, and weight of the individual, idiosyncratic responses of the individual, the dosimetry, and instrument and film-related factors. Optimization of such factors is well within the level of skill in the art.

It is preferable that the compounds of the presently disclosed subject matter are excreted from tissues of the body quickly. Typically compounds of the presently disclosed subject matter are eliminated from the body in less than about 24 hours. More preferably, compounds of the presently disclosed subject matter are eliminated from the body in less than about 16 hours, 12 hours, 8 hours, 6 hours, 4 hours, 2 hours, 90 minutes, or 60 minutes.

In some embodiments, the presently disclosed methods comprise clearance of the compound comprising the imaging agent from the tumor or cell in the subject. At least one advantage of the presently disclosed methods is that, in some embodiments, there is more rapid clearance of the compound comprising the imaging agent from the kidneys than from the tumor of the subject.

In some embodiments, the presently disclosed methods use compounds that are stable in vivo such that substantially all, e.g., more than about 50%, 60%, 70%, 80%, or more preferably 90% of the injected compound is not metabolized by the body prior to excretion. In other embodiments, the compound comprising the imaging agent is stable in vivo.

C. Definitions i. Chemical Definitions

While the following terms in relation to compounds of formula (I) are believed to be well understood by one of ordinary skill in the art, the following definitions are set forth to facilitate explanation of the presently disclosed subject matter. These definitions are intended to supplement and illustrate, not preclude, the definitions that would be apparent to one of ordinary skill in the art upon review of the present disclosure.

The terms substituted, whether preceded by the term "optionally" or not, and substituent, as used herein, refer to the ability, as appreciated by one skilled in this art, to change one functional group for another functional group provided that the valency of all atoms is maintained. When more than one position in any given structure may be substituted with more than one substituent selected from a specified group, the substituent may be either the same or different at every position. The substituents also may be further substituted (e.g., an aryl group substituent may have another substituent off it, such as another aryl group, which is further substituted, for example, with fluorine at one or more positions).

Where substituent groups or linking groups are specified by their conventional chemical formulae, written from left to right, they equally encompass the chemically identical substituents that would result from writing the structure from right to left, e.g., —$CH_2O$— is equivalent to —$OCH_2$—; —C(=O)O— is equivalent to —OC(=O)—; —OC(=O)NR— is equivalent to —NRC(=O)O—, and the like.

As used herein, where an internal substituent is flanked by bonds (for example, —NRC(O)—) the order of the atoms is fixed, the orientation of the group may not be reversed, and is inserted into a structure in the orientation presented. In other words —NRC(O)— is not the same as —C(O)NR—. As used herein the term C(O) (for example —NRC(O)—) is used to indicate a carbonyl (C=O) group, where the oxygen is bonded to the carbon by a double bond.

When the term "independently selected" is used, the substituents being referred to (e.g., R groups, such as groups $R_1$, $R_2$, and the like, or variables, such as "m" and "n"), can be identical or different. For example, both $R_1$ and $R_2$ can be substituted alkyls, or $R_1$ can be hydrogen and $R_2$ can be a substituted alkyl, and the like.

The terms "a," "an," or "a(n)," when used in reference to a group of substituents herein, mean at least one. For example, where a compound is substituted with "an" alkyl or aryl, the compound is optionally substituted with at least one alkyl and/or at least one aryl. Moreover, where a moiety is substituted with an R substituent, the group may be referred to as "R-substituted." Where a moiety is R-substituted, the moiety is substituted with at least one R substituent and each R substituent is optionally different.

A named "R" or group will generally have the structure that is recognized in the art as corresponding to a group having that name, unless specified otherwise herein. For the purposes of illustration, certain representative "R" groups as set forth above are defined below.

Descriptions of compounds of the present disclosure are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

The term hydrocarbon, as used herein, refers to any chemical group comprising hydrogen and carbon. The hydrocarbon may be substituted or unsubstituted. As would be known to one skilled in this art, all valencies must be satisfied in making any substitutions. The hydrocarbon may be unsaturated, saturated, branched, unbranched, cyclic, polycyclic, or heterocyclic. Illustrative hydrocarbons are further defined herein below and include, for example, methyl, ethyl, n-propyl, iso-propyl, cyclopropyl, allyl, vinyl, n-butyl, tert-butyl, ethynyl, cyclohexyl, methoxy, diethylamino, and the like.

The term "alkyl," by itself or as part of another substituent, means, unless otherwise stated, a straight (i.e., unbranched) or branched chain, acyclic or cyclic hydrocarbon group, or combination thereof, which may be fully saturated, mono- or polyunsaturated and can include di- and multivalent groups, having the number of carbon atoms designated (i.e., $C_1$-$C_{10}$ means one to ten carbons). In particular embodiments, the term "alkyl" refers to $C_{1-20}$ inclusive, linear (i.e., "straight-chain"), branched, or cyclic, saturated or at least partially and in some cases fully unsaturated (i.e., alkenyl and alkynyl) hydrocarbon radicals derived from a hydrocarbon moiety containing between one and twenty carbon atoms by removal of a single hydrogen atom.

Representative saturated hydrocarbon groups include, but are not limited to, methyl, ethyl, n-propyl, isopropyl, n-butyl, isobutyl, sec-butyl, tert-butyl, n-pentyl, sec-pentyl, isopentyl, neopentyl, n-hexyl, sec-hexyl, n-heptyl, n-octyl, n-decyl, n-undecyl, dodecyl, cyclohexyl, (cyclohexyl)methyl, cyclopropylmethyl, and homologs and isomers thereof.

"Branched" refers to an alkyl group in which a lower alkyl group, such as methyl, ethyl or propyl, is attached to a linear alkyl chain. "Lower alkyl" refers to an alkyl group having 1 to about 8 carbon atoms (i.e., a $C_{1-8}$ alkyl), e.g., 1, 2, 3, 4, 5, 6, 7, or 8 carbon atoms. "Higher alkyl" refers to an alkyl group having about 10 to about 20 carbon atoms, e.g., 10, 11, 12, 13, 14, 15, 16, 17, 18, 19, or 20 carbon atoms. In certain embodiments, "alkyl" refers, in particular, to $C_{1-8}$ straight-chain alkyls. In other embodiments, "alkyl" refers, in particular, to $C_{1-8}$ branched-chain alkyls.

In certain embodiments, alkyl groups are $C_1$-$C_6$ alkyl groups or $C_1$-$C_4$ alkyl groups. The term "$C_1$-$C_6$ alkyl" as used herein means straight-chain, branched, or cyclic $C_1$-$C_6$ hydrocarbons which are completely saturated and hybrids thereof, such as (cycloalkyl)alkyl. Examples of $C_1$-$C_6$ alkyl substituents include methyl (Me), ethyl (Et), propyl (including n-propyl (n-Pr, $^n$Pr), iso-propyl (i-Pr, $^i$Pr), and cyclopropyl (c-Pr, $^0$Pr)), butyl (including n-butyl (n-Bu, $^n$Bu), iso-butyl (i-Bu, $^1$Bu), sec-butyl (s-Bu, $^s$Bu), tert-butyl (t-Bu, $^1$Bu), or cyclobutyl (c-Bu, $^0$Bu)), and so forth.

Alkyl groups can optionally be substituted (a "substituted alkyl") with one or more alkyl group substituents, which can be the same or different. The term "alkyl group substituent" includes but is not limited to alkyl, substituted alkyl, halo, arylamino, acyl, hydroxyl, aryloxyl, alkoxyl, alkylthio, arylthio, aralkyloxyl, aralkylthio, carboxyl, alkoxycarbonyl, oxo, and cycloalkyl. There can be optionally inserted along the alkyl chain one or more oxygen, sulfur or substituted or unsubstituted nitrogen atoms, wherein the nitrogen substituent is hydrogen, lower alkyl (also referred to herein as "alkylaminoalkyl"), or aryl.

Thus, as used herein, the term "substituted alkyl" includes alkyl groups, as defined herein, in which one or more atoms or functional groups of the alkyl group are replaced with another atom or functional group, including for example, alkyl, substituted alkyl, halogen, aryl, substituted aryl, alkoxyl, hydroxyl, nitro, amino, alkylamino, dialkylamino, sulfate, and mercapto.

The term "heteroalkyl," by itself or in combination with another term, means, unless otherwise stated, a stable straight or branched chain, or cyclic hydrocarbon group, or combinations thereof, consisting of at least one carbon atoms and at least one heteroatom selected from the group consisting of O, N, P, Si and S, and wherein the nitrogen, phosphorus, and sulfur atoms may optionally be oxidized and the nitrogen heteroatom may optionally be quaternized. The heteroatom(s) O, N, P and S and Si may be placed at any interior position of the heteroalkyl group or at the position at which alkyl group is attached to the remainder of the molecule. Examples include, but are not limited to, —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$—S(O)—CH$_3$, —CH$_2$—CH$_2$—S(O)$_2$—CH$_3$, —CH=CH—O—CH$_3$, —Si(CH$_3$)$_3$, —CH$_2$—CH=N—OCH$_3$, —CH=CH—N(CH$_3$)—CH$_3$, —O—CH$_3$, —O—CH$_2$—CH$_3$, and —CN. Up to two or three heteroatoms may be consecutive, such as, for example, —CH$_2$—NH—OCH$_3$ and —CH$_2$—O—Si(CH$_3$)$_3$.

As described above, heteroalkyl groups, as used herein, include those groups that are attached to the remainder of the molecule through a heteroatom, such as —C(O)R', —C(O)NR', —NR'R", —OR', —SR, and/or —SO$_2$R'. Where "heteroalkyl" is recited, followed by recitations of specific heteroalkyl groups, such as —NR'R or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

In the term "(cycloalkyl)alkyl", cycloalkyl, and alkyl are as defined above, and the point of attachment is on the alkyl group. This term encompasses, but is not limited to, cyclopropylmethyl, cyclopentylmethyl, and cyclohexylmethyl. The alkyl group may be substituted or unsubstituted.

"Cyclic" and "cycloalkyl" refer to a non-aromatic mono- or multicyclic ring system of about 3 to about 10 carbon atoms, e.g., 3, 4, 5, 6, 7, 8, 9, or 10 carbon atoms. The cycloalkyl group can be optionally partially unsaturated. The cycloalkyl group also can be optionally substituted with an alkyl group substituent as defined herein, oxo, and/or alkylene. There can be optionally inserted along the cyclic alkyl chain one or more oxygen, sulfur or substituted or unsubstituted nitrogen atoms, wherein the nitrogen substituent is hydrogen, alkyl, substituted alkyl, aryl, or substituted aryl, thus providing a heterocyclic group. Representative monocyclic cycloalkyl rings include cyclopropyl, cyclobutyl, cyclopentyl, cyclohexyl, and cycloheptyl.

Multicyclic cycloalkyl rings include adamantyl, octahydronaphthyl, decalin, camphor, camphane, and noradamantyl, and fused ring systems, such as dihydro- and tetrahydronaphthalene, and the like.

The terms "cycloheteroalkyl" or "heterocycloalkyl" refer to a non-aromatic ring system, unsaturated or partially unsaturated ring system, such as a 3- to 10-member substituted or unsubstituted cycloalkyl ring system, including one or more heteroatoms, which can be the same or different, and are selected from the group consisting of nitrogen (N), oxygen (O), sulfur (S), phosphorus (P), and silicon (Si), and optionally can include one or more double bonds.

The cycloheteroalkyl ring can be optionally fused to or otherwise attached to other cycloheteroalkyl rings and/or non-aromatic hydrocarbon rings. Heterocyclic rings include those having from one to three heteroatoms independently selected from oxygen, sulfur, and nitrogen, in which the nitrogen and sulfur heteroatoms may optionally be oxidized and the nitrogen heteroatom may optionally be quaternized. In certain embodiments, the term heterocylic refers to a non-aromatic 5-, 6-, or 7-membered ring or a polycyclic group wherein at least one ring atom is a heteroatom selected from 0, S, and N (wherein the nitrogen and sulfur heteroatoms may be optionally oxidized), including, but not limited to, a bi- or tri-cyclic group, comprising fused six-membered rings having between one and three heteroatoms independently selected from the oxygen, sulfur, and nitrogen, wherein (i) each 5-membered ring has 0 to 2 double bonds, each 6-membered ring has 0 to 2 double bonds, and each 7-membered ring has 0 to 3 double bonds, (ii) the nitrogen and sulfur heteroatoms may be optionally oxidized, (iii) the nitrogen heteroatom may optionally be quaternized, and (iv) any of the above heterocyclic rings may be fused to an aryl or heteroaryl ring. Representative cycloheteroalkyl ring systems include, but are not limited to pyrrolidinyl, pyrrolinyl, imidazolidinyl, imidazolinyl, pyrazolidinyl, pyrazolinyl, piperidyl, piperazinyl, indolinyl, quinuclidinyl, morpholinyl, thiomorpholinyl, thiadiazinanyl, tetrahydrofuranyl, and the like.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. The terms "cycloalkylene" and "heterocycloalkylene" refer to the divalent derivatives of cycloalkyl and heterocycloalkyl, respectively.

The term "cycloalkylalkyl," as used herein, refers to a cycloalkyl group as defined hereinabove, which is attached to the parent molecular moiety through an alkyl group, also as defined above. Examples of cycloalkylalkyl groups include cyclopropylmethyl and cyclopentylethyl.

An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1, 4-pentadienyl), ethynyl, 1- and 3-propynyl, 3-butynyl, and the higher homologs and isomers. Alkyl groups which are limited to hydrocarbon groups are termed "homoalkyl."

More particularly, the term "alkenyl" as used herein refers to a monovalent group derived from a $C_{1-20}$ inclusive straight or branched hydrocarbon moiety having at least one carbon-carbon double bond by the removal of a single hydrogen atom. Alkenyl groups include, for example, ethenyl (i.e., vinyl), propenyl, butenyl, 1-methyl-2-buten-1-yl, pentenyl, hexenyl, octenyl, and butadienyl.

The term "cycloalkenyl" as used herein refers to a cyclic hydrocarbon containing at least one carbon-carbon double bond. Examples of cycloalkenyl groups include cyclopropenyl, cyclobutenyl, cyclopentenyl, cyclopentadiene, cyclohexenyl, 1,3-cyclohexadiene, cycloheptenyl, cycloheptatrienyl, and cyclooctenyl.

The term "alkynyl" as used herein refers to a monovalent group derived from a straight or branched $C_{1-20}$ hydrocarbon of a designed number of carbon atoms containing at least one carbon-carbon triple bond. Examples of "alkynyl" include ethynyl, 2-propynyl (propargyl), 1-propynyl, pentynyl, hexynyl, heptynyl, and allenyl groups, and the like.

The term "alkylene" by itself or a part of another substituent refers to a straight or branched bivalent aliphatic hydrocarbon group derived from an alkyl group having from 1 to about 20 carbon atoms, e.g., 1, 2, 3, 4, 5, 6, 7, 8, 9, 10, 11, 12, 13, 14, 15, 16, 17, 18, 19, or 20 carbon atoms. The alkylene group can be straight, branched or cyclic. The alkylene group also can be optionally unsaturated and/or substituted with one or more "alkyl group substituents." There can be optionally inserted along the alkylene group one or more oxygen, sulfur or substituted or unsubstituted nitrogen atoms (also referred to herein as "alkylaminoalkyl"), wherein the nitrogen substituent is alkyl as previously described. Exemplary alkylene groups include methylene (—$CH_2$—); ethylene (—$CH_2$—$CH_2$—); propylene (—$(CH_2)_3$—); cyclohexylene (—$C_6H_{10}$); CH=CH—CH=CH—; —CH=CH—$CH_2$—; —$CH_2CH_2CH_2CH_2$—, —$CH_2$CH=CHCH$_2$—, —$CH_2$CsCCH$_2$—, —$CH_2CH_2$CH($CH_2CH_2CH_3$)$CH_2$—, —$(CH_2)_q$—N(R)—$(CH_2)_r$—, wherein each of q and r is independently an integer from 0 to about 20, e.g., 0, 1, 2, 3, 4, 5, 6, 7, 8, 9, 10, 11, 12, 13, 14, 15, 16, 17, 18, 19, or 20, and R is hydrogen or lower alkyl; methylenedioxyl (—O—$CH_2$—O—); and ethylenedioxyl (—O—$(CH_2)_2$—O—). An alkylene group can have about 2 to about 3 carbon atoms and can further have 6-20 carbons. Typically, an alkyl (or alkylene) group will have from 1 to 24 carbon atoms, with those groups having 10 or fewer carbon atoms being some embodiments of the present disclosure. A "lower alkyl" or "lower alkylene" is a shorter chain alkyl or alkylene group, generally having eight or fewer carbon atoms.

The term "heteroalkylene" by itself or as part of another substituent means a divalent group derived from heteroalkyl, as exemplified, but not limited by, —$CH_2$—$CH_2$—S—$CH_2$—$CH_2$— and —$CH_2$—S—$CH_2$—$CH_2$—NH—$CH_2$—. For heteroalkylene groups, heteroatoms can also occupy either or both of the chain termini (e.g., alkyleneoxo, alkylenedioxo, alkyleneamino, alkylenediamino, and the like). Still further, for alkylene and heteroalkylene linking groups, no orientation of the linking group is implied by the direction in which the formula of the linking group is written. For example, the formula —C(O)OR'— represents both —C(O)OR'— and —R'OC(O)—.

The term "aryl" means, unless otherwise stated, an aromatic hydrocarbon substituent that can be a single ring or multiple rings (such as from 1 to 3 rings), which are fused together or linked covalently.

The term "heteroaryl" refers to aryl groups (or rings) that contain from one to four heteroatoms (in each separate ring in the case of multiple rings) selected from N, O, and S, wherein the nitrogen and sulfur atoms are optionally oxidized, and the nitrogen atom(s) are optionally quaternized. A heteroaryl group can be attached to the remainder of the molecule through a carbon or heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, indazolyl, 1-isoquinolyl, 5-isoquinolyl, 2-quinoxalinyl, 5-quinoxalinyl, 3-quinolyl, and 6-quinolyl. Substituents for each of above noted aryl and heteroaryl ring systems are selected from the group of acceptable substituents described below. The terms "arylene" and "heteroarylene" refer to the divalent forms of aryl and heteroaryl, respectively.

For brevity, the term "aryl" when used in combination with other terms (e.g., aryloxo, arylthioxo, arylalkyl) includes both aryl and heteroaryl rings as defined above. Thus, the terms "arylalkyl" and "heteroarylalkyl" are meant to include those groups in which an aryl or heteroaryl group is attached to an alkyl group (e.g., benzyl, phenethyl, pyridylmethyl, furylmethyl, and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like). The term "haloaryl," however, as used herein, is meant to cover only aryls substituted with one or more halogens.

Where a heteroalkyl, heterocycloalkyl, or heteroaryl includes a specific number of members (e.g. "3 to 7 membered"), the term "member" refers to a carbon or heteroatom.

As used herein, the term "alkylaryl" includes alkyl groups, as defined above, substituted by aryl groups, as defined above. The aryl group may be connected at any point on the alkyl group. The term $C_4$-$C_{16}$ alkylaryl includes alkylaryl groups having a total of 4 to 16 carbon atoms, counting the carbon atoms on the alkyl group and aryl group together. Examples of alkylaryl groups include but are not limited to benzyl (phenylmethyl), phenyl ethyl, and naphthylmethyl. The alkylaryl group may be substituted or unsubstituted. Substituents are not counted towards the total number of atoms in the alkylaryl group, so long as the total atoms in the substituent(s) are not larger than the alkylaryl group.

Further, a structure represented generally by the formula:

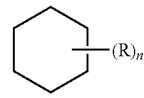

as used herein refers to a ring structure, for example, but not limited to a 3-carbon, a 4-carbon, a 5-carbon, a 6-carbon, a 7-carbon, and the like, aliphatic and/or aromatic cyclic compound, including a saturated ring structure, a partially saturated ring structure, and an unsaturated ring structure, comprising a substituent R group, wherein the R group can be present or absent, and when present, one or more R groups can each be substituted on one or more available carbon atoms of the ring structure. The presence or absence of the R group and number of R groups is determined by the value of the variable "n," which is an integer generally having a value ranging from 0 to the number of carbon atoms on the ring available for substitution. Each R group, if more than one, is substituted on an available carbon of the ring structure rather than on another R group. For example, the structure above where n is 0 to 2 would comprise compound groups including, but not limited to:

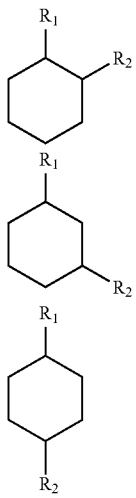

and the like.

A dashed line representing a bond in a cyclic ring structure indicates that the bond can be either present or absent in the ring. That is, a dashed line representing a bond in a cyclic ring structure indicates that the ring structure is selected from the group consisting of a saturated ring structure, a partially saturated ring structure, and an unsaturated ring structure.

A substituent bearing a broken bond, such as the example shown below, means that the substituent is directly bonded to the molecule at the indicated position. No additional methylene (CH$_2$) groups are implied. The symbol ( ～～～ ) denotes the point of attachment of a moiety to the remainder of the molecule.

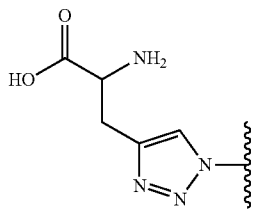 [SMILES: *n1cc(CC(N)C(=O)O)nn1]

Substituents bearing two broken bonds, such as the example shown below, means that the orientation of the atoms is as-indicated, left to right and should be inserted into a molecule in the orientation shown. No additional methylene (CH$_2$) groups are implied unless specifically indicated.

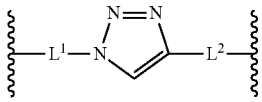

When a named atom of an aromatic ring or a heterocyclic aromatic ring is defined as being "absent," the named atom is replaced by a direct bond.

Each of above terms (e.g., "alkyl," "heteroalkyl," "cycloalkyl, and "heterocycloalkyl", "aryl," "heteroaryl," "phosphonate," and "sulfonate" as well as their divalent derivatives) are meant to include both substituted and unsubstituted forms of the indicated group. Optional substituents for each type of group are provided below.

Substituents for alkyl, heteroalkyl, cycloalkyl, heterocycloalkyl monovalent and divalent derivative groups (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to: —OR', =O, =NR', =N—OR', —NR'R", —SR', -halogen, —SiR'R"R'", —OC(O)R', —C(O)R', —CO$_2$R', —C(O)NR'R", —OC(O)NR'R", —NR"C(O)R', —NR'—C(O)NR"R'", —NR"C(O)OR', —NR—C(NR'R")=NR"', —S(O)R', —S(O)$_2$R', —S(O)$_2$NR'R", —NRSO$_2$R', —CN and —NO$_2$ in a number ranging from zero to (2m'+1), where m' is the total number of carbon atoms in such groups. R', R", R'" and R"" each may independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted alkyl, alkoxy or thioalkoxy groups, or arylalkyl groups. As used herein, an "alkoxy" group is an alkyl attached to the remainder of the molecule through a divalent oxygen. When a compound of the disclosure includes more than one R group, for example, each of the R groups is independently selected as are each R', R", R'" and R"" groups when more than one of these groups is present. When R' and R" are attached to the same nitrogen atom, they can be combined with the nitrogen atom to form a 4-, 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for alkyl groups above, exemplary substituents for aryl and heteroaryl groups (as well as their divalent derivatives) are varied and are selected from, for example: halogen, —OR', —NR'R", —SR', -halogen, —SiR'R"R'", —OC(O)R', —C(O)R', —CO$_2$R', —C(O)NR'R", —OC(O)NR'R", —NR"C(O)R', —NR'—C(O)NR"R'", —NR"C(O)OR', —NR—C(NR'R"R'")=NR"", —NR—C(NR'R")=NR'"—S(O)R', —S(O)$_2$R', —S(O)$_2$NR'R", —NRSO$_2$R', —CN and —NO$_2$, —R', —N$_3$, —CH(Ph)$_2$, fluoro(C$_1$-C$_4$)alkoxo, and fluoro (C$_1$-C$_4$)alkyl, in a number ranging from zero to the total number of open valences on aromatic ring system; and where R', R", R'" and R"" may be independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl. When a compound of the disclosure includes more than one R group, for example, each of the R groups is independently selected as are each R', R", R'" and R"" groups when more than one of these groups is present.

Two of the substituents on adjacent atoms of aryl or heteroaryl ring may optionally form a ring of the formula -T-C(O)—(CRR')$_q$—U—, wherein T and U are independently —NR—, —O—, —CRR'— or a single bond, and q is an integer of from 0 to 3. Alternatively, two of the substituents on adjacent atoms of aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'— or a single bond, and r is an integer of from 1 to 4.

One of the single bonds of the new ring so formed may optionally be replaced with a double bond. Alternatively, two of the substituents on adjacent atoms of aryl or heteroaryl ring may optionally be replaced with a substituent of the formula —(CRR')$_s$—X'—(C"R''')$_d$—, where s and d are independently integers of from 0 to 3, and X' is —O—, —NR'—, —S—, —S(O)—, —S(O)$_2$—, or —S(O)$_2$NR'—. The substituents R, R', R" and R''' may be independently selected from hydrogen, substituted or unsubstituted alkyl, substituted or unsubstituted cycloalkyl, substituted or unsubstituted heterocycloalkyl, substituted or unsubstituted aryl, and substituted or unsubstituted heteroaryl.

As used herein, the term "acyl" refers to an organic acid group wherein the —OH of the carboxyl group has been replaced with another substituent and has the general formula RC(=O)—, wherein R is an alkyl, alkenyl, alkynyl, aryl, carbocylic, heterocyclic, or aromatic heterocyclic group as defined herein). As such, the term "acyl" specifically includes arylacyl groups, such as an acetylfuran and a phenacyl group. Specific examples of acyl groups include acetyl and benzoyl.

The terms "alkoxyl" or "alkoxy" are used interchangeably herein and refer to a saturated (i.e., alkyl-O—) or unsaturated (i.e., alkenyl-O— and alkynyl-O—) group attached to the parent molecular moiety through an oxygen atom, wherein the terms "alkyl," "alkenyl," and "alkynyl" are as previously described and can include C$_{1-20}$ inclusive, linear, branched, or cyclic, saturated or unsaturated oxo-hydrocarbon chains, including, for example, methoxyl, ethoxyl, propoxyl, isopropoxyl, n-butoxyl, sec-butoxyl, t-butoxyl, and n-pentoxyl, neopentoxyl, n-hexoxyl, and the like.

The term "alkoxyalkyl" as used herein refers to an alkyl-O-alkyl ether, for example, a methoxyethyl or an ethoxymethyl group.

"Aryloxyl" refers to an aryl-O— group wherein the aryl group is as previously described, including a substituted aryl. The term "aryloxyl" as used herein can refer to phenyloxyl or hexyloxyl, and alkyl, substituted alkyl, halo, or alkoxyl substituted phenyloxyl or hexyloxyl.

"Aralkyl" refers to an aryl-alkyl-group wherein aryl and alkyl are as previously described, and included substituted aryl and substituted alkyl. Exemplary aralkyl groups include benzyl, phenylethyl, and naphthylmethyl.

"Aralkyloxyl" refers to an aralkyl-O— group wherein the aralkyl group is as previously described. An exemplary aralkyloxyl group is benzyloxyl.

"Alkoxycarbonyl" refers to an alkyl-O—CO— group. Exemplary alkoxycarbonyl groups include methoxycarbonyl, ethoxycarbonyl, butyloxycarbonyl, and t-butyloxycarbonyl.

"Aryloxycarbonyl" refers to an aryl-O—CO— group. Exemplary aryloxycarbonyl groups include phenoxy- and naphthoxy-carbonyl.

"Aralkoxycarbonyl" refers to an aralkyl-O—CO— group. An exemplary aralkoxycarbonyl group is benzyloxycarbonyl.

"Carbamoyl" refers to an amide group of the formula —CONH$_2$.

"Alkylcarbamoyl" refers to a R'RN—CO— group wherein one of R and R' is hydrogen and the other of R and R' is alkyl and/or substituted alkyl as previously described. "Dialkylcarbamoyl" refers to a R'RN—CO— group wherein each of R and R' is independently alkyl and/or substituted alkyl as previously described.

The term carbonyldioxyl, as used herein, refers to a carbonate group of the formula —O—CO—OR.

"Acyloxyl" refers to an acyl-O— group wherein acyl is as previously described.

The term "amino" refers to the —NH$_2$ group and also refers to a nitrogen containing group as is known in the art derived from ammonia by the replacement of one or more hydrogen radicals by organic radicals. For example, the terms "acylamino" and "alkylamino" refer to specific N-substituted organic radicals with acyl and alkyl substituent groups respectively.

An "aminoalkyl" as used herein refers to an amino group covalently bound to an alkylene linker. More particularly, the terms alkylamino, dialkylamino, and trialkylamino as used herein refer to one, two, or three, respectively, alkyl groups, as previously defined, attached to the parent molecular moiety through a nitrogen atom. The term alkylamino refers to a group having the structure —NHR' wherein R' is an alkyl group, as previously defined; whereas the term dialkylamino refers to a group having the structure —NR'R", wherein R' and R" are each independently selected from the group consisting of alkyl groups. The term trialkylamino refers to a group having the structure NR'R"R''', wherein R', R", and R''' are each independently selected from the group consisting of alkyl groups. Additionally, R', R", and/or R''' taken together may optionally be —(CH$_2$)$_k$— where k is an integer from 2 to 6. Examples include, but are not limited to, methylamino, dimethylamino, ethylamino, diethylamino, diethylaminocarbonyl, methylethylamino, iso-propylamino, piperidino, trimethylamino, and propylamino.

The amino group is —NR'R", wherein R' and R" are typically selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

The terms alkylthioether and thioalkoxyl refer to a saturated (i.e., alkyl-S—) or unsaturated (i.e., alkenyl-S— and alkynyl-S—) group attached to the parent molecular moiety through a sulfur atom. Examples of thioalkoxyl moieties include, but are not limited to, methylthio, ethylthio, propylthio, isopropylthio, n-butylthio, and the like.

"Acylamino" refers to an acyl-NH— group wherein acyl is as previously described. "Aroylamino" refers to an aroyl-NH— group wherein aroyl is as previously described.

The term "carbonyl" refers to the —(C=O)— group.

The term "carboxyl" refers to the —COOH group. Such groups also are referred to herein as a "carboxylic acid" moiety.

The terms "halo," "halide," or "halogen" as used herein refer to fluoro, chloro, bromo, and iodo groups. Additionally, terms such as "haloalkyl," are meant to include monohaloalkyl and polyhaloalkyl. For example, the term "halo(C$_1$-C$_4$)alkyl" is mean to include, but not be limited to, trifluoromethyl, 2,2,2-trifluoroethyl, 4-chlorobutyl, 3-bromopropyl, and the like.

The term "hydroxyl" refers to the —OH group.

The term "hydroxyalkyl" refers to an alkyl group substituted with an —OH group.

The term "mercapto" refers to the —SH group.

The term "oxo" as used herein means an oxygen atom that is double bonded to a carbon atom or to another element.

The term "nitro" refers to the —NO$_2$ group.

The term "thio" refers to a compound described previously herein wherein a carbon or oxygen atom is replaced by a sulfur atom.

The term "sulfate" refers to the —SO$_4$ group.

The term thiohydroxyl or thiol, as used herein, refers to a group of the formula —SH.

The term ureido refers to a urea group of the formula —NH—CO—NH$_2$.

Unless otherwise explicitly defined, a "substituent group," as used herein, includes a functional group selected from one or more of the following moieties, which are defined herein:

(A) —OH, —NH$_2$, —SH, —CN, —CF$_3$, —NO$_2$, oxo, halogen, unsubstituted alkyl, unsubstituted heteroalkyl, unsubstituted cycloalkyl, unsubstituted heterocycloalkyl, unsubstituted aryl, unsubstituted heteroaryl, and (B) alkyl, heteroalkyl, cycloalkyl, heterocycloalkyl, aryl, and heteroaryl, substituted with at least one substituent selected from:

(i) oxo, —OH, —NH$_2$, —SH, —CN, —CF$_3$, —NO$_2$, halogen, unsubstituted alkyl, unsubstituted heteroalkyl, unsubstituted cycloalkyl, unsubstituted heterocycloalkyl, unsubstituted aryl, unsubstituted heteroaryl, and (ii) alkyl, heteroalkyl, cycloalkyl, heterocycloalkyl, aryl, and heteroaryl, substituted with at least one substituent selected from:

(a) oxo, —OH, —NH$_2$, —SH, —CN, —CF$_3$, —NO$_2$, halogen, unsubstituted alkyl, unsubstituted heteroalkyl, unsubstituted cycloalkyl, unsubstituted heterocycloalkyl, unsubstituted aryl, unsubstituted heteroaryl, and (b) alkyl, heteroalkyl, cycloalkyl, heterocycloalkyl, aryl, or heteroaryl, substituted with at least one substituent selected from oxo, —OH, —NH$_2$, —SH, —CN, —CF$_3$, —NO$_2$, halogen, unsubstituted alkyl, unsubstituted heteroalkyl, unsubstituted cycloalkyl, unsubstituted heterocycloalkyl, unsubstituted aryl, and unsubstituted heteroaryl.

A "lower substituent" or "lower substituent group," as used herein means a group selected from all of the substituents described hereinabove for a "substituent group," wherein each substituted or unsubstituted alkyl is a substituted or unsubstituted C$_1$-C$_8$ alkyl, each substituted or unsubstituted heteroalkyl is a substituted or unsubstituted 2 to 8 membered heteroalkyl, each substituted or unsubstituted cycloalkyl is a substituted or unsubstituted C$_5$-C$_7$ cycloalkyl, and each substituted or unsubstituted heterocycloalkyl is a substituted or unsubstituted 5 to 7 membered heterocycloalkyl.

A "size-limited substituent" or "size-limited substituent group," as used herein means a group selected from all of the substituents described above for a "substituent group," wherein each substituted or unsubstituted alkyl is a substituted or unsubstituted C$_1$-C$_{20}$ alkyl, each substituted or unsubstituted heteroalkyl is a substituted or unsubstituted 2 to 20 membered heteroalkyl, each substituted or unsubstituted cycloalkyl is a substituted or unsubstituted C$_4$-C$_8$ cycloalkyl, and each substituted or unsubstituted heterocycloalkyl is a substituted or unsubstituted 4 to 8 membered heterocycloalkyl.

Throughout the specification and claims, a given chemical formula or name shall encompass all tautomers, congeners, and optical- and stereoisomers, as well as racemic mixtures where such isomers and mixtures exist.

It will be apparent to one skilled in the art that certain compounds of this disclosure may exist in tautomeric forms, all such tautomeric forms of the compounds being within the scope of the disclosure. The term "tautomer," as used herein, refers to one of two or more structural isomers which exist in equilibrium and which are readily converted from one isomeric form to another.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the disclosure.

Certain compounds of the present disclosure possess asymmetric carbon atoms (optical or chiral centers) or double bonds; the enantiomers, racemates, diastereomers, tautomers, geometric isomers, stereoisometric forms that may be defined, in terms of absolute stereochemistry, as (R)- or (S)- or, as (D)- or (L)- for amino acids, and individual isomers are encompassed within the scope of the present disclosure. The compounds of the present disclosure do not include those which are known in art to be too unstable to synthesize and/or isolate. The present disclosure is meant to include compounds in racemic and optically pure forms. Optically active (R)- and (S)-, or (D)- and (L)-isomers may be prepared using chiral synthons or chiral reagents, or resolved using conventional techniques. When the compounds described herein contain olefenic bonds or other centers of geometric asymmetry, and unless specified otherwise, it is intended that the compounds include both E and Z geometric isomers.

It is well known in the art how to prepare optically active forms, such as by resolution of racemic forms (racemates), by asymmetric synthesis, or by synthesis from optically active starting materials. Resolution of the racemates can be accomplished, for example, by conventional methods such as crystallization in the presence of a resolving agent, or chromatography, using, for example a chiral HPLC column. Many geometric isomers of olefins, C=N double bonds, and the like also can be present in the compounds described herein, and all such stable isomers are contemplated in the presently disclosed subject matter. Cis and trans geometric isomers of the compounds of the presently disclosed subject matter are described and may be isolated as a mixture of isomers or as separated isomeric forms. All chiral (enantiomeric and diastereomeric), and racemic forms, as well as all geometric isomeric forms of a structure are intended, unless the specific stereochemistry or isomeric form is specifically indicated.

The compounds herein described may have one or more charged atoms. For example, the compounds may be zwitterionic, but may be neutral overall. Other embodiments may have one or more charged groups, depending on the pH and other factors. In these embodiments, the compound may be associated with a suitable counter-ion. It is well known in the art how to prepare salts or exchange counter-ions. Generally, such salts can be prepared by reacting free acid forms of these compounds with a stoichiometric amount of the appropriate base (such as Na, Ca, Mg, or K hydroxide, carbonate, bicarbonate, or the like), or by reacting free base forms of these compounds with a stoichiometric amount of the appropriate acid. Such reactions are typically carried out in water or in an organic solvent, or in a mixture of the two. Counter-ions may be changed, for example, by ion-exchange techniques such as ion-exchange chromatography. All zwitterions, salts and counter-ions are intended, unless the counter-ion or salt is specifically indicated. In certain embodiments, the salt or counter-ion may be pharmaceutically acceptable, for administration to a subject. Pharmaceutically acceptable salts are discussed later.

As used herein, a "protecting group" is a chemical substituent which can be selectively removed by readily available reagents which do not attack the regenerated functional group or other functional groups in the molecule. Suitable protecting groups are known in the art and continue to be developed. Suitable protecting groups may be found, for example in Wutz et al. ("Greene's Protective Groups in Organic Synthesis, Fourth Edition," Wiley-Interscience, 2007). Protecting groups for protection of the carboxyl group, as described by Wutz et al. (pages 533-643), are used in certain embodiments. In some embodiments, the protecting group is removable by treatment with acid. Specific examples of protecting groups include but are not limited to, benzyl, p-methoxybenzyl (PMB), tertiary butyl ($^t$Bu), methoxymethyl (MOM), methoxyethoxymethyl (MEM), methylthiomethyl (MTM), tetrahydropyranyl (THP), tetrahydrofuranyl (THF), benzyloxymethyl (BOM), trimethylsilyl (TMS), triethylsilyl (TES), t-butyldimethylsilyl (TBDMS), and triphenylmethyl (trityl, Tr). Persons skilled in the art will recognize appropriate situations in which protecting groups are required and will be able to select an appropriate protecting group for use in a particular circumstance.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}$C- or $^{14}$C-enriched carbon are within the scope of this disclosure.

The compounds of the present disclosure may also contain unnatural proportions of atomic isotopes at one or more of atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the present disclosure, whether radioactive or not, are encompassed within the scope of the present disclosure.

ii. Pharmaceutical Salts

The compounds of the present disclosure may exist as pharmaceutically acceptable salts. The term "pharmaceutically acceptable salts" is meant to include salts of active compounds which are prepared with relatively nontoxic acids or bases, depending on the particular substituent moieties found on the compounds described herein. Pharmaceutically acceptable salts are generally well known to those of ordinary skill in the art, and may include, by way of example but not limitation, acetate, benzenesulfonate, besylate, benzoate, bicarbonate, bitartrate, bromide, calcium edetate, carnsylate, carbonate, citrate, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isethionate, lactate, lactobionate, malate, maleate, mandelate, mesylate, mucate, napsylate, nitrate, pamoate (embonate), pantothenate, phosphate/diphosphate, polygalacturonate, salicylate, stearate, subacetate, succinate, sulfate, tannate, tartrates, (e.g. (+)-tartrates, (−)-tartrates or mixtures thereof including racemic mixtures), or teoclate. These salts may be prepared by methods known to those skilled in art. Other pharmaceutically acceptable salts may be found in, for example, Remington: The Science and Practice of Pharmacy (20$^{th}$ ed.) Lippincott, Williams & Wilkins (2000).

Also included are base addition salts such as sodium, potassium, calcium, ammonium, organic amino, or magnesium salt, or a similar salt. When compounds of the present disclosure contain relatively basic functionalities, acid addition salts can be obtained by contacting the neutral form of such compounds with a sufficient amount of the desired acid, either neat or in a suitable inert solvent. Examples of acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like.

Also included are salts of amino acids such as arginate and the like, and salts of organic acids like glucuronic or galactunoric acids and the like, see, for example, Berge et al, "Pharmaceutical Salts", Journal of Pharmaceutical Science, 1977, 66, 1-19). Certain specific compounds of the present disclosure contain both basic and acidic functionalities that allow the compounds to be converted into either base or acid addition salts. The neutral forms of the compounds may be regenerated by contacting the salt with a base or acid and isolating the parent compound in the conventional manner. The parent form of the compound differs from the various salt forms in certain physical properties, such as solubility in polar solvents.

Certain compounds of the present disclosure can exist in unsolvated forms as well as solvated forms, including hydrated forms. In general, the solvated forms are equivalent to unsolvated forms and are encompassed within the scope of the present disclosure. Certain compounds of the present disclosure may exist in multiple crystalline or amorphous forms. In general, all physical forms are equivalent for the uses contemplated by the present disclosure and are intended to be within the scope of the present disclosure.

iii. General Definitions

Although specific terms are employed herein, they are used in a generic and descriptive sense only and not for purposes of limitation. Particular definitions are provided herein for clarity. Unless otherwise defined, all technical and scientific terms used herein have the same meaning as commonly understood by one of ordinary skill in the art to which this presently described subject matter belongs.

A "cancer" in an animal refers to the presence of cells possessing characteristics typical of cancer-causing cells, for example, uncontrolled proliferation, loss of specialized functions, immortality, significant metastatic potential, significant increase in anti-apoptotic activity, rapid growth and proliferation rate, and certain characteristic morphology and cellular markers. In some circumstances, cancer cells will be in the form of a tumor; such cells may exist locally within an animal, or circulate in the blood stream as independent cells.

By "control" is meant a standard or reference condition.

By "disease" is meant any condition or disorder that damages or interferes with the normal function of a cell, tissue, organ, organism, or subject.

An "effective amount" of an agent refers to the amount of the agent sufficient to elicit a desired biological response or a measureable difference when compared to a control. As will be appreciated by one of ordinary skill in the art, the absolute amount of a particular agent that is effective for treating a disease, disorder, condition, or injury can vary depending on such factors as the agent to be delivered, the manner of administration, the age, body weight, and general health of the subject, the desired biological endpoint, the desired therapeutic effect, and the like. Ultimately, an attending clinician will decide the appropriate amount and dosage regimen. For example, an "effective amount" of an agent can be an amount sufficient to produce a measurable image when the compound is used for imaging, or an amount sufficient to ameliorate the symptoms of a disease when the compound is used for therapy. One of ordinary skill in the art will further understand that an effective amount of an agent can be administered in a single dose, or can be achieved by administration of multiple doses.

The term "administering" as used herein refers to contacting a subject with a presently disclosed agent.

Following long-standing patent law convention, the terms "a," "an," and "the" refer to "one or more" when used in this application, including the claims. Thus, for example, reference to "a subject" includes a plurality of subjects, unless the context clearly is to the contrary (e.g., a plurality of subjects), and so forth.

Throughout this specification and the claims, the terms "comprise," "comprises," and "comprising" are used in a non-exclusive sense, except where the context requires otherwise. Likewise, the term "include" and its grammatical variants are intended to be non-limiting, such that recitation of items in a list is not to the exclusion of other like items that can be substituted or added to the listed items.

For the purposes of this specification and appended claims, unless otherwise indicated, all numbers expressing amounts, sizes, dimensions, proportions, shapes, formulations, parameters, percentages, parameters, quantities, characteristics, and other numerical values used in the specification and claims, are to be understood as being modified in all instances by the term "about" even though the term "about" may not expressly appear with the value, amount or range. Accordingly, unless indicated to the contrary, the numerical parameters set forth in the following specification and attached claims are not and need not be exact, but may be approximate and/or larger or smaller as desired, reflecting tolerances, conversion factors, rounding off, measurement error and the like, and other factors known to those of skill in the art depending on the desired properties sought to be obtained by the presently disclosed subject matter. For example, the term "about," when referring to a value can be meant to encompass variations of, in some embodiments, ±100% in some embodiments ±50%, in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods or employ the disclosed compositions.

Further, the term "about" when used in connection with one or more numbers or numerical ranges, should be understood to refer to all such numbers, including all numbers in a range and modifies that range by extending the boundaries above and below the numerical values set forth. The recitation of numerical ranges by endpoints includes all numbers, e.g., whole integers, including fractions thereof, subsumed within that range (for example, the recitation of 1 to 5 includes 1, 2, 3, 4, and 5, as well as fractions thereof, e.g., 1.5, 2.25, 3.75, 4.1, and the like) and any range within that range.

EXAMPLES

The following Examples have been included to provide guidance to one of ordinary skill in the art for practicing representative embodiments of the presently disclosed subject matter. In light of the present disclosure and the general level of skill in the art, those of skill can appreciate that the following Examples are intended to be exemplary only and that numerous changes, modifications, and alterations can be employed without departing from the scope of the presently disclosed subject matter. The synthetic descriptions and specific examples that follow are only intended for the purposes of illustration, and are not to be construed as limiting in any manner to make compounds of the disclosure by other methods.

Example 1

Synthesis and Evaluation of Gadolinium (Gd)-Based Contrast Agents

Overview

Magnetic resonance (MR) imaging is advantageous because it can provide anatomic, functional and molecular information concurrently. MR molecular imaging can combine the ubiquity of this established clinical modality and its high spatial resolution with molecular profiling in vivo. However, due to the intrinsically low sensitivity of MR, high local concentrations of biological targets are required to generate discernable MR contrast. We hypothesize that the prostate-specific membrane antigen (PSMA), an attractive target for imaging and therapy of prostate cancer, could serve as a suitable biomarker for MR-based molecular imaging because of its high concentration within target cells, limited expression in non-target tissues and accessibility on the cell surface. For this purpose, three high-affinity, low-molecular-weight gadolinium(Gd)(III)-based PSMA-targeted contrast agents graded with one to three Gd-chelates per molecule Gd1, Gd2 and Gd3, respectively (FIG. 1A) have been synthesized. The aim of this study was to evaluate the PSMA binding affinities and longitudinal relaxivity ($r_1$) of the synthesized agents. Cellular uptake of the agents in PSMA-expressing cells isogenic, non-expressing control cells was evaluated using inductively coupled plasma mass spectrometry (ICP-MS). Finally the ability of the agents to distinguish PSMA-expressing cells from control cells was evaluated both in vitro and in vivo by MR imaging.

Materials and Methods (21S,25S)-8,15,23-trioxo-1-((4-((1,4,7,10-tetrakis (carboxymethyl)-1,4,7,10-tetraazacyclododecan-2-yl)methyl)phenyl)amino)-1-thioxo-2,7,16,22,24-pentaazaheptacosane-21,25,27-tricarboxylic acid, Gd1

Compound Gd1 was prepared following a recent report. Compound 1 was prepared in three steps as described below. Commercially available N-Boc-1,4 diaminobutane (68 mg, 0.36 mmol in 0.5 ml DMSO) was mixed with 1,4,7,10-Tetraazacyclododecane-1,4,7,10-tetraacetic acid, 2-[(4-isothiocyanatophenyl)methyl] (pSCN-Bn-DOTA) (192 mg, 0.28 mmol in 2.5 mL DMSO) and DIEA (132 µl, 0.75 mmol) and stirred at 40° C. for 4 h. The solvent was evaporated and the solid residue was purified by reverse phase $C_{18}$ flash chromatography (5.5 g, Agilent SF10) using water and acetonitrile (0.1% TFA in each) to obtain Boc-protected 7 after lyophilization. Yield: 146 mg, ~55%. ESI-MS 740 [M+H]$^+$. The compound resulting from that step was then treated with ice-cold TFA/CH$_2$Cl$_2$ (1/1) solution and left stirring at ambient temperature for 2 h. The solvent was evaporated and the residue was dried under vacuum and purified by reverse phase flash chromatography (5.5 g, Agilent SF10) to produce 7 in moderate yield. The solvent was evaporated and the residue was dried under vacuum and purified by reverse phase flash chromatography (5.5 g, Agilent SF10) to produce 7. Yield ~104 mg, 40%. $^1$H NMR (DMSO-d$_6$) δ: 8.80-8.64 (m, 1H), 8.12-7.90 (m, 2H), 7.75-7.10 (bm, 4H), 4.65-4.63 (m, 1H), 4.17-2.59 (m, 27H), 2.40-1.11 (m, 6H). ESI-MS: 640 [M+1]$^+$. A solution of 7 (110 mg, 0.17 mmol in 3 mL distilled water) was added to a solution Gd$_2$(CO$_3$)$_3$ (85 mg, 0.17 mmol) and left stirring 60° C. for 14 h. ESI-MS: Calcd. for C$_{48}$H$_{77}$N$_{10}$O$_{17}$S, 797.5183 [M+H]$^+$. found: 797.5212. Compound was then purified by HPLC. Method 1: solvent A (0.1% TFA in water) and solvent B (0.1% TFA in acetonitrile), flow rate 8 mL/min. The elution gradient was 100% A and 0% B for 5 min and 100% A to 80% A and 0% B to 20% B over 5-25 min, and 80% A to 20% A and 20% B to 80% B from 25-30 min.

(30S,34S)-2,9,17,24,32-pentaoxo-1-(4,7,10-tris(carboxymethyl)-1,4,7,10-tetraazacyclododecan-1-yl)-8-(2-(4,7,10-tris(carboxymethyl)-1,4,7,10-tetraazacyclododecan-1-yl)acetamido)-3,10,16,25,31,33-hexaazahexatriacontane-11,30,34,36-tetracarboxylic acid, digadolinium(III) salt. Gd2

The compound was prepared by following Scheme 2. To a solution of N-Bis-Boc-L-Lysine NHS (3 gm, 6.7 mmol in 10 mL DMF) was added Fmoc-Lys(Boc)-OH (2.49 g, 6.7 mmol) and the solution was sonicated at rt for 1 hr until a clear solution was obtained. The solution was the stirred for 4 h at rt and solvent was removed under vacuum to obtain 4 in nearly quantitative yield. The compound 4 was further purified by silica gel column using 3/97 MeOH/CH$_2$Cl$_2$ as an eluent). $^1$H NMR (CDCl$_3$) δ: 8.01 (d, 2H), 7.89 (m, 2H), 7.78-7.44 (m, 4H), 6.82 (m, 1H), 6.15 (m, 1H), 5.58 (m, 1H), 5.01-4.03 (m, 5H), 3.75-3.32 (m, 6H), 2.22-1.31 (m, 30H). ESMS m/Z: 696 [M+H]$^+$. Compound 4 (2 g, 2.9 mmol) was dissolved in 10 mL 1/1 TFA/CH$_2$Cl$_2$ solution and left stirring at rt for 2 h. After solvent evaporation, the solid residue was washed with 3×3 mL diethyl ether and dried under vacuum to produce 5 as TFA salt. Compound 5 was obtained in quantitative yield and used without further purification after lyophilization. $^1$H NMR (D$_2$O) δ: 8.01 (d, 2H), 7.89 (m, 2H), 7.78-7.44 (m, 4H), 4.78-4.75 (m, 2H), 4.32 (m, 1H), 4.11-4.09 (m, 1H), 4.01-3.98 (t, 1H), 3.50-3.11 (m, 3H), 3.10-2.99 (m, 2H), 2.01-1.01 (m, 12H). To a solution of DOTA-NHS (100 mg, 0.13 mmol in 0.5 mL DMSO) was added in small portions of 5. 2TFA (32 mg, 0.04 mmol) and DIEA (0.78 mmol, 136 µL) over a period of 45 min at rt. The solution was then stirred for another 2 h and completion of the reaction was monitored using HPLC. After completion of the reaction the reaction was purified by HPLC to obtain 6. Compound 6 was treated with 20% piperidine solution to Fmoc group and purified using C$_{18}$ flash chromatography using 90/10 H$_2$O/CH$_3$CN (0.1% TFA in each) solution and lyophilized. ESIMS: 1046 [M+H]$^+$. That lyophilized compound (50 mg, 0.047 mmol) was dissolved in distilled water (2 mL) added to solution of Gd$_2$(CO$_3$)$_3$ (0.26 mmol in 3 mL water) and stirred at 60° C. for 12 h. The compound 7 was purified using C$_{18}$ flash chromatography using a gradient of 90/10 to 80/20 H$_2$O/CH$_3$CN (0.1% TFA in each) solution and lyophilized. To a solution of 3 (25 mg, 0.004 mmol) in DMSO, was added 7 (40 mg, 0.003 mmol) slowly for 30 min and stirred for about 2 h at rt until the reaction is completed. Completion of the reaction was monitored using HPLC. After completion, reaction mixture subsequently was purified by HPLC and product was lyophilized. ESI-MS: 1813.08 [M+H]$^+$. found: 1813.08. Compound was then purified by HPLC. Method 1: Calcd. for C$_{64}$H$_{103}$Gd$_2$N$_{15}$O$_{26}$, 1813.5681 [M]$^+$. found 1813.5681 [M+1]. solvent A (0.1% TFA in water) and solvent B (0.1% TFA in acetonitrile), flow rate 8 mL/min. The elution gradient was 100% A and 0% B for 5 min and 100% A to 80% A and 0% B to 20% B over 5-25 min, and 80% A to 20% A and 20% B to 80% B from 25-30 min.

(3S,7S)-5,13,20,28-tetraoxo-32-(2,4,6-tris(1-(2-hydroxy-3-(4,7,10-tris(carboxymethyl)-1,4,7,10-tetraazacyclododecan-1-yl)propyl)-1H-1,2,3-triazol-4-yl)phenoxy)-4,6,12,21,27-pentaazadotriacontane-1,3,7,22-tetracarboxylic acid, trigadolinium(III) salt.
Gd3

Gd3 is prepared by using multistep synthesis as shown in Scheme 3. Compound 8 was prepared following previous report.

2,5-dioxopyrrolidin-1-yl 5-(2,4,6-triethynylphenoxy)pentanoate, 9

To a solution of 8 (300 mg, 1.13 mmol in 5 mL DMF) was added TSTU (440 mg, 1.47 mmol) and TEA (541 µL, 3.39 mmol) and the resulting solution was left stirring at room temp for 4 h until the reaction was completed monitored by TLC. The solvent was removed under high vacuum and the residue was dissolved in CH$_2$Cl$_2$ and purified by silica gel column using 40/60 to 50/50 EtOAc/hexane solution as eluent. Fractions containing the product were combined together and evaporated to obtain the desired product as colorless solid. Yield ~310 mg. NMR (CDCl$_3$): δ 7.56 (s, 2H), 4.26 (t, 2H), 3.39 (s, 2H), 3.04 (s, 1H), 2.78 (s, 4H) 2.48 (t, 2H), 2.01-1.80 (m, 4H).

(3S,7S)-26-amino-5,13,20-trioxo-4,6,12,21-tetraazahexacosane-1,3,7,22-tetracarboxylic acid 2,2,2-trifluoroacetic acid salt, 10

Compound 10 was prepared following a previous report. Briefly, to a solution of Tris-t-Bu protected 3 (100 mg 0.135 mmol in 1.35 ml DMF), was added H-Lys(Boc)(O-t-Bu) (59.5 mg, 0.175 mmol) followed by DIEA (70.7 µL, 0.135) and the clear solution was stirred overnight at rt. The solution was then concentrated under vacuum to a clear oily residue. The residue was dissolved in 2:1 MeCN/water (6 mL) and lyophilized to obtain a clear foamy product Yield. Product was used without further purification. Yield: 117 mg, 0.126 mmol, 93%. ESI-MS: 928 [M+H]$^+$. The compound was dissolved in an ice-cold solution of 2 ml TFA/CH$_2$Cl$_2$ followed by dropwise addition of TES (278 µL, 1.7 mmol). The clear solution kept stirring for 5 h, concentrated under vacuum. The residue was dissolved in 5 mL water and purified using reverse phase flash chromatography. Product was eluted using 80/20 water/CH$_3$CN (0.1% TFA in each). ESI-MS: 603 [M+H]$^+$.

(3S,7S)-5,13,20,28-tetraoxo-32-(2,4,6-triethynylphenoxy)-4,6,12,21,27-pentaazadotriacontane-1,3,7,22-tetracarboxylic acid, 11

Compound 9 (132 mg, 0.362 mmol) was added in one portion to a solution containing (3S,7S)-26-amino-5,13,20-trioxo-4,6,12,21-tetraazahexacosane-1,3,7,22-tetracarboxylic acid 2,2,2-trifluoroacetic acid salt (260 mg, 0.362 mmol), triethylamine (0.202 mL, 1.44 mmol) and DMF (3.62 mL). The mixture was stirred at room temperature for 4 h and concentrated to a tan residue. The residue was dissolved in 1/1 water/acetonitrile (3 mL) and purified using C<sub>18</sub> reverse phase flash chromatography with a step gradient consisting of 100% water, 0.1% TFA, followed by 80/20, 60/40. water/acetonitrile (0.1% TFA in each). Each gradient step consisted of approximately 144 mL solvent volume. The flow rate was 40 mL/min. Fractions containing the desired product were concentrated to a residue and lyophilized to give (3S,7S)-5,13,20,28-tetraoxo-32-(2,4,6-triethynylphenoxy)-4,6,12,21,27-pentaazadotriacontane-1,3,7,22-tetracarboxylic acid as a white solid. 169 mg, 54% yield. ESI-MS calcd for $C_{43}H_{57}N_5O_{13}$ [M+H]$^+$ 852.4. found 851.9. $^1$H NMR (400 MHz, DMSO-$d_6$) 12.12 (bs, 4H) 8.01 (d, 1H), 7.76 (m, 2H), 7.57 (s, 2H), 6.33 (m, 2H), 4.47 (s, 2H), 4.28 (s, 1H), 4.09-4.15 (m, 4H), 3.00 (m, 4H), 2.21-2.27 (m, 2H), 2.10 (m, 4H), 2.02 (t, 2H), 1.89-1.94 (m, 1H), 1.22-1.69 (m, 24H). $^{13}$C NMR (100 MHz, DMSO-$d_6$) δ175.0, 174.6, 174.3, 174.1, 172.8, 172.3, 172.1, 162.1, 158.9, 158.5, 157.7, 137.6, 118.0, 117.5, 86.6, 82.0, 81.5, 78.6, 74.1, 52.7, 52.1, 38.7, 38.6, 35.8, 35.5, 32.2, 31.1, 30.3, 29.7, 29.3, 29.2, 28.9, 28.8, 27.9, 25.7, 25.6, 23.3, 23.0, 22.1.

Gd3.

To a mixture containing (3S,7S)-5,13,20,28-tetraoxo-32-(2,4,6-triethynylphenoxy)-4,6,12,21,27 pentaazadotriacontane-1,3,7,22-tetracarboxylic acid (12 mg, 0.14 mmol), compound 002 (28 mg, 0.046 mmol) and t-butanol (0.1 mL) was added water (0.05 mL) followed by TBTA (0.15 mg, 0.3 μmol) and tetrakis(acetonitrile)copper(I) hexafluorophosphate (0.11 mg, 0.3 μmol). The mixture was stirred at 65° C. for 18 h. The reaction mixture was dissolved in 2.5 mL of 0.1% sodium bicarbonate and filtered. The solution thus obtained was purified on HPLC using a Phenomenex, Luna, 10 micron, 10×250 mm column and a gradient consisting of 0-95% acetonitrile:water over 20 minutes. The desired product (003) eluted at 6.1-7.1 minutes. The fractions containing 003 were combined, concentrated and lyophilized to afford a white solid. 13 mg, 34% yield. ESI-MS calcd for $C_{94}H_{141}Gd_3N_{26}O_{34}$ [M−H]$^-$ 2650.7. found 2648.9.

Scheme 1

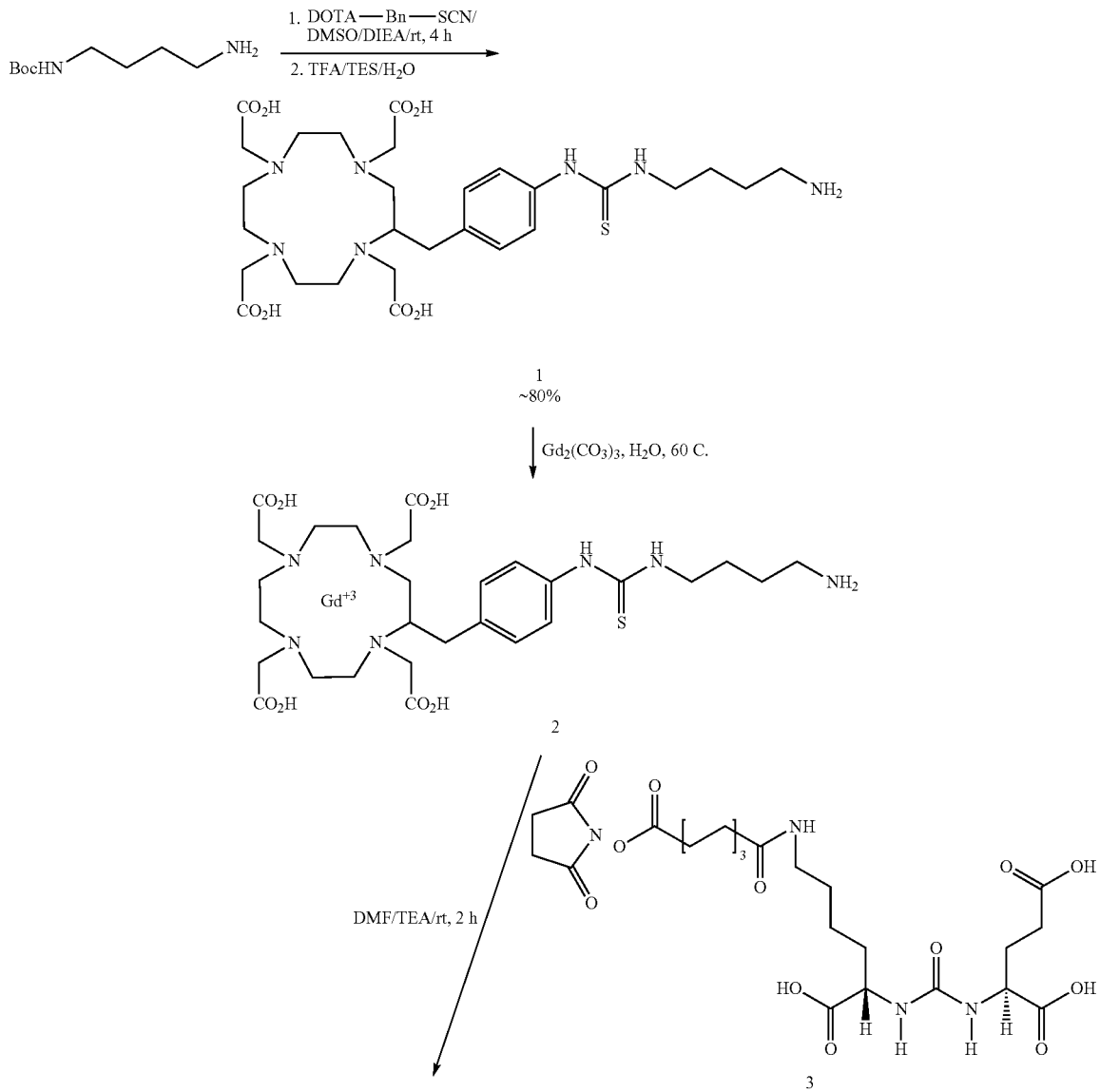

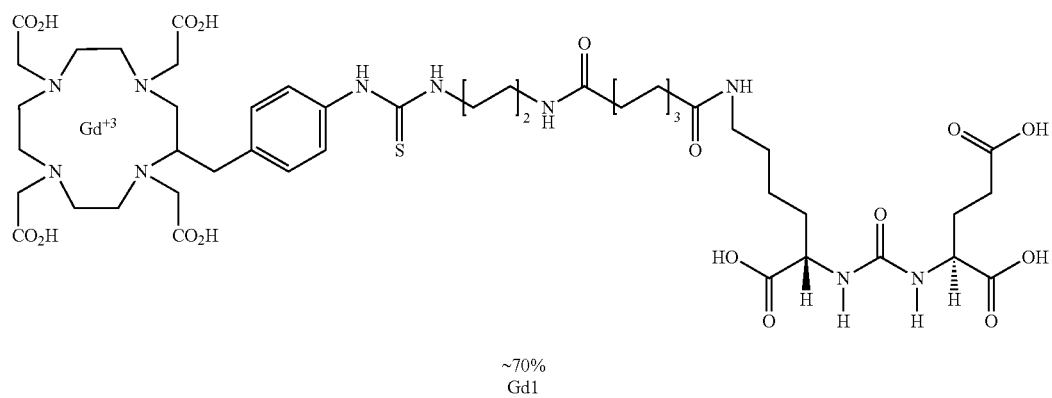
~70%
Gd1
Scheme 2
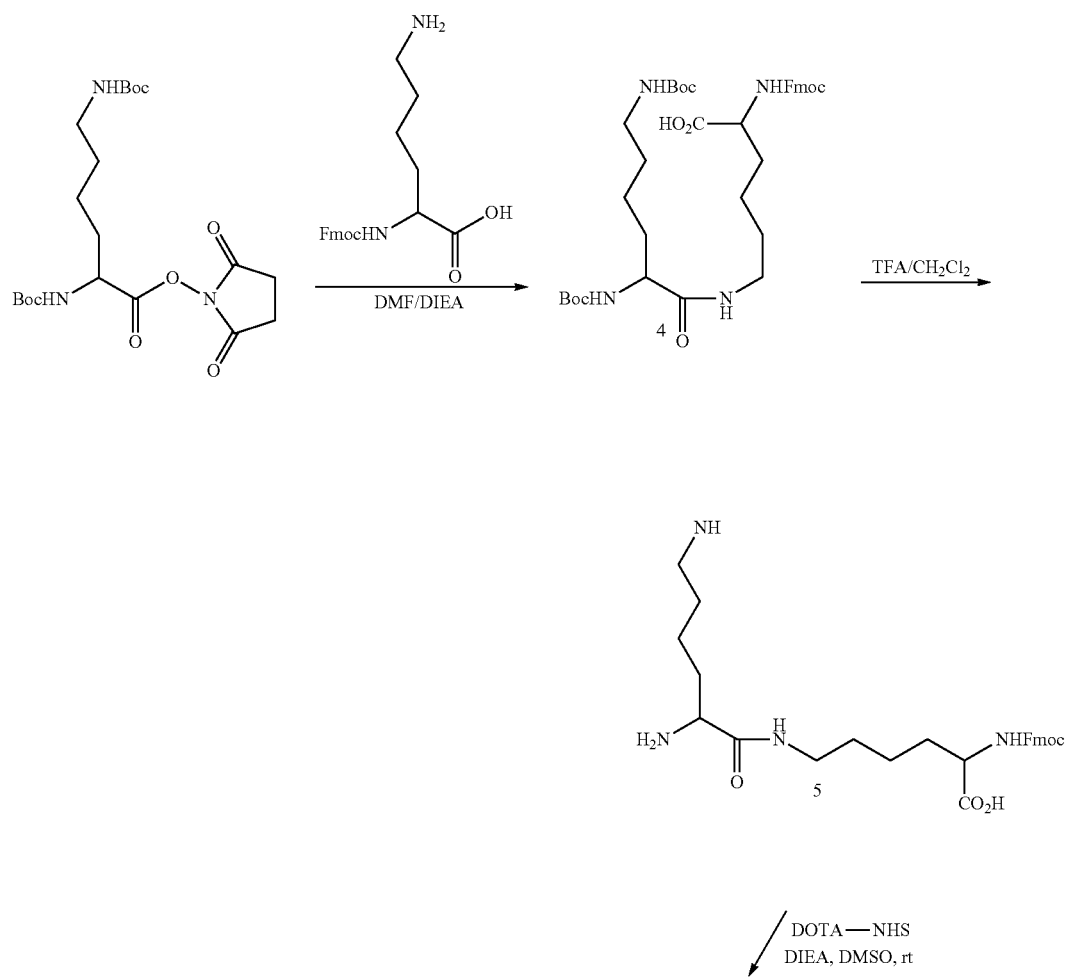

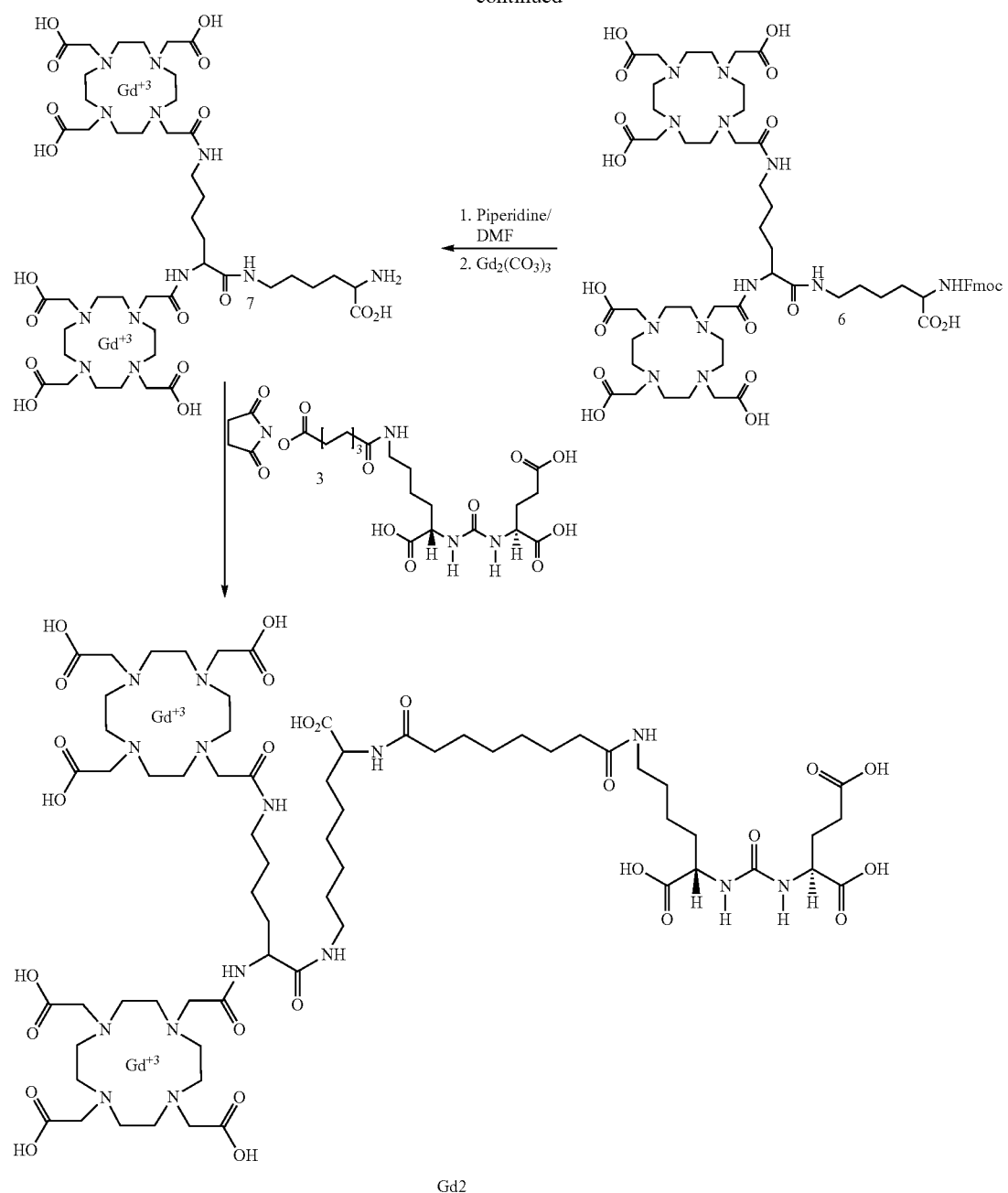
Gd2
Scheme 3
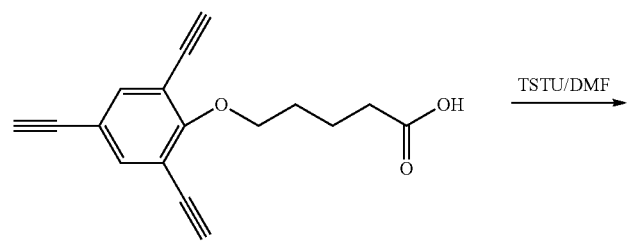

-continued
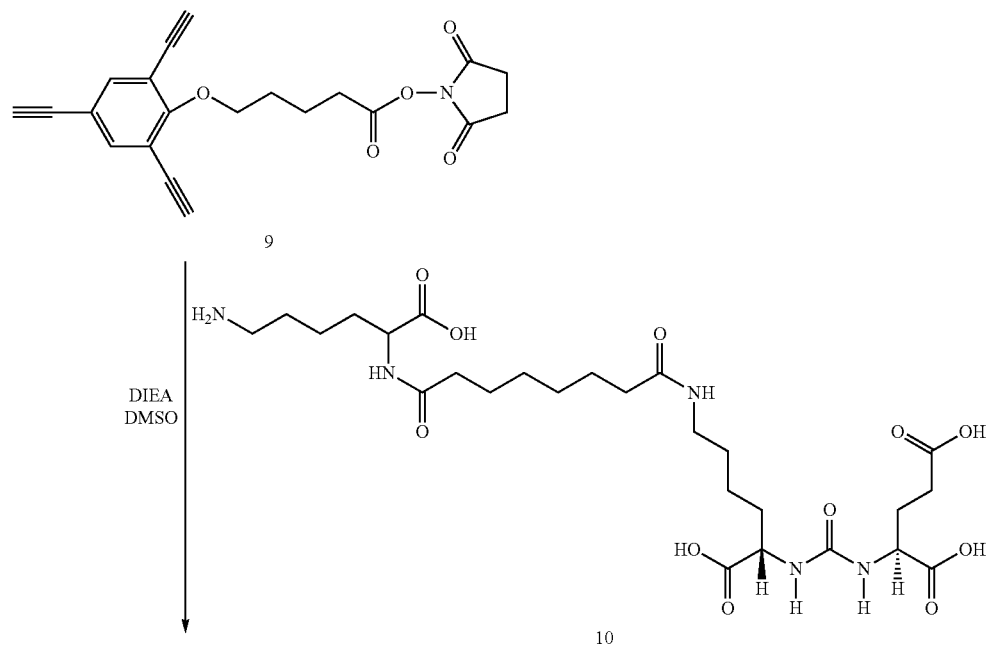
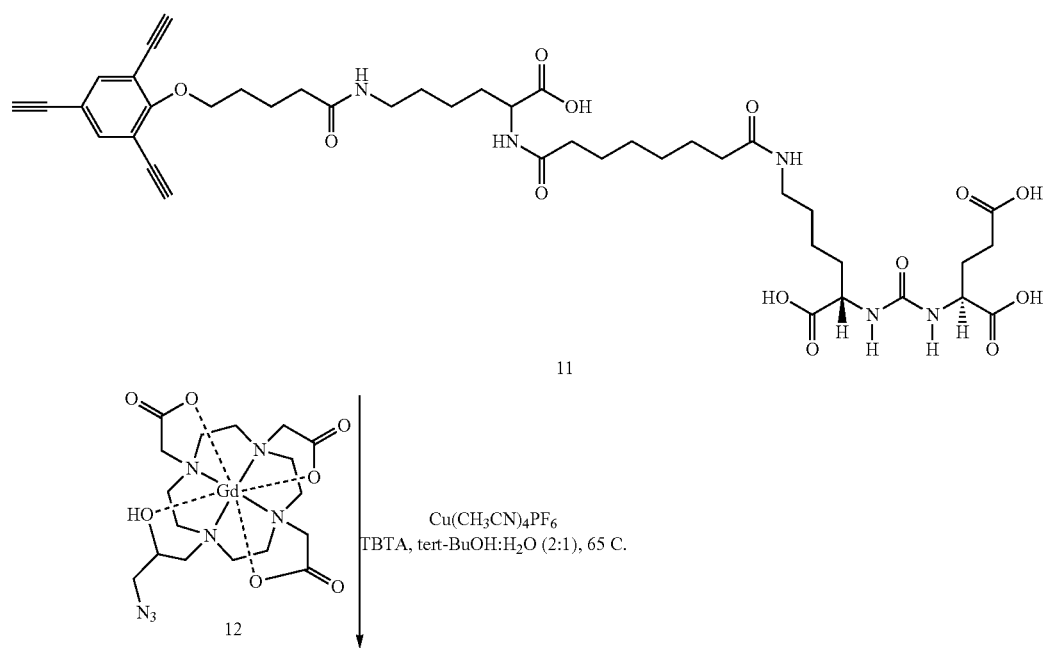

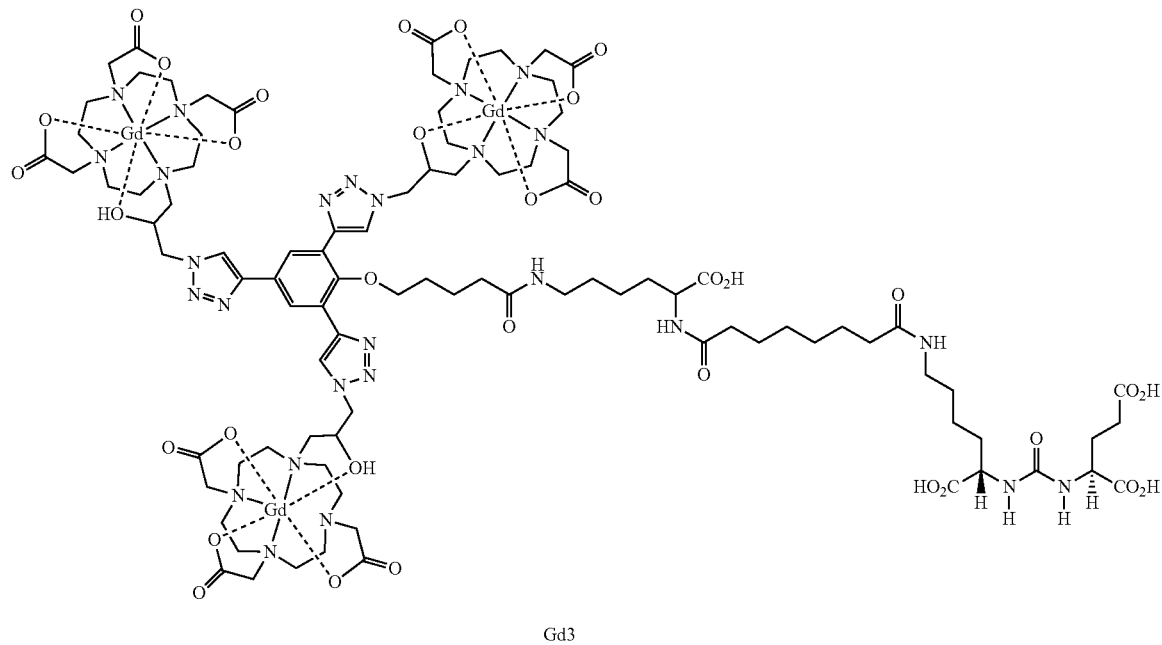

Gd3

Results

Structures of representative PSMA contrast agents mono-, di- and trimeric Gd (Gd1, Gd2 and Gd3) are shown in FIG. 1A containing Lys-Glu urea as the targeting moiety. Multi-step solution phase synthetic methods were developed to prepare the target compounds and are outlined in Schemes 1-3.

For all three compounds, chelating agent DOTA was used since it forms complexes with high thermodynamic and kinetic stability. Gd1 contains DOTA-Bn-SCN to provide higher relaxivity. The structure of Gd1 is based on recently reported lead 86Y-labeled imaging agent for positron emission tomography (PET), which demonstrated high and specific tumor accumulation in a preclinical model (Banerjee, et al. 2015). Gd2 was prepared by conjugating both ∞- and ε-amines of lysine with DOTA-NHS, employing a solution-based peptide synthesis strategy. Under the same conditions, yields of the coupling reactions were significantly improved when the reaction was performed in a sonication bath at room temperature. Gd3 contains a phenolic core to which three Gd(III)-DOTA were bound through rigid triazole linkage as previously reported by Mastarone et al. using click chemistry. To that core, was conjugated the PSMA-targeting functionality through the phenolic oxygen. Gd3 demonstrated relatively high relaxivities as a result of increased rigidity of triazole linker moiety. Compounds were purified by reverse phase HPLC and characterized by LCMS. To ascertain any potentially negative effects of the Gd(III) containing portion of the agents on the binding affinities of the probes, values of the PSMA inhibition constant (Ki) for Gd1, Gd2 and Gd3 were determined using a fluorescence-based PSMA inhibition assay and are listed in Table 1.

TABLE 1

Physical properties of contrast agents

| Compound | Molar Mass (g/mol) | $r_1$[a] ($mM^{-1} s^{-1}$) | $T_1$ ($mM^{-1} s^{-1}$) | $K_i$ [nM][b] | 95% CI of $K_i$ [nM] |
|---|---|---|---|---|---|
| Gd1 | 1250.40 | 3.0 | 2.65 | 0.45 | 0.36-0.55 |
| Gd2 | 1803.13 | 6.2/12.5 | 5.44 | 18.18 | 14.07-22.16 |
| Gd3 | 2651.03 | 3.3/9.81 | 12.47 | 7.19 | 5.17-10.01 |

[a]Relaxivities listed indicate the ionic/molecular relaxivity of the agents, respectively.
[b]ZJ43 ($K_i$ 0.29; 95% CI of $K_i$ 0.22-0.39 nM).

The known, high-affinity PSMA inhibitor, N—[[[(S)-1-carboxy-3-methylbutyl]amino]carbonyl]-L-glutamic acid (ZJ43) (Olszewski et al., 2004), was used as a reference ligand. As expected all compounds showed high binding affinity with Ki values ranging highest for Gd1 (0.45 nM) followed by Gd3 (7.19 nM) and Gd2 (18.18 nM) the lowest. When imaged at 9.4 T and 25° C., solution phantoms indicated r1 relaxivities in PBS that vary between 3.0 and 6.2 $mM^{-1}$ $s^{-1}$ per Gd(III) and between 3.0 and 12.5 mM-1 s-1 per contrast agent (Table 1). As expected, Gd1 has the lowest relaxivity followed by Gd2 and Gd3 at 25° C. To determine selectivity and specificity of the agents, human prostate cancer cells genetically modified to express high amounts of PSMA (PC3 PIP) and the corresponding wild-type, PSMA-non-expressing cells (PC3 flu) were selected as negative control (Banerjee, Angew., 2001). After incubation with either Gd1 or Gd2, pelleted PSMA+PC3 PIP and PSMA− PC3 flu cells did not demonstrate $T_1$-weighted MR contrast or changes in $R_1$. Conversely, $T_1$-weighted images of both cell lines incubated with Gd3 displayed significant MR contrast enhancement in PSMA+PC3 PIP cells compared to the unlabeled cells as well as to the PSMA− PC3 flu cells pellets as shown in FIG. 4A. Enhancement and $T_1$ measurements by means of MRI of the cell pellets in the presence and absence of 50 μM Gd3 indicated higher enhancement and difference in $T_1$ relaxation rates, $\Delta R1$ between Gd3 treated PIP cells and the control PIP cells as compared to the Gd3-treated flu cells and the control flu control cells, after removal of the Gd3 from the cell system by washing with standard medium (FIG. 4B and FIG. 4C).

Selective blocking experiment by performing co-incubation of Gd3 and ZJ43 indeed showed significant blocking of $T_1$ enhancement. Cells incubated with Gd3 in the presence of ZJ43 showed only minor changes in $T_1$ value in both types of cells, indicating that ZJ43 was able to block the binding of Gd3 specifically. Those results indicated that Gd3 exhibited receptor-specific cell binding on PSMA+PC3 PIP cells and displayed PSMA-mediated contrast enhancement, proving the concept of receptor mediated endocytosis. ICP-MS analysis of the cells after post image analysis indeed showed there was negligible Gd(III) associated with PC3 flu cell pellets while the PC3 PIP cell pellets has high Gd amount (FIG. 2 and FIG. 3). The PSMA+PC3 PIP cell pellets had an estimated intracellular Gd(III) concentration of ~22.82 µM for Gd3 followed by ~12.5 µM and ~7.2 µM for Gd2 and Gd1, respectively (FIG. 2). Thus, the difference between $\Delta R_1$ of the PIP cells and that of the flu cells reflects the change due to the specific Gd3 binding to PSMA in the PIP cells.

Figure 5A:
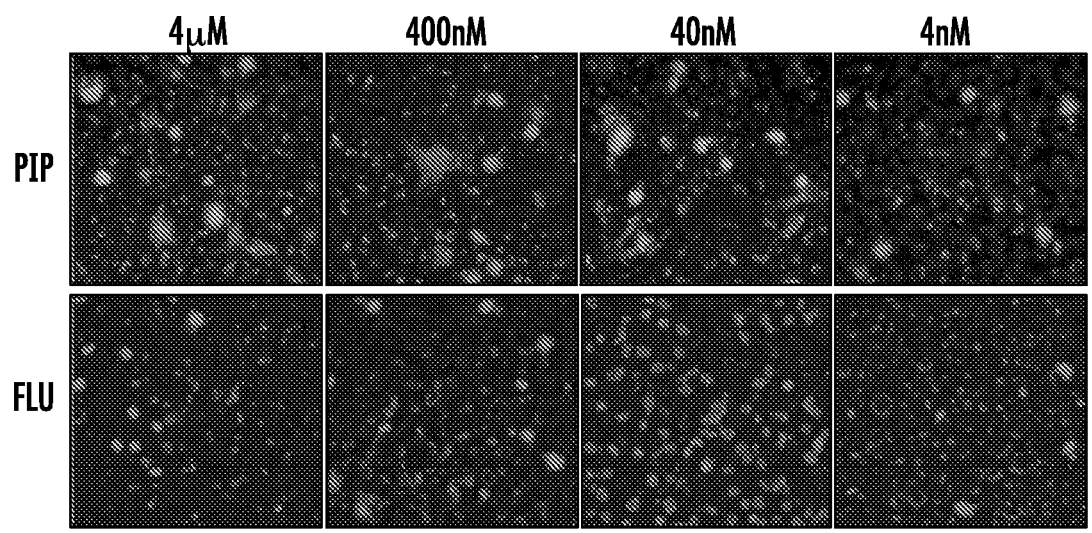
Figure 5B:
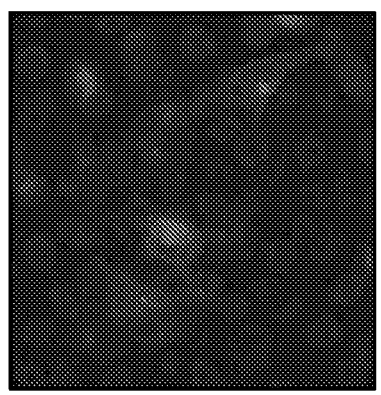
Figure 5C:
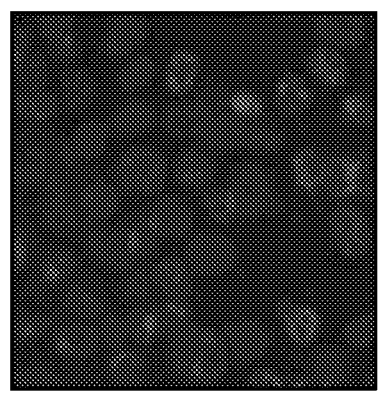
Figure 5D:
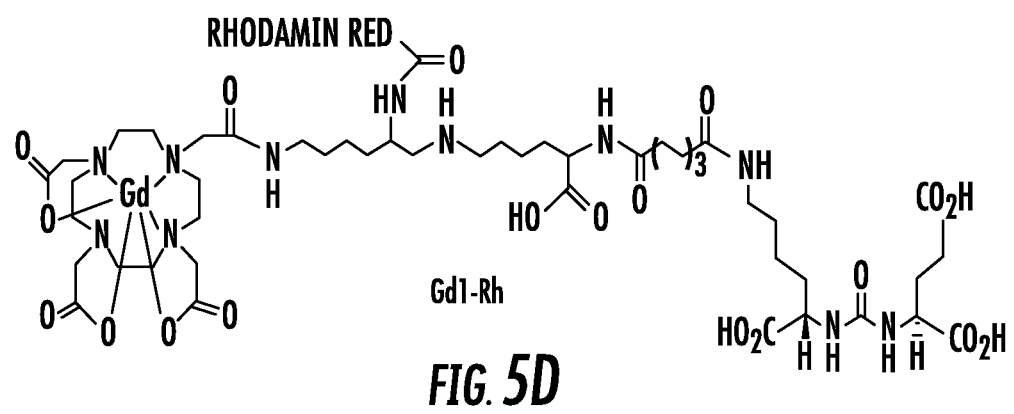

A cell internalization assay revealed that the percent of incubated dose (% ID) that underwent internalization in PSMA+PC3 PIP cells for Gd1 and Gd2 was 9.06±0.31 and 21.63±3.51 after 4 h of incubation, respectively, whereas only 2.42±0.11 and 3.51±1.32% ID was associated with the cell surface at that time (FIG. 3). Moreover, slightly higher non-specific uptake was associated with Gd2 in PSMA– PC3 flu cells, which might be related to the lower $K_1$ value of this agent compared to Gd1. As a further check on cellular uptake and internalization, a dual modality Gd monomeric contrast agent labeled with Rhodamine-Red™-X was prepared to confirm the PSMA-mediated internalization of this class of contrast agents (FIG. 5D). As anticipated, the agent demonstrated specific and high accumulation only in PSMA+PC3 PIP cells (FIG. 5A through FIG. 5C). These results show that cell receptors expressed at this level can be detected by MRI using these simple targeted agents.

A time-dependent internalization study was performed for Gd3 (FIG. 6A and FIG. 6B) after 1, 4 and 24 h of incubation. Intracellular uptake at 1 and 4 h was high and specific, 28.30±0.47 and 39.92±3.59% ID, respectively, in PSMA+ PC3 PIP cells, whereas at 24 h post-incubation, ~89.69±3.90% ID was observed. A similar amount of Gd (~33-37% ID) was associated with the cell membrane at those same time-points. These results indicate that detectable $T_1$-weighted enhancement of Gd3 in PSMA+PC3 PIP cell pellets correlated well with the high, specific accumulation of Gd3 in PSMA+ PIP cells.

Prior to evaluating Gd3 for live mouse imaging, its biocompatibility was examined using a cell proliferation assay. Various concentrations of Gd3 were incubated with PSMA+PC3 PIP and PSMA– PC3 flu cells, for 24 h. Gd3 did not have a significant effect on the viability of PSMA–flu cells up to a Gd(III) concentration of 1 mM (i.e. ~90% viability) (FIG. 7). However, Gd(III) concentrations of >1 mM affected PSMA+PC3 PIP cell viability (FIG. 8). The observed level of PSMA+PC3 PIP cell death may be attributable to high cell internalization of Gd3, and the long incubation time employed (24 h).

In vivo MR imaging was performed by using male NOD/SCID mice bearing PSMA+PC3 PIP (right) and PSMA– PC3 flu (left) tumor implanted subcutaneously in the lower right and left flanks respectively, after the intravenous injection of Gd3 (0.05 mmol/Kg dose) at 9.4 T. During first 20 min after injection both PIP and flu tumors received non-specific uptake. A sharp lowering of $T_1$ values were observed in all tissues, PSMA flu being highest 0.63 sec followed by PIP tumor 0.57 sec and muscle 0.261 sec. Significantly, fast clearance of contrast agent was observed from muscle and flu tumor. Contrast enhancement at PIP tumor was highest, 36%, at 40 min post-injection and remained high 30% until 1.5 h post injection. At 3 h, $T_1$ values of muscle and flu tumor were found went back to initial values whereas $T_1$ values of PIP tumor showed no significant change.

In vivo MR imaging of Gd3 was also performed on mice bearing PSMA+PC3 PIP and PSMA– PC3 flu tumor xenografts implanted subcutaneously in the lower right and left flanks respectively, after a single bolus intravenous injection (0.06 mmol/kg). FIG. 9A displays quantitative contrast enhancement mapping ($\Delta R_1$) of 1 mm slices for both tumors at 40 to 160 min post-injection. Contrast enhancement remained constant for at least 3 h within the PSMA+PC3 PIP tumor, but it decreased quickly within the PSMA– PC3 flu tumor and muscle tissues. Changes in the $T_1$ values of the PSMA+PC3 PIP tumor (FIG. 10A and FIG. 10B) reached a minimum of 1,819±76 ms (mean±SD, average 36% enhancement in $R_1$ values, n=4) in the first 40 to 60 min, and remained constant, at 29%, until 90 min, and slowly decreased to 24% at 190 min after injection. For the PSMA–PC3 flu tumors, highest contrast enhancement was ~24% at 20 min post-injection, followed by rapid decay in contrast enhancement ($\Delta R_1 < 20\%$ after 40 min). These results demonstrate specific contrast enhancement for PSMA+PC3 PIP tumors ($P \leq 0.05$) at 80 and 120 min post-injection. As shown in FIG. 9B these results were compared directly with other mice dosed in the same fashion using a trimeric Gd-probe without a targeting moiety, which showed no tumor enhancement (Mastarone, 2011).

Under the same experimental condition, a control study with saline (PBS) did not show any changes in $T_1$ value for PIP and flu tumor (FIG. 12).

Without wishing to be bound to any one particular theory, upon binding with PSMA, the rotational correlation time of Gd3 increased relative to the unbound state. Binding may also have changed the hydration number and water exchange rate for each agent, which could change the relaxivity values from those expected from the relaxivities of the free contrast agents (Caravan et al., 2007). Also, at high fields, increasing the rotational correlation time may slightly reduce relaxivity due to interaction of the contrast agent with cellular components (Caravan, P., et al. 2009; De Leon-Rodriguez, L. M., et al. 2010; Geninatti-Crich, S. 2011). By leveraging sensitive, multimeric Gd(III) complexes in combination with an established PSMA-targeting small molecule, PSMA-targeted MR molecular imaging in vitro and in vivo were performed.

In summary, it has been shown that Gd-based contrast agent Gd3, could be used for PSMA-specific MR imaging in vivo using mouse xenografts. Optimization of the constructs described for translational use in prostate and other cancers is under way.

Example 2

Receptor Concentration of PSMA

No. receptors per cell (N.R.C.)=4.9×10$^6$, $r_{cell}$=8.75 μm $$PC3 \text{ cell volume} = \frac{4}{3}\pi r_{cell}^3 = \sim 2.57 \text{ pL}$$

$$[PSMA]_{cell} = \frac{N.R.C./N_A}{\frac{4}{3}\pi r_{cell}^3} = \sim 3.16 \text{ } \mu M$$

Therefore, to see a change of 0.05 sec$^{-1}$ (approximately 10% enhancement, considering tissue T$^0{}_1$=2 sec), relaxivity required (if receptor: contrast 1:1)

$$r_i = \frac{\Delta\left(\frac{1}{T}\right)}{[CA^1]} = \sim 16 \text{ sec}^{-1}(mM)^{-1}$$

Example 3

Preclinical Evaluation of $^{86}$Y-Labeled Inhibitors of Prostate-Specific Membrane Antigen for Dosimetry Estimates Overview $^{86}$Y (half-life=14.74 h, 33% β$^+$) is within an emerging class of positron-emitting isotopes with relatively long physical half lives that enables extended imaging of biologic processes. The preparation and investigation of the biodistribution of three low-molecular weight $^{86}$Y-labeled PSMA-binding ureas (FIG. 14) in a rodent experimental model have been reported, as well as the imaging of the most pharmacokinetically favorable agent in non-human primates for radiation dosimetry in preparation for clinical trials with the corresponding $^{90}$Y- and $^{177}$Lu-labeled agents.

Multistep syntheses were used in preparing [$^{86}$Y]-4-6. PSMA inhibition constants were evaluated by competitive binding assay. In vivo characterization using tumor-bearing male mice was performed by PET/CT for [$^{86}$Y]-4-6 and by biodistribution studies of [$^{86}$Y]-4 and [$^{86}$Y]-6 out to 24 h after injection. Quantitative whole-body PET scans were recorded to measure the kinetics for 14 organs in a male baboon using [$^{86}$Y]-6.

Compounds [$^{86}$Y]-4-6 were obtained in high radiochemical yield and purity, with specific radioactivities of more than 83.92 GBq/μmol. PET imaging and biodistribution studies using PSMA½ positive PC-3 PIP and PSMA-negative PC-3 flu tumor-bearing mice revealed that [$^{86}$Y]-4-6 had high site-specific uptake in PSMA-positive PC-3 PIP tumor starting at 20 min after injection and remained high at 24 h. Compound [$^{86}$Y]-6 demonstrated the highest tumor uptake and retention, with 32.17±7.99 and 15.79±6.44 percentage injected dose per gram (% ID/g) at 5 and 24 h, respectively. Low activity concentrations were associated with blood and normal organs, except for kidneys, a PSMA-expressing tissue. PET imaging in baboons reveals that all organs have a 2-phase (rapid and slow) clearance, with the highest uptake (8% ID/g) in the kidneys at 25 min. The individual absolute uptake kinetics were used to calculate radiation doses using the OLINDA/EXM software. The highest mean absorbed dose was received by the renal cortex, with 1.9 mGy per MBq of [$^{86}$Y]-6.

Materials and Methods

Solvents and chemicals obtained from commercial sources were of analytical grade or better and used without further purification. All 9-fluorenylmethyloxycarbonyl (Fmoc) protected amino acids including the Fmoc-Lys (Boc)-Wang resin, 1-hydroxybenzotriazole monohydrate and 2-(1H-benzotriazole-1-yl)-1,1,3,3-tetramethyluronium hexafluorophosphate (HBTU) were purchased from Chem Impex International Inc. (Wooddale, Ill.). Carrier-free [$^{86}$Y] (NO$_3$)$_3$ was obtained from the National Cancer Institute of the National Institutes of Health (Bethesda). DOTA-tris(t-butyl ester)-monoacid and p-SCN-Bn-DOTA (B-205) were purchased from Macrocyclics, Inc. (Dallas, Tex.). Yttrium (III) nitrate, triethylsilane (Et$_3$SiH), diisopropylethylamine (DIEA) and triethylamine (TEA) were purchased from Sigma-Aldrich (Saint Louis, Mo., USA). All other chemicals were purchased from Thermo Fisher Scientific (Pittsburgh, Pa.) unless otherwise specified. Analytical thin-layer chromatography (TLC) was performed using Aldrich aluminum-backed 0.2 mm silica gel Z19, 329-1 plates and visualized by ultraviolet light (254 nm), I$_2$ and 1% ninhydrin in EtOH. Flash chromatography was performed using silica gel purchased from Bodman (Aston, Pa.), MP SiliTech 32-63 D 60 Å. All experiments were performed in duplicate or triplicate to ensure reproducibility. $^1$H NMR spectra were recorded on a Bruker Ultrashield™ 400 MHz spectrometer. Chemical shifts (8) are reported in ppm downfield by reference to proton resonances resulting from incomplete deuteration of the NMR solvent. Low resolution ESI mass spectra were obtained on a Bruker Daltonics Esquire 3000 Plus spectrometer, Billerica, Mass. High resolution mass spectra were obtained by the University of Notre Dame Mass Spectrometry & Proteomics Facility, Notre Dame, Ind. using ESI either by direct infusion on a Bruker micrOTOF-II or by LC elution via an ultra-high pressure Dionex RSLC with C$_{18}$ column coupled with a Bruker micrOTOF-Q II.

High-performance liquid chromatographic (HPLC) purification of 4-6 and [$^{89}$Y]4-6 was performed using a Phenomenex C$_{18}$ Luna 10×250 mm$^2$ column on a Waters 600E Delta LC system with a Waters 486 variable wavelength UV/Vis detector, both controlled by Empower software (Waters Corporation, Milford, Mass.) (FIG. 15A and FIG. 15B, FIG. 16A and FIG. 16B, and FIG. 17A, FIG. 17B and FIG. 17C). HPLC was performed using the following methods using solvent A (0.1% TFA in water) and solvent B (0.1% TFA in acetonitrile). Method 1: The elution gradient was 75% A and 25% B for 5 min and 75% A to 60% A and 25% B to 40% B over 5-25 min, and 60% A to 75% A and 40% B to 25% B from 25-30 min, flow rate 8 mL/min. Method 2: flow rate 8 mL/min. The elution gradient was 100% A and 0% B for 0-5 min, and 100% A to 45% A and 0% B to 55% B for 5-45 min. HPLC purification of [$^{86}$Y]4-6 was performed on a Varian Prostar System (Palo Alto, Calif.), equipped with a model 490 UV absorbance detector and a Bioscan NaI scintillation detector connected to a Bioscan Flow-count system (Bioscan, Washington D.C., USA). For HPLC purification of [$^{86}$Y]4-6 a Waters Novapak C$_{18}$ 150×3.9 mm$^2$ column was used. HPLC was performed using the following methods using solvent A (0.1% TFA in water) and solvent B (0.1% TFA in CH$_3$CN) and flow rate 1 mL/min. A isocratic method 85% A and 15% B for 25 min was used for purification of [$^{86}$Y]4. A gradient method, 0-5 min 78% A and 22% B, 5-25 min 78% A to 58% A and 22% B to 42% B was employed for [$^{86}$Y]5. A gradient method 0-5 min 88% A and 12% B, 5-25 min 88% A to 68% A and 12%

B to 32% B was used for purification of [$^{86}$Y]6. The specific radioactivity was calculated as the radioactivity eluting at the retention time of product during the preparative HPLC purification divided by the mass corresponding to the area under the curve of the UV absorption. All final compounds were obtained in >95% radiochemical purity, as determined by HPLC. Compound 1 was prepared following a previous report (Banerjee, Pullambhatla, Byun, et al., 2011). Compounds 4 and 5 were prepared by same general method as reported earlier for 4 (Banerjee et al., 2010), and briefly mentioned below for 5.

Synthesis and Radiochemistry (13S,27S,31S)-4,7,10-tribenzyl-2,5,8,11,18,21,29-heptaoxo-1-(4,7,10-tris(carboxymethyl)-1,4,7,10-tetraazacyclododecan-1-yl)-3,6,9,12,17,22,28,30-octaazatritriacontane-13,27,31,33-tetracarboxylic acid, 5

Compound 5 was prepared by following a previous report ((Banerjee et al., 2010) as outlined in Scheme 4. Compounds 3 and 4 were prepared by following a solid phase peptide strategy. Fmoc-Lys(Boc)-Wang resin (100 mg, 0.43 mM) was allowed to swell with $CH_2Cl_2$ (3 mL) followed by DMF (3 mL). A solution of 20% piperidine in DMF (3×3 mL) was added to the resin that was then shaken gently on a mechanical shaker for 30 min at ambient temperature. The resin was washed with DMF (3×3 mL) and $CH_2Cl_2$ (3×3 mL). Formation of free amine was assessed by the Kaiser test (Kaiser et al., 1970). After swelling the resin in DMF, a solution of Fmoc-Phe-OH (3 eq), HBTU (3 eq), HOBt (3 eq), and DIPEA (4.0 eq) in DMF was added and gently shaken for 2 h. The resin was then washed with DMF (3×3 mL) and $CH_2Cl_2$ (3×3 mL). The coupling efficiency was assessed by the Kaiser Test. That aforementioned sequence was repeated for two more coupling steps with Fmoc-Phe-OH and DOTA-(t-butyl ester)$_3$-$CO_2$H. Final compound was cleaved from the resin using TFA/$CH_2Cl_2$ (1/1) and concentrated under vacuum to produce 3. The concentrated product was purified by using a $C_{18}$ SepPak Vac 2 g column. The product was eluted with a solution of 70/30 water/acetonitrile (0.1% TFA in each) and lyophilized. ESI-MS: 974 [M+H]$^+$. To a solution of 3 (15 mg, 15.4 µmol in 1 mL DMSO) was added 1 (15 mg, 26.18 µmol) and TEA (30 µL) and left at ambient temperature for 2 h. After solvent removal compound 5 was purified by HPLC (Method 1). $^1$H NMR (DMSO-d$_6$) δ: 8.64 (m, 1H), 8.44 (m, 1H), 8.29-8.18 (m, 2H), 7.77-7.75 (m, 2H), 7.30-7.17 (m, 15H), 6.35-6.33 (m, 2H), 4.65-4.63 (m, 2H), 4.17-2.59 (m, 26), 2.40-1.11 (m, 30H). $^{13}$C NMR (DMSO-d$_6$) δ: 175.00, 174.64, 173.82, 173.52, 172.11, 172.02, 171.05, 170.95, 158.20, 157.88, 157.39, 137.79, 137.67, 137.52, 129.52, 129.34, 129.27, 126.35, 54.01, 53.61, 52.36, 51.74, 38.37, 38.31, 37.65, 35.52, 31.88, 29.98, 28.95, 27.61, 25.33, 22.92, 22.73. ESI-MS: 1431 [M+H]$^+$, HRESI+-MS: Calcd. for $C_{69}H_{96}N_{12}O_{21}$, 1431.7042 [M+H]$^+$. found: 1431.7064.

(21S,25S)-8,15,23-trioxo-1-((4-((1,4,7,10-tetrakis(carboxymethyl)-1,4,7,10-tetraazacyclododecan-2-yl)methyl)phenyl)amino)-1-thioxo-2,7,16,22,24-pentaazaheptacosane-21,25,27-tricarboxylic acid, 6

Compound 6 was prepared in three steps as described below. Commercially available N-Boc-1,4 diaminobutane (27 mg, 0.15 mmol in 0.5 ml DMSO) was mixed with 1,4,7,10-Tetraazacyclododecane-1,4,7,10-tetraacetic acid, 2-[(4-isothiocyanatophenyl)methyl] (p-SCN-Bn-DOTA) (100 mg, 0.15 mmol in 1.5 mL DMSO) and DIEA (132 µl, 0.75 mmol) and stirred at 40° C. for 4 h. The solvent was evaporated and the solid residue was purified by reverse phase $C_{18}$ flash chromatography (5.5 g, Agilent SF10) using water and acetonitrile (0.1% TFA in each) to obtain Boc-protected 7 after lyophilization. Yield: ~55%. ESI-MS 740 [M+H]$^+$. The compound resulting from that step was then treated with ice-cold TFA/$CH_2Cl_2$ (1/1) solution and left stirring at ambient temperature for 2 h. The solvent was evaporated and the residue was dried under vacuum and purified by reverse phase flash chromatography (5.5 g, Agilent SF10) to produce 7 in moderate yield. $^1$H NMR (DMSO-d$_6$) δ: 8.80-8.64 (m, 1H), 8.12-7.90 (m, 2H), 7.75-7.10 (bm, 4H), 4.65-4.63 (m, 1H), 4.17-2.59 (m, 27H), 2.40-1.11 (m, 6H). ESI-MS: 640 [M+1]$^+$. To a solution of 7 (11 mg, 17 mol in 400 µL DMSO) was added 1 (10 mg, 17.4 mol in 200 µL DMSO) and DIEA (27 µL, 170 mol) and left at ambient temperature for 2 h. After evaporation of solvent, the residue was dissolved in water and purified by HPLC (Method 2) to obtain 6. R$_t$, 22.5 min. $^1$H NMR (DMSO-d$_6$) δ: 8.88 (m, 1H), 8.44 (m, 1H), 8.21-7.98 (m, 2H), 7.77-7.75 (m, 2H), 6.35-6.33 (m, 2H), 4.65-4.63 (m, 2H), 4.17-2.59 (m, 29H), 2.40-1.11 (m, 30H). HRESI-MS: Calcd. for $C_{48}H_{77}N_{10}O_{17}S$, 1097.5183 [M+H]$^+$. found: 1097.5212.

[$^{89}$Y]4. To a solution of 4 (10 mg, 9.11 µmol in 500 µL 0.5 M NaOAc, pH 6.8) was added 50 µL of YNO$_3$ (0.5 M), and the mixture (pH 6.1) was incubated for 30 min at 90° C. A solution of EDTA (200 µL, 30 mM, pH 6.0) was added, and the reaction mixture was incubated for 10 min at 40° C. to complex unreacted yttrium (III). The resulting compound was purified by HPLC (Method 2, R$_t$, 21 min), concentrated by evaporation and lyophilized. ESI-MS:1370 [M+H]$^+$. Calcd for $C_{60}H_{87}N_{11}O_{20}Y$, 1370.5187. found 1370.5435.

[$^{89}$Y]5. HPLC purification by method 2, R$_t$, 26 min, ESI-MS: 1517 [M+H]$^+$. Calcd for $C_{69}H_{96}N_{12}O_{21}Y$, [M+H]$^+$ 1516.5793. found 1516.5793.

[$^{89}$Y]6. HPLC, Method 2, R$_t$, 23 min. HRESI+-MS. Calcd. for $C_{48}H_{77}N_{10}O_{17}SY$, 1183.4007 [M+H]$^+$. found 1183.4020.

Radiochemistry:

Radiolabeling of [$^{86}$Y]4-5 and [$^{86}$Y]6 were performed by following same general method as described for [$^{86}$Y]6.

[$^{86}$Y]6. A freshly prepared solution of ascorbic acid (50 µL, 220 µg) was added to a solution of $^{86}$YNO$_3$ (111-148 MBq (3-4 mCi) in 0.1 M 500 µL nitric acid) to prevent radiolysis. Approximately 50-70 µg of 6 in 0.3 M NaOAc (purged under N$_2$ for 2-3 min) was added to that solution and neutralized to pH ~5.5-6 by adding 60 µL of 3 M NaOAc followed by brief vortexing of the mixture, which was subsequently incubated for 20 min at 95° C. The reaction mixture was diluted with 1 mL water. Complexation was monitored by injecting aliquots of 10-15 µL of the solution onto the HPLC. The radiolabeled product [$^{86}$Y]6 was obtained in ~90-95% radiochemical yield with radiochemical purity >98%, as measured by ITLC (Gelman ITLC strips, 10 mM EDTA). A broad radioactive peak was obtained R$_t$, ~13.9-14.8 min, for the desired product as mixture isomeric compounds and the R$_t$ for the free ligand was 15.8 min. The specific radioactivity was >83.92 GBq/µmol (n=5). The acidic eluate was neutralized with 20 µL of 1 M sodium carbonate solution and the volume of the eluate was reduced under vacuum to dryness. The solid residue was diluted with saline to the desired radioactivity concentration for biodistribution and imaging studies. Interestingly, after neutralization and evaporation of the eluted peak, only one peak was isolated around 14.3 min upon reinjection of the tracer on HPLC. To verify the isomerization of [$^{86}$Y]6, the compound 6 was radiolabeled with carrier added $^{86}$Y, and the mixture was analyzed via HPLC. Only one peak was isolated at 14.3 min. For [$^{86}$Y]4-5, a single radiolabeled peak was isolated. The R$_t$ for [$^{86}$Y]4 was 14.0 min and that for the uncheled 4 was 15.5 min, whereas, [$^{86}$Y]5, R$_t$=16.9 min, and for the unchelated 5 R$_t$=19.5 min.

Animal Models and Assays:

PSMA inhibitory activities were determined using a fluorescence-based assay (Banerjee, Pullambhatla, Byun, et al., 2011). Enzyme inhibitory constants (Ki values) were generated using the Cheng-Prusoff conversion (Cheng and Prusoff, 1973). Sub-lines of the androgen independent PC-3 human prostate cancer xenograft were used (Banerjee, Pullambhatla, Byun, et al., 2011). Those sub-lines have been modified to express high (PC-3 PIP) or naturally produce low (PC-3 flu) levels of PSMA (Dr. Warren Heston, Cleveland Clinic, Cleveland, Ohio).

Both PSMA-expressing (PC-3 PIP) and non-expressing (PC-3 flu) cell lines were grown in RPMI 1640 medium (Invitrogen) containing 10% fetal bovine serum (FBS) (Invitrogen) and 1% Pen-Strep (Biofluids) as previously described (Banerjee, Pullambhatla, Byun, et al., 2011).

Six- to 8-week-old male, non-obese diabetic (NOD)/severe-combined immunodeficient (SCID) mice (Charles River Laboratories) were implanted subcutaneously (SC) with PSMA+PC-3 PIP and PSMA– PC-3 flu cells (2×10$^6$ in 100 μL of Matrigel) at the cephalad right and left flanks, respectively. Mice were imaged or used in biodistribution assays when the xenografts reached 5 to 7 mm in diameter.

For the biodistribution assay, PSMA+PC-3 PIP and PSMA– PC-3 flu xenograft-bearing NOD/SCID mice were injected via the tail vein with 0.55 MBq (15 μCi) of $^{86}$Y-4 or $^{86}$Y-6. In each case, four mice were sacrificed by cervical dislocation at 1 h, 2 h, 5 h and 24 h post-injection. The heart, lungs, liver, stomach, pancreas, spleen, fat, kidney, muscle, small and large intestines, urinary bladder, and PSMA+PC-3 PIP and PSMA– PC-3 flu tumors were quickly removed. A 0.1-mL sample of blood was also collected. Each organ was weighed, and the tissue radioactivity was measured with an automated gamma counter (1282 Compugamma CS, Pharmacia/LKB Nuclear Inc.). The percentage of injected dose per gram of tissue (% ID/g) was calculated using a serially diluted sample of the injected activity. All activity measurements were corrected for radioactive decay to the time of the injection.

Animal Imaging:

Small Animal PET and CT.

For imaging studies, NOD/SCID mice bearing PSMA+ PC-3 PIP and PSMA– PC-3 flu tumors were anesthetized with 3% and maintained under 1.5% isoflurane (v/v). Mice (n=3 for $^{86}$Y-4 or $^{86}$Y-6 and n=2 for $^{86}$Y-5) were injected via the tail vein with 3.33-6.21 MBq (90-168 μCi) of radiotracer formulated in 100 μL of saline at pH ~7. For binding specificity studies, a mouse was subcutaneously administered with a blocking dose of the known PSMA inhibitor N—[[[(S)-1-carboxy-3-methylbutyl]amino]carbonyl]-L-glutamic acid (ZJ43) (Olszewski et al., 2004) (50 mg/kg) at 30 min before the injection of $^{86}$Y-4, and another mouse was injected with $^{86}$Y-4 alone. At different time points, anesthetized individual mice were placed in the prone position on the scanner gantry and secured with medical tape while the anesthesia flow rate was increased to 0.8 L/min. Images were reconstructed using the FORE/2D-OSEM method (two iterations, 16 subsets) and included correction for radioactive decay, scanner dead time, and scattered radiation. Partial volume correction (PVC) was not performed. After each PET scan, a CT scan was acquired for anatomic co-registration. To facilitate PET and CT image co-registration, a special animal bed was employed which fits both the PET and CT scanners. The animals were under anesthesia and immobilized when moving between scanners as well as during both scans. The reconstructed PET and CT images were then manually co-registered through rigid transformation, by aligning natural landmarks (such as the animal limbs and the bed contour) using the AMIDE software (from sourceforge.net/amide). Data were displayed and analyzed using AMIDE.

Dynamic, whole-body PET and CT images were acquired on an eXplore VISTA small-animal PET (GE Healthcare, Little Chalfont, Buckinghamshire, UK) and an X-SPECT small SPECT/CT system (Gamma Medica Ideas, Northridge, Calif.), respectively.

*Papio anubis* (Baboon) PET Imaging of $^{86}$Y-6.

A male *Papio anubis* (8 y, 27.1 kg) was used to study the biodistribution of $^{86}$Y-6. The baboon was positioned supine during image acquisition. For attenuation correction a low-dose CT image was acquired immediately before the first and last PET images. PET and CT images were co-registered across time points using a Hermes workstation (Hermes Medical Solutions, Greenville, S.C.). Fourteen source organ contours were delineated on the CT with the aid of fused PET/CT images. Decay-corrected mean activity concentrations (Bq/g) were extracted for each source organ from the PET images. Contours were drawn on the PET images of the kidneys, renal cortices, and prostate. The decay-corrected total activity per organ quantified within the PET images had nearly one-to-one correspondence with the administered radioactivity for the first six time points (1 h or less), which confirmed that the administered radioactivity was fully accounted for on the PET images, after which the total amount was less than the administered amount due to voiding. The total amount of radioactivity quantified in each of the PET images was used to obtain the whole-body retention kinetics.

Nine static PET images were acquired at 5, 10, 15, 20, 35 min, 1, 2, 3.5 and 23 h after intravenous administration of 80.7 MBq (2.2 mCi) of $^{86}$Y-6 as a bolus. Images were acquired in 2D mode on a Discovery Rx VCT scanner (GE Healthcare).

Radiation Dosimetry:

For each time-point, the activity concentration (in Bq/cm$^3$) was measured in each of the 14 delineated organs and multiplied by the organ volume to obtain the total activity per time point per organ. The measured values were then decay-corrected and divided by the baboon organ mass, determined by the CT density and volume from the drawn contours, and the injected radioactivity to obtain the fraction of initial radioactivity per gram (FIA/g) for each time point and each organ. The baboon FIA/g values were then converted to human FIA (per organ) using the following equation (Schwartz et al., 2011; Woodard et al., 1975):

$$[FIA/\text{organ}]_{Human} = [FIA]_{Baboon} \cdot WBmass_{Baboon} \cdot \frac{\text{organ } mass_{Human}}{WBmass_{Human}} \quad (1)$$

where $WBmass_{Baboon} = 27.1$ kg and $WBmass_{Human} = 73.7$ kg.

That approach assumes that the concentration of activity in a particular tissue relative to the overall concentration in the whole body is preserved across species (i.e., organ concentration/total body concentration is the same for baboon and man). The resulting human FIA values were plotted as a function of time (nine data points) for each organ and fit to a bi-exponential expression:

$$FIA(t) = A1 \cdot e^{-(\lambda 1_{bio} \cdot t)} + A2 \cdot e^{-(\lambda 2_{bio} \cdot t)} \quad (2)$$

where A1, A2, $\lambda 1_{bio}$, and $\lambda 2_{bio}$ are fit parameters. The sum of A1 and A2 give the back-extrapolated, time-zero fraction of administered radioactivity in each organ, and $\lambda 1_{bio}$ and $\lambda 2_{bio}$ are the biological clearance constants. The equation for the time-integrated activity coefficient [TIAC, previously known as residence time (Bolch et al., 2009) for each source organ was obtained, as its name implies, by integrating equation (2) and introducing a physical decay term, $\lambda_\varphi$, which depends on the isotope used:

$$\tau(h) = \left( \frac{A1}{(\lambda 1_{bio} + \lambda_\varphi)} + \frac{A2}{(\lambda 2_{bio} + \lambda_\varphi)} \right). \quad (3)$$

TIACs were calculated for $^{90}$Y, $^{177}$Lu and $^{86}$Y, with their corresponding physical decay constants: $^{90}$Y $\lambda_\varphi$=0.01083 h$^{-1}$ (T$_{1/2}$=64.0 h); $^{177}$Lu $\lambda_\varphi$=0.00429 h$^{-1}$ (T$_{1/2}$=161.52 h) and $^{86}$Y $\lambda_\varphi$=0.04702 h$^{-1}$ (T$_{1/2}$=14.74 h), respectively voiding. Radiation absorbed doses were obtained by converting time-integrated activity to absorbed doses according to the MIRD absorbed fraction methodology (Bolch et al., 2009) through the use of the OLINDA/EXM software (Stabin et al., 2005). The TIAC for the urinary bladder was obtained using the MIRD bladder model implemented in OLINDA/EXM. Input to that model requires the whole-body TIAC, which was obtained from the equation FIA(t)=A. e$^{(-\lambda_{bio}t)}$ fitted to whole-body retention kinetics. The voiding interval was set to 2 h. The TIACs were then input into OLINDA/EXM (Stabin et al., 2005), and the resulting absorbed dose per unit of radioactivity obtained for the 14 organs. The specific kidney model in OLINDA/EXM was used to obtain the renal cortex dose values. The absorbed dose from organs external to the kidney was added to the renal cortex dose calculated from the internal kidney model. The specific prostate model was used for prostate self-dose, and external dose to the bladder was added as a surrogate for the whole body to prostate dose. The self-dose component of the absorbed dose per unit activity for the salivary glands was obtained using 3D-RD Monte Carlo (EGSnrc) and a human CT with delineated salivary glands. The cross-dose component was taken by assuming the same cross-dose for a like-sized organ (pancreas).

Measured activity concentration (in Bq/cm$^3$) values per time point per organ were decay-corrected and divided by the baboon organ mass, determined by the CT density and volume from the drawn contours, and the injected radioactivity to obtain the fraction of initial radioactivity per gram (FIA/g) for each time point and each organ. The baboon FIA/g values were then converted to human FIA (per organ) using the related equation (Olszewski et al., 2004; Schwartz et al., 2011). The resulting human FIA values were then plotted as a function of time and fit to a bi-exponential expression and the value for the time-integrated activity coefficient (TIAC, previously known as residence time (Woodard et al., 1975)) for each source organ was calculated. Radiation absorbed doses were obtained by converting time-integrated activity to absorbed doses according to the MIRD absorbed fraction methodology (Woodard et al., 1975) through the use of the OLINDA/EXM software (Bolch et al., 2009).

Data were expressed as mean±standard deviation (SD) calculated using Microsoft Excel (Microsoft Corporation, 2010). Prism software (GraphPAD) was used to determine statistical significance at the 95% confidence level, with a P≤0.05 considered significant.

Results

Compounds 4 and 5 were prepared using a combined solid and solution phase peptide synthesis strategy as shown in Schemes 4 and 5. Compounds 1 and 4 were prepared as previously reported (Banerjee, Pullambhatla, Byun, et al., 2011). Synthesis of DOTA-conjugated ligand 5 was performed using standard fluorenylmethoxycarbonyl (Fmoc) solid phase peptide synthesis (SPPS), starting from Fmoc-Lys(Boc)-Wang resin according to Scheme 5. Three phenylalanine residues were coupled with the resin-bound lysine followed by DOTA conjugation, after which the compound was cleaved from the resin by a 1/1 mixture of TFA/CH$_2$Cl$_2$ to produce 3 in moderate yield (~20%). The free ε-amine of lysine of 3 was then conjugated with 1 (Davis et al., 2009) to produce 5. Compound 6 was synthesized by reacting commercially available DOTA-Benzylisocyanate and N-Boc-1,4 diaminobutane in DMSO in the presence of diisopropylethylamine at 40° C. for 4 h, followed by removal of the Boc group to produce 7 in moderate yield after purification by HPLC. Compound 7 was then conjugated with 1 to produce 6 in good yield. Stable yttrium ($^{89}$Y) complexes were prepared by incubating conjugates 4-6 with an aqueous solution of YNO$_3$ at 95° C. as shown in Schemes 4-5. It is worth to mention that $^{86/89}$Y(III)-labeled compounds 4-5 contain three carboxylic acids coordinated to the metal making it overall neutral compound whereas [$^{86/89}$Y]6 has four coordinated carboxylic acids making an overall negatively charged compound. Radiotracers [$^{86}$Y] 4-6 were prepared by using a same general procedure, upon reaction with [$^{86}$Y]NO$_3$ at ligand concentrations of 10$^{-6}$ M in boiling water for 30 min at pH 5-6.

Scheme 4. Synthesis of 4-5 and [$^{86/89}$Y]4-5.

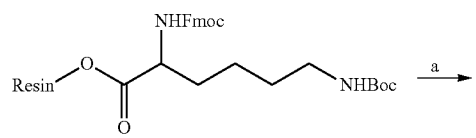

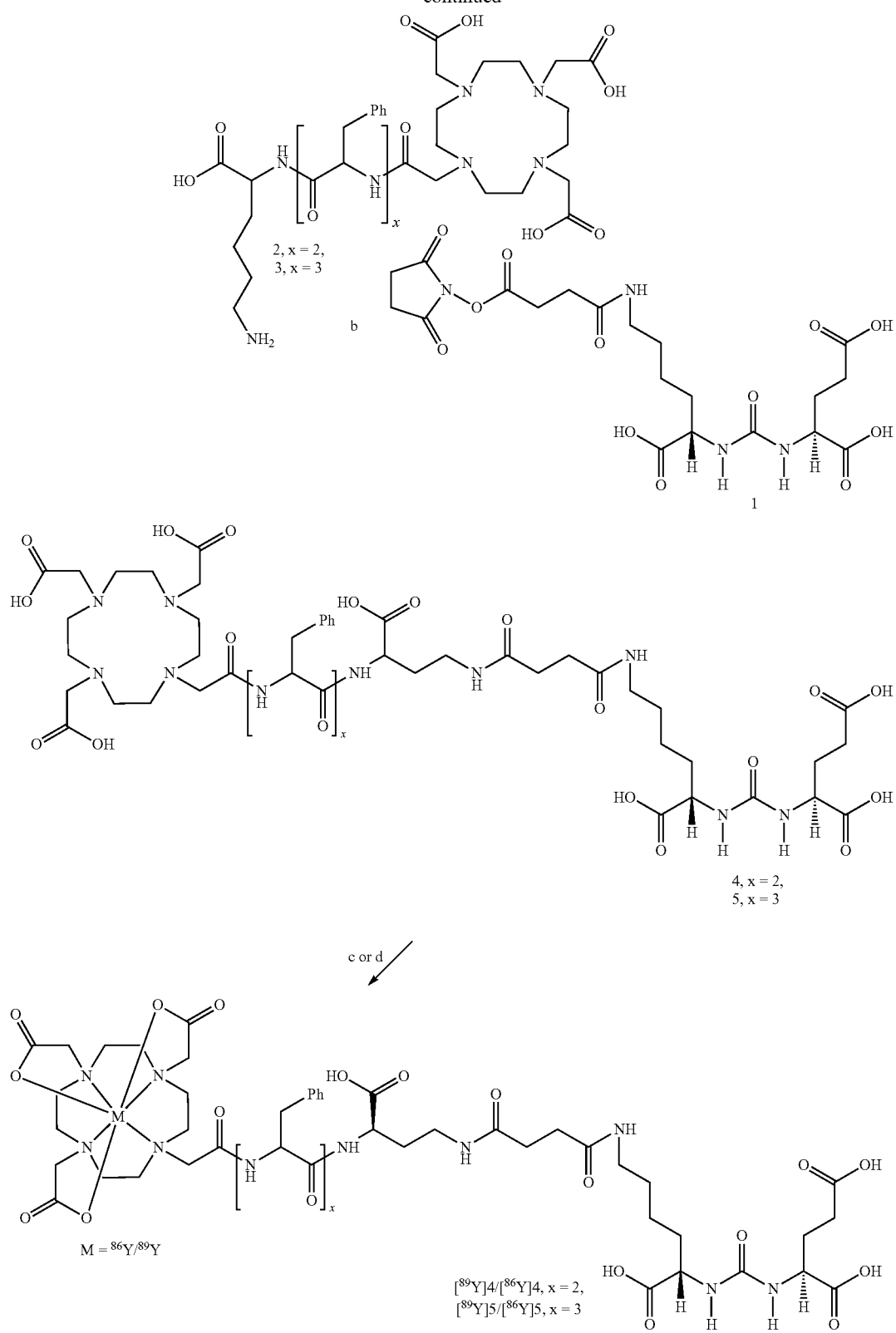
a. (i) 20% piperidine/DMF, (ii) Fmoc-Phe-OH, HOBT, HBTU, steps i-ii repeated 2 times for X = 2, and repeated 3 times for X = 3, (iii) 20% piperidine/DMF; (iv) DOTA-tris(tert-buty ester)-CO$_2$H, HOBT, HBTU, DIEA, (v) TFA/TES/H$_2$O (98/0.5/1.5);
b. DMSO/TEA, rt, c. Y(NO$_3$)$_3$/NaOAc, pH 5.5, 90° C., 20 min; d. 86Y(NO3)3/ascorbic acid/NaOAc, pH 5.5, 90° C., 20 min.

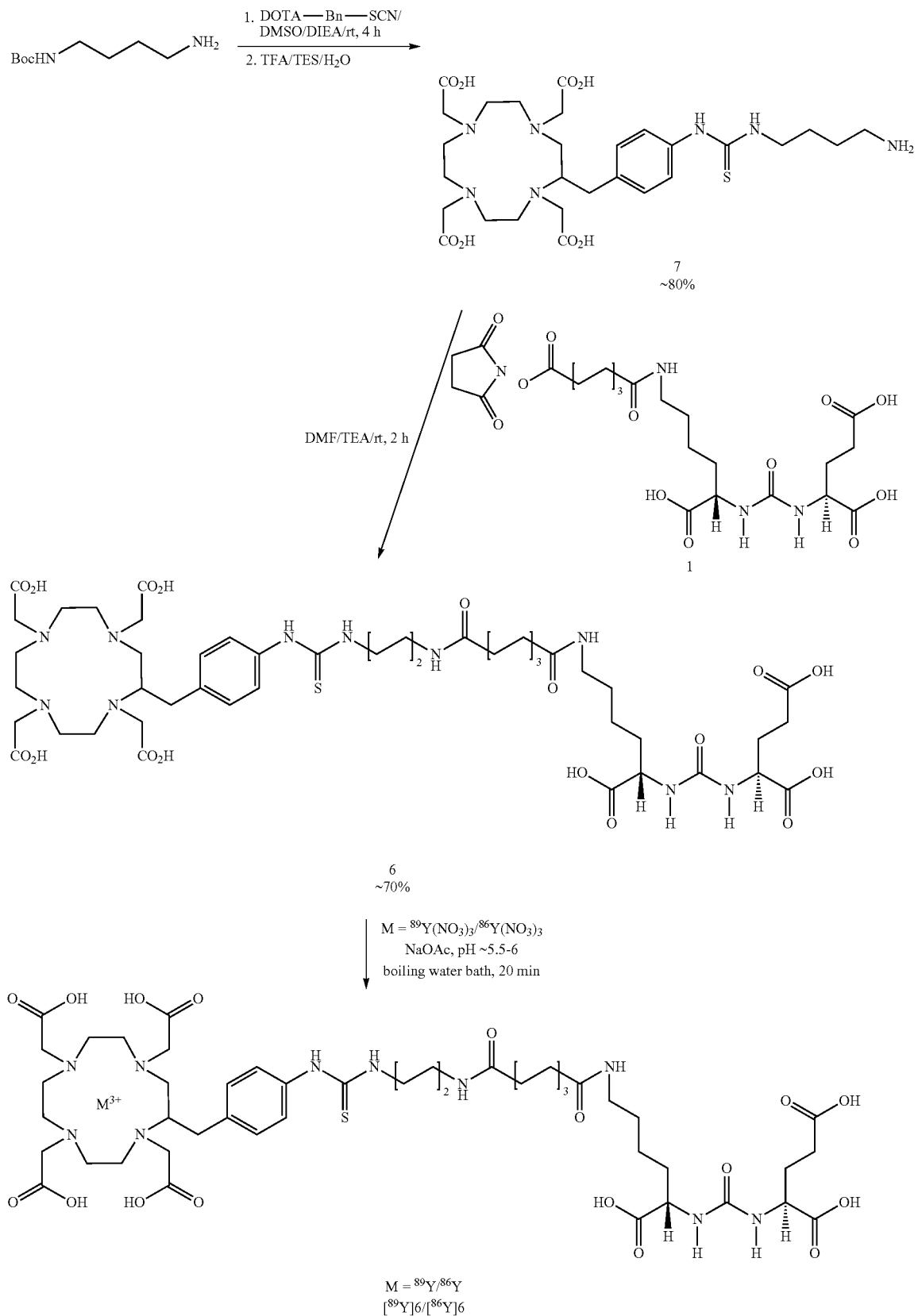

The chemical structures of the $^{86}$Y-labeled PSMA targeting compounds, $^{86}$Y-4, $^{86}$Y-5 and $^{86}$Y-6, are shown in FIG. 14. Radiolabeling of the target compounds proceeded in high yield (~90-97%) and radiochemical purity (>98%) with high specific radioactivity (>83.92 GBq/μmol (2.27 Ci/μmol)). All compounds displayed high binding affinity, with Ki values ranging from 0.10 to 4.69 nM (Table 2).

TABLE 2

PSMA inhibitory activities

|  | Ki [nM] | 95% CI of Ki |
|---|---|---|
| 4 | 0.41 | 0.34-0.56 |
| $^{89}$Y-4 | 0.36 | 0.2-0.51 |
| 5 | 3.12 | 1.7-5.60 |
| $^{89}$Y-5 | 0.10 | 0.04-0.32 |
| 6 | 1.80 | 0.83-3.92 |
| $^{89}$Y-6 | 2.99 | 1.91-4.69 |
| ZJ43 | 1.16 | 0.08-2.26 |

Small Animal PET Imaging:

Whole-body PET/CT images were obtained for $^{86}$Y-4, $^{86}$Y-5 and $^{86}$Y-6 (FIG. 18A, FIG. 18B, FIG. 18C, FIG. 19A, FIG. 20A, FIG. 20B and FIG. 20C). All three radiotracers enabled visualization of PSMA+PC-3 PIP tumor and kidneys (FIG. 18A, FIG. 18B and FIG. 18C), a known PSMA-expressing organ, at 2 h post-injection. Renal uptake of the radiotracers is partially due to the route of excretion of these agents as well as to specific uptake from the expression of PSMA in mouse proximal renal tubules (Stabin et al., 2005). Agent $^{86}$Y-5 demonstrated non-specific accumulation in the gastrointestinal tract, presumably due to the increased hydrophobicity from the three Phe residues on the linker moiety. PET-CT images of $^{86}$Y-4 were acquired at 1, 4 and 18 h post-injection considering the short biologic half-life of this class of low-molecular-weight compounds. Presence of the radiotracer in PSMA+PC-3 PIP tumor and kidneys and urinary bladder was observed up to 4 h (FIG. 19A). Radioactivity in bladder and kidneys cleared significantly by 18 h, although the PSMA+PC-3 PIP tumor retained some activity. As a further test of in vivo binding specificity, a blocking study of $^{86}$Y-4 was performed by pre-treating the animal with 50 mg/kg of the potent, selective PSMA inhibitor, ZJ43 (Silver et al., 1997). FIG. 19B demonstrates that ZJ43 was capable of blocking the binding of $^{86}$Y-4 not only within tumor but also within the renal cortex, another PSMA-expressing tissue (Stabin et al., 2005). FIG. 20A, FIG. 20B and FIG. 20C display PET-CT imaging for $^{86}$Y-6 at 0.5, 2 and 12 h post-injection. Significantly, $^{86}$Y-6 exhibited faster clearance of radioactivity from normal tissues and by 12 h post-injection radioactivity was largely cleared from kidneys, producing clear tumor-to-background contrast. Clear delineation of PSMA+PC-3 PIP tumor was achieved as early as at 15 min. Notably, $^{86}$Y-6 does not contain the additional phenylalanine moieties of $^{86}$Y-4 and $^{86}$Y-5, and utilizes a p-isothiocyanatobenzyl 1,4,7,10-tetraazacyclododecane-1,4,7,10-tetraacetic acid (DOTA) chelator, which adds an additional carboxylate to hold the metal strongly and decreases lipophilicity.

Biodistribution in Mice:

Based on the results of imaging, compounds $^{86}$Y-4 and $^{86}$Y-6 were further assessed in a standard biodistribution assay (Banerjee, Pullambhatla, Byun, et al., 2011). Tables 3 and 4 show the % ID/g uptake values in selected organs at 1, 2, 5 and 24 h post-injection. Both radiotracers showed PSMA-dependent binding in PSMA+PC-3 PIP tumor xenografts, with $^{86}$Y-4 demonstrating high tumor uptake at as early as 1 h post-injection (29.3±8.7% ID/g) with relatively slow clearance to 15.7±1.7% ID/g at 5 h and to 5.9±0.8% ID/g at 24 h post-injection. PSMA+PC-3 PIP tumor to PSMA– PC-3 flu tumor uptake ratios ranged from 89 at 1 h to a high of 229 at 24 h. Blood and normal tissues such as heart, liver, stomach and pancreas did not show significant uptake (~1% ID/g) and decreased below 0.02% ID/g after 24 h. PSMA+PC-3 PIP tumor-to-muscle ratios were also high, achieving a maximum value of 1,046 at 24 h. Kidney uptake was found expectedly high and peaked at 244.9±8.8% ID/g at 1 h and decreased to 1.5±0.7% ID/g by 24 h.

Table 4 shows the organ % ID/g uptake values for $^{86}$Y-6. Compound $^{86}$Y-6 quickly accumulated within the PSMA+PC-3 PIP tumor within 1 h after injection, with an uptake value of 26.6±1.9% ID/g. The radiotracer concentration continuously increased within PSMA+PC-3 PIP tumor to exhibit the highest uptake of 32.2±8.0% ID/g at 5 h post-injection. Tumor uptake remained high until 24 h post-injection. Normal organs such as blood, heart, liver, spleen, stomach, and pancreas exhibited low uptake at 1 h, which decreased to below 0.4% ID/g by 5 h. Renal uptake for $^{86}$Y-6, 86.5±13.6% ID/g and 54.0±9.2% ID/g at 1 h and 2 h respectively, was much lower than for $^{86}$Y-4.

TABLE 3

Biodistribution of $^{86}$Y-4 in mice (% ID/g)

|  | 1 H | 2 H | 5 H | 24 H |
|---|---|---|---|---|
| blood | 0.5 ± 0.2 | 0.1 ± 0.1 | 0.0 ± 0.0 | 0.0 ± 0.0 |
| heart | 0.3 ± 0.1 | 0.1 ± 0.0 | 0.0 ± 0.0 | 0.0 ± 0.0 |
| lung | 1.1 ± 0.2 | 0.3 ± 0.1 | 0.1 ± 0.0 | 0.0 ± 0.0 |
| liver | 0.2 ± 0.1 | 0.1 ± 0.0 | 0.1 ± 0.0 | 0.0 ± 0.0 |
| spleen | 5.1 ± 1.4 | 1.3 ± 0.5 | 0.2 ± 0.1 | 0.0 ± 0.0 |
| kidney | 245.0 ± 9.0 | 123.0 ± 48 | 23.0 ± 9.7 | 1.5 ± 0.7 |
| muscle | 0.5 ± 0.4 | 0.1 ± 0.1 | 0.1 ± 0.1 | 0.0 ± 0.0 |
| small intestine | 0.2 ± 0.0 | 0.1 ± 0.0 | 0.0 ± 0.0 | 0.0 ± 0.0 |
| large intestine | 0.3 ± 0.1 | 0.1 ± 0.0 | 0.1 ± 0.0 | 0.0 ± 0.0 |
| bladder | 1.5 ± 0.8 | 12.6 ± 12.5 | 3.6 ± 1. | 0.2 ± 0.2 |
| PC-3 PIP | 29.0 ± 8.7 | 21.6 ± 3.6 | 15.7 ± 1.7 | 5.9 ± 0.8 |
| PC-3 flu | 0.3 ± 0.1 | 0.1 ± 0.0 | 0.1 ± 0.0 | 0.0 ± 0.0 |
| PIP: flu | 89 | 164 | 156 | 229 |
| PIP: blood | 55 | 198 | 624 | 2,352 |
| PIP: muscle | 54 | 140 | 191 | 1,046 |

TABLE 4

Biodistribution of $^{86}$Y-6 in mice (% ID/g)

|  | 1 H | 2 H | 5 H | 24 H |
|---|---|---|---|---|
| blood | 0.6 ± 0.0 | 0.2 ± 0.0 | 0.1 ± 0.0 | 0.0 ± 0.0 |
| heart | 0.3 ± 0.0 | 0.1 ± 0.0 | 0.0 ± 0.0 | 0.0 ± 0.0 |
| lung | 1.1 ± 0.2 | 0.5 ± 0.1 | 0.2 ± 0.0 | 0.1 ± 0.0 |
| liver | 0.3 ± 0.0 | 0.2 ± 0.0 | 0.1 ± 0.0 | 0.1 ± 0.0 |
| stomach | 0.3 ± 0.1 | 0.14 ± 0.01 | 0.11 ± 0.01 | 0.05 ± 0.09 |
| pancreas | 0.3 ± 0.1 | 0.23 ± 0.2 | 0.08 ± 0.04 | 0.01 ± 0.01 |
| spleen | 3.0 ± 0.7 | 1.31 ± 0.7 | 0.36 ± 0.12 | 0.11 ± 0.05 |
| fat | 0.6 ± 0.5 | 1.87 ± 3.44 | 0.12 ± 0.17 | 0.01 ± 0.01 |
| kidney | 87.0 ± 14.0 | 54.0 ± 9.0 | 15.6 ± 4.1 | 4.8 ± 0.8 |
| muscle | 0.8 ± 1.2 | 0.25 ± 0.2 | 0.0 ± 0.0 | 0.0 ± 0.0 |
| small intestine | 0.3 ± 0.1 | 0.1 ± 0.0 | 0.07 ± 0.02 | 0.02 ± 0.02 |
| large intestine | 0.4 ± 0.3 | 0.2 ± 0.1 | 0.1 ± 0 | 0.0 ± 0.0 |
| bladder | 6.0 ± 3.9 | 5.5 ± 3.7 | 0.8 ± 0.1 | 0.4 ± 0.3 |
| PC-3 PIP | 26.6 ± 1.9 | 29.2 ± 2.3 | 32.2 ± 8.0 | 15.8 ± 6.4 |
| PC-3 flu | 0.4 ± 0.1 | 0.2 ± 0.0 | 0.2 ± 0.1 | 0.1 ± 0.1 |
| PIP: flu | 66 | 152 | 183 | 130 |

TABLE 4-continued

Biodistribution of $^{86}$Y-6 in mice (% ID/g)

|  | 1 H | 2 H | 5 H | 24 H |
|---|---|---|---|---|
| PIP: blood | 44 | 145 | 378 | 620 |
| PIP: muscle | 33 | 115 | 921 | 3,010 |

Baboon PET Imaging and Pharmacokinetics of $^{86}$Y-6:

FIG. 21A and FIG. 21B depict the PET study, where radiotracer is seen in liver, salivary glands, kidney and bladder. For whole kidney, renal cortex and prostate, contours were drawn on each PET image for quantification. All organs showed two-phase (rapid and slow) biological clearance. Kidneys had the highest uptake at about 25 min post-injection (8% ID/g). Sixty-eight percent of the radioactivity seen in the kidneys was cleared with a biological half-life of about 1 h (0.84 h) and the remaining radioactivity was cleared with a biological half-life of 16.6 h. The majority (66%) of the radioactivity in the renal cortex was cleared with a biological half-life of 1.1 h and the remaining radioactivity was cleared with a biological half-life of about 19 h. Significant uptake and retention were seen in liver and salivary glands, although milder compared to PET scans of patients imaged with $^{68}$Ga-labeled PSMA-targeted agents and $^{124/131}$I-MIP-1095 (Zechmann et al., 2014). Table 5 gives the summary of the biological clearance kinetics of all organs. The TIACs used in the dose calculations are listed in Table 6.

TABLE 5

[$^{86}$Y]6 fitted pharmacokinetic parameters

| Organs | Fitted parameters | (% ID) | Half-life (h) |
|---|---|---|---|
| Kidneys | A1 | 6.36 | 0.84 |
|  | A2 | 2.98 | 16.62 |
| Renal cortex | A1 | 4.23 | 1.10 |
|  | A2 | 2.16 | 19.19 |
| Brain | A1 | 0.53 | 0.71 |
|  | A2 | 0.11 | 8.71 |
| Lungs | A1 | 2.78 | 0.42 |
|  | A2 | 1.27 | 6.29 |
| Heart | A1 | 1.55 | 0.29 |
|  | A2 | 0.29 | 6.49 |
| Liver | A1 | 4.77 | 0.38 |
|  | A2 | 1.52 | 7.71 |
| Stomach | A1 | 0.15 | 0.46 |
|  | A2 | 0.09 | 6.14 |
| Spleen | A1 | 0.12 | 1.49 |
|  | A2 | 0.04 | 18.74 |
| Small intestine | A1 | 0.24 | 0.26 |
|  | A2 | 0.10 | 10.17 |
| Large intestine | A1 | 0.45 | 0.25 |
|  | A2 | 0.30 | 5.97 |
| Muscle | A1 | 14.98 | 1.98 |
|  | A2 | 0.56 | 69.31 |
| Pancreas | A1 | 0.24 | 0.66 |
|  | A2 | 0.05 | 10.60 |
| WB retention | A1 | 100.00 | 5.62 |
| Salivary glands | A1 | 0.30 | 1.56 |
|  | A2 | 0.08 | 4.47 |
| Prostate | A1 | 0.02 | 0.67 |
|  | A2 | 0.02 | 5.58 |

TABLE 6

Time-integrated activity coefficients (residence time)

| | Time-integrated activity coefficient (MBq-h/MBq) | | |
|---|---|---|---|
| Source Organs | $^{86}$Y | $^{177}$Lu | $^{90}$Y |
| Brain | 1.41E−02 | 1.89E−02 | 1.79E−02 |
| Small intestine | 9.31E−03 | 1.43E−02 | 1.32E−02 |
| Stomach | 6.44E−03 | 8.46E−03 | 8.06E−03 |
| ULI | 1.99E−02 | 2.64E−02 | 2.51E−02 |
| Heart contents | 2.55E−02 | 3.30E−02 | 3.15E−02 |
| Kidneys | 4.08E−01 | 7.24E−01 | 6.43E−01 |
| Renal cortex | 3.23E−01 | 6.02E−01 | 5.27E−01 |
| Liver | 1.37E−01 | 1.88E−01 | 1.77E−01 |
| Lungs | 9.70E−02 | 1.28E−01 | 1.22E−01 |
| Muscle | 4.76E−01 | 8.15E−01 | 6.85E−01 |
| Pancreas | 6.37E−03 | 9.00E−03 | 8.42E−03 |
| Spleen | 7.41E−03 | 1.29E−02 | 1.15E−02 |
| Ur. bladder contents | 7.41E−01 | 1.00 | 9.54E−01 |
| Prostate | 1.15E−03 | 1.48E−03 | 1.42E−03 |
| Salivary Glands | 4.45E−02 | 4.97E−02 | 4.88E−02 |
| Remainder | 3.64 | 4.84 | 4.74 |

Organ Absorbed Doses:

Table 7 provides a detailed list of the organ absorbed doses, expressed in units of mGy/MBq, for $^{86}$Y, $^{90}$Y/$^{177}$Lu. For all isotopes, the renal cortex received the highest absorbed dose per unit activity. Accordingly, it is likely that the renal cortex would be the dose-limiting organ for therapeutic radiometals in the context of patient-specific absorbed dose treatment planning (Baechler et al., 2012; Hobbs et al., 2009), followed by the bladder. For the diagnostic isotope $^{86}$Y, an effective dose of 0.099 mSv/MBq was also calculated in OLINDA/EXM.

TABLE 7

Organ absorbed doses in the Reference Adult Male based on baboon PET imaging data

| | Organ doses (mGy/MBq) | | |
|---|---|---|---|
| Target organs | $^{86}$Y | $^{177}$Lu | $^{90}$Y |
| Adrenals | 8.62E−02 | 6.96E−03 | 3.46E−02 |
| Brain | 2.30E−02 | 1.48E−03 | 6.79E−03 |
| Breasts | 4.52E−02 | 6.08E−03 | 3.46E−02 |
| Gallbladder wall | 7.88E−02 | 6.79E−03 | 3.46E−02 |
| LLI wall | 9.61E−02 | 7.06E−03 | 3.46E−02 |
| Small intestine | 8.72E−02 | 8.30E−03 | 4.29E−02 |
| Stomach wall | 6.69E−02 | 7.88E−03 | 3.46E−02 |
| ULI wall | 8.56E−02 | 1.16E−02 | 6.29E−02 |
| Heart wall | 6.70E−02 | 9.54E−03 | 5.33E−02 |
| Kidneys | 4.03E−01 | 2.10E−01 | 1.13 |
| Renal cortex | 4.24E−01 | 2.45E−01 | 1.19 |
| Liver | 7.19E−02 | 9.37E−03 | 4.99E−02 |
| Lungs | 5.98E−02 | 1.16E−02 | 6.57E−02 |
| Muscle | 5.47E−02 | 3.26E−03 | 1.32E−02 |
| Ovaries | 9.48E−02 | 7.05E−03 | 3.46E−02 |
| Pancreas | 8.09E−02 | 9.34E−03 | 4.64E−02 |
| Red marrow | 6.29E−02 | 5.04E−03 | 2.41E−02 |
| Osteogenic cells | 7.19E−02 | 1.94E−02 | 5.26E−02 |
| Skin | 3.97E−02 | 6.01E−03 | 3.46E−02 |
| Spleen | 7.23E−02 | 7.16E−03 | 1.64E−02 |
| Testes | 7.23E−02 | 6.56E−03 | 3.46E−02 |
| Thymus | 5.38E−02 | 6.29E−03 | 3.46E−02 |
| Thyroid | 5.07E−02 | 6.26E−03 | 3.46E−02 |
| Urinary bladder wall | 6.17E−01 | 2.14E−01 | 1.25 |
| Uterus | 1.34E−01 | 7.76E−03 | 3.46E−02 |
| Prostate | 7.64E−02 | 7.94E−03 | 4.78E−02 |
| Salivary glands | 1.78E−01 | 4.76E−02 | 2.79E−01 |

Discussion

Three $^{86}$Y-labeled, PSMA-targeted agents have been synthesized and evaluated in order to undertake non-human primate dosimetry. Those compounds contain a DOTA- or DOTA mono-amide chelated radiometal attached to the targeting urea similar to others that have been published (Banerjee et al., 2010; Banerjee, Pullambhatla, Byun, et al., 2011). DOTA and its derivatives have been the focus because they can be used both for PET ($^{86}$Y) or radiopharmaceutical therapy ($^{90}$Y). It has been documented that pharmacokinetics are dependent on the radiometal chelator used, including those for compounds specifically designed to bind to PSMA. Without wishing to be bound to any one particular theory, it is believed that is primarily attributed to the overall charge of the radioligand and the stability of the metal chelate complexes. Specifically, in a previous report of $^{68}$Ga-labeled PSMA-binding DOTA conjugated agents, $^{68}$Ga-4 demonstrated the fastest clearance from normal tissues, including kidneys (Banerjee et al., 2010). However, in the current study it was observed that $^{86}$Y-4 exhibited unexpectedly higher renal uptake. Evaluation of $^{86}$Y-6 demonstrated the desired lower kidney uptake and higher tumor retention required for radiotherapy and was subsequently selected for quantitative PET imaging in a baboon for dosimetry measurements.

The binding specificity study (FIG. 19B) indicated that at 1 hour nearly all renal binding of $^{86}$Y-4 was specific rather than due to excretion. Evidence suggests that more organized and rapid blood flow in renal parenchyma compared to tumors may account for longer tumor rather than renal retention for many of these agents. While PSMA-binding affinity is one factor that likely determines tumor versus renal uptake, other factors, such as lipophilicity, charge, plasma protein binding, and molecular weight, likely also play significant roles. The estimated renal cortex doses of 1.19 mGy/MBq for $^{90}$Y and 0.245 mGy/MBq for $^{177}$Lu compare favorably with the values of 1.97 mGy/MBq for $^{90}$Y and 0.45 mGy/MBq for $^{177}$Lu calculated in a report involving peptide receptor radiation therapy (Baechler et al., 2012), where renal cortex was the dose limiting organ.

The commonly used and clinically implemented chelating agent DOTA was used for all three radioligands because, DOTA, and many DOTA derivatives are known to form kinetically and thermodynamically stable complexes. The Corresponding Y(III)-complex has been shown in many cases to be stable in vivo, a desirable trait for a chelator. Significantly, DOTA is also reported to form stable complexes with an array of trivalent metal ions including lanthanides, for example, $^{177}$Lu(III), and actinides, for example, $^{225}$Ac(III), which are chemically disparate to $^{86}$Y(III). Moreover, PSMA-binding urea-based agents are stable under the radiolabeling conditions employed for DOTA.

Recently, $^{90}$Y or $^{177}$Lu-labeled versions of the PSMA-targeted monoclonal antibody J591 demonstrated promising results in Phase I and II clinical trials (Bander et al., 2005; Tagawa, Akhtar, et al., 2013; Tagawa, Milowsky, et al., 2013). In those cases, $^{111}$In-labeled antibody was used for dosimetry calculations (Vallabhajosula et al., 2005). Although those radiolabeled monoclonal antibodies hold potential for tumor detection and therapy, their modest tumor targeting and a relatively high absorbed dose to red marrow mitigate against routine clinical use. As an alternate approach, early clinical results using $^{131}$I-labeled PSMA-targeted, urea-based small-molecules exhibited high dose delivery to malignant foci (Zechmann et al., 2014). In those published studies, the salivary glands showed the highest absorbed doses (4.62 mGy/MBq) followed by both liver (1.47 mGy/MBq) and kidneys (1.45 mGy/MBq) (Zechmann et al., 2014). It is probable that a significant contributor to the salivary gland absorbed dose is free iodine uptake, as also evidenced by the relatively high (0.91 mGy/MBq) thyroid absorbed dose, which does not occur in the current study. In general, the clearance rates from normal organs are more rapid for $^{86}$Y-6 than for the published results (Zechmann et al., 2014), with the exception of the kidneys.

In summary, biodistribution and dosimetry results suggest that $^{86}$Y-6 is a promising candidate for quantitative PET imaging of PSMA-expressing tumors, and may provide a suitable imaging surrogate for planning and monitoring PSMA-targeted $^{90}$Y-, $^{177}$Lu-based radiopharmaceutical therapy.

Example 4

$^{177}$Lu-SR-VI-71, $^{203}$Pb-SR-VI-71 and $^{203}$Pb-SR-IX-11 for PSMA-Based Targeted Radionuclide Therapy FIG. 24, cell uptake study using 0.01-10 µCi of $^{177}$Lu-SRVI71, demonstrated high uptake in PSMA+ PIP and negligible uptake in PSMA− flu tumor. In addition, internalization study revealed that ~44% of total cell associated radioactivity was internalized. Moreover, ~90% blockade in PSMA+ cells was observed upon co-incubation of 10 µM of N-[[[(1S)-1-Carboxy-3-methylbutyl]amino]carbonyl]-L-glutamic acid (ZJ43), a specific inhibitor of PSMA further confirming the excellent specificity of the agent (FIG. 23). In vivo evaluation was performed in standard PSMA+ PIP and PSMA− flu mouse xenografts and by performing SPECT imaging with a VECT or instrument with an extra ultra-high sensitivity mouse collimator as disclosed FIG. 25A, FIG. 25B and FIG. 25C. Highest accumulation of radioactivity was found in PSMA+ PIP tumor at all time-points. Other visible organs are the kidneys and bladder. Biodistribution studies at 2 h (59.1±12.8% ID/g) and at 24 h (40.6±5.8 ID/g) (n=4) indeed revealed high uptake and retention in PSMA+ tumor with high specificity (PIP:flu at ~180 at 2 h). Initial kidney uptake was high 89.3±28.9% at 2 h followed by rapidly clearance within 24 h (6.29±3.4% ID/g).

TABLE 8

Tissue Biodistribution of $^{177}$Lu-SR-VI-71

|  | 3 h | 24 h | 48 h | 72 h | 96 h |
|---|---|---|---|---|---|
| Blood | 0.14 ± 0.04 | 0.03 ± 0.03 | 0.03 ± 0.03 | 0.01 ± 0.01 | 0.00 ± 0.00 |
| heart | 0.09 ± 0.04 | 0.04 ± 0.00 | 0.02 ± 0.00 | 0.03 ± 0.01 | 0.01 ± 0.00 |
| lung | 0.62 ± 0.31 | 0.25 ± 0.026 | 0.06 ± 0.04 | 0.03 ± 0.02 | 0.05 ± 0.01 |
| liver | 0.31 ± 0.25 | 0.38 ± 0.35 | 0.11 ± 0.07 | 0.05 ± 0.03 | 0.04 ± 0.0 |
| spleen | 1.83 ± 0.38 | 0.74 ± 0.64 | 0.17 ± 0.05 | 0.09 ± 0.08 | 0.06 ± 0.03 |
| kidney | 53.66 ± 9.64 | 4.35 ± 0.41 | 2.35 ± 0.62 | 2.59 ± 1.10 | 1.44 ± 0.11 |

TABLE 8-continued

Tissue Biodistribution of $^{177}$Lu-SR-VI-71

|  | 3 h | 24 h | 48 h | 72 h | 96 h |
| --- | --- | --- | --- | --- | --- |
| muscle | 0.24 ± 0.14 | 0.04 ± 0.00 | 0.02 ± 0.00 | 0.01 ± 0.01 | 0.01 ± 0.0 |
| SI | 0.23 ± 0.12 | 0.10 ± 0.05 | 0.04 ± 0.01 | 0.05 ± 0.03 | 0.01 ± 0.00 |
| salivary gland | 0.42 ± 0.09 | 0.07 ± 0.08 | 0.10 ± 0.04 | 0.09 ± 0.04 | 0.06 ± 0.02 |
| PIP | 41.46 ± 7.88 | 27.52 ± 1.19 | 16.99 ± 2.65 | 15.63 ± 4.62 | 9.04 ± 1.72 |
| Flu | 0.14 ± 0.03 | 0.09 ± 0.01 | 0.05 ± 0.00 | 0.04 ± 0.00 | 0.03 ± 0.0 |

TABLE 9

Tissue Biodistribution of $^{203}$Pb-SR-VI-71

|  | 1 H | 2 H | 4 H | 24 H |
| --- | --- | --- | --- | --- |
| Blood | 0.60 ± 0.05 | 0.31 ± 0.04 | 0.24 ± 0.02 | 0.21 ± 0.02 |
| heart | 0.30 ± 0.03 | 0.14 ± 0.06 | 0.09 ± 0.01 | 0.07 ± 0.01 |
| lung | 1.20 ± 0.19 | 0.64 ± 0.14 | 0.28 ± 0.04 | 0.16 ± 0.01 |
| liver | 1.09 ± 0.07 | 1.01 ± 0.21 | 0.92 ± 0.09 | 0.64 ± 0.04 |
| stomach | 0.30 ± 0.04 | 0.15 ± 0.03 | 0.13 ± 0.03 | 0.07 ± 0.01 |
| pancreas | 0.49 ± 0.09 | 0.29 ± 0.05 | 0.24 ± 0.05 | 0.09 ± 0.06 |
| spleen | 5.07 ± 1.68 | 1.59 ± 0.58 | 0.72 ± 0.16 | 0.24 ± 0.02 |
| fat | 0.77 ± 0.29 | 0.31 ± 0.22 | 0.31 ± 0.18 | 0.05 ± 0.06 |
| kidney | 75.18 ± 9.94 | 39.35 ± 7.28 | 22.75 ± 6.22 | 7.01 ± 0.80 |
| muscle | 0.22 ± 0.14 | 0.22 ± 0.07 | 0.06 ± 0.02 | 0.04 ± 0.03 |
| Sm intestine | 0.31 ± 0.05 | 0.23 ± 0.04 | 0.15 ± 0.04 | 0.04 ± 0.03 |
| salivary gland | 1.78 ± 0.69 | 0.93 ± 0.07 | 0.29 ± 0.02 | 0.10 ± 0.05 |
| bladder | 5.96 ± 2.24 | 10.40 ± 3.21 | 1.94 ± 0.49 | 0.31 ± 0.16 |
| PC-3 PIP | 41.88 ± 7.60 | 38.14 ± 6.30 | 34.74 ± 7.37 | 27.92 ± 7.01 |
| PC-3 flu | 0.43 ± 0.11 | 0.29 ± 0.14 | 0.20 ± 0.06 | 0.14 ± 0.01 |
| PIP/flu | 98 | 130 | 178 | 194 |

TABLE 10

Tissue Biodistribution of $^{203}$Pb-SR-IX-11 (n = 2) and $^{203}$Pb-SR-VI-71 (n = 4) at 2 h

|  | $^{203}$Pb-SR-IX-11 | $^{203}$Pb-SR-VI-71 |
| --- | --- | --- |
| Blood | 0.07 ± 0.01 | 0.31 ± 0.04 |
| heart | 0.07 ± 0.01 | 0.14 ± 0.06 |
| lung | 0.24 ± 0.03 | 0.64 ± 0.14 |
| liver | 0.21 ± 0.01 | 1.01 ± 0.21 |
| stomach | 0.12 ± 0.00 | 0.15 ± 0.03 |
| pancreas | 0.06 ± 0.00 | 0.29 ± 0.05 |
| spleen | 0.25 ± 0.1 | 1.59 ± 0.58 |
| fat | 1.54 ± 1.64 | 0.31 ± 0.22 |
| kidney | 3.61 ± 0.81 | 39.35 ± 7.28 |
| muscle | 0.78 ± 0.83 | 0.22 ± 0.07 |
| sm intestine | 0.25 ± 0.15 | 0.23 ± 0.04 |
| salivary gland | 0.35 ± 0.10 | 0.93 ± 0.07 |
| bladder | 8.64 ± 0.77 | 10.40 ± 3.21 |
| PC-3 PIP | 21.64 ± 1.23 | 38.14 ± 6.30 |
| PC-3 flu | 0.19 ± 0.04 | 0.29 ± 0.14 |
| PIP: flu | 114 | 130 |

These results are quite promising with respect to the feasibility to prepare such low-molecular-weight theranostic agents with desired pharmacokinetics for radionuclide therapy. The data further support that this class of LMW agents can be effectively internalized upon binding with PSMA.

Example 5

Synthesis and Use of ZCP-01 and Related Agents for PSMA-Based Targeted Radionuclide Therapy Overview The preparation and use of PSMA binding ureas conjugated to chelated radiometals via various linking groups for imaging and possible radiotherapy of PSMA expressing tumors have been described in several patent and publication (Banerjee, et al., 2008; Banerjee, et al., 2010; Banerjee, et al., 2011; Banerjee, et al., Oncotarget 2011; Banerjee, et al., 2013; Banerjee, et al., 2014) as well as in the present patent application. PSMA inhibitors built upon novel lysine-carbamate scaffolds oxypentanedioic acid (OPA) corresponding to a carbamate scaffold and amino-pentanedioic acid (NPA) corresponding to a "reverse" carbamate scaffold, including F-18 labeled analogs, as disclosed on FIG. 29, have been recently developed. F-18 labeled NPA and OPA compounds demonstrated selective uptake in PSMA positive tumor mouse xenografts.

ZCP-01, a DOTA-PEG-linked lysine OPA carbamate for complexing radiometals for imaging and radiotherapy of PSMA positive tumors and tissues has been synthetized as an example. A broad range of metal chelating ligands and linkers previously disclosed in Patent Applications Nos. WO 2009/002529 A2 and WO2010/108125A2 for use with ureas can be attached to the OPA and NPA scaffolds to provide novel radiolabeled agents for imaging and/or radiotherapy of prostate cancer.

Material and Methods (18S,22S)-2,12,20-trioxo-1-(4,7,10-tris(carboxymethyl)-1,4,7,10-tetraazacyclododecan-1-yl)-6,9,21-trioxa-3,13,19-triazatetracosane-18,22,24-tricarboxylic acid, ZCP-01

Referring to scheme 7, to a solution of compound 4 (8.5 mg, 0.015 mmol in 200 μL DMSO) was added diisopropylethyl amine (27 μL, 0.255 mmol) and followed by slow addition of DOTA-NHS (15.2 mg, 0.023 mmol, in 200 μL DMSO) and the resulting solution was kept stirring at room temperature for 2 h. The solution was then diluted with water and purified by HPLC. HPLC Method: Phenomenex $C_{18}$ Luna, 10 mm*250 mm, flow rate: 8 ml/min, λ: 200 nm, 220 nm, solvent $H_2O$ and $CH_3CN$ (0.1% TFA in each). A gradient method; 0-20 min, 100/0 $H_2O/CH_3CN$ to 80/20 $H_2O/CH_3CN$; 20-30 min 80/20 $H_2O/CH_3CN$ to 0/100 $H_2O/CH_3CN$; 31 min 100/0 $H_2O/CH_3CN$. HPLC Retention time ($t_r$)=16 min. ESI-MS: 954 (M+H). Yield: 9.4 mg after HPLC purification (~65.7%).

Preparation of $^{113/115}$In-ZPC-01

To a solution of ZPC-01 (5 mg, 5.24 μmol in 500 μL 0.5 M NaOAc, pH 6.8) was added 50 μL of InNO3 (0.5 M), and the mixture (pH 6) was incubated for 30 min at 90° C. A solution of EDTA (200 μL, 30 mM, pH 6.0) was added, and the reaction mixture was incubated for 10 min at 40° C. to complex unreacted indium (III). The resulting compound was purified by HPLC (same as ZPC-01), concentrated by evaporation and lyophilized. ESI-MS:1066 [M+H]$^+$. Calculated for $C_{39}H_{64}InN_7O_{20}$, 1065.79.

Preparation of $^{111}$In-ZPC-01.

1.0 μl of $^{111}$InCl$_3$ (1 mCi) in 0.1 N HCl was added to 20 μl of 1 mM Ourea-PEG-DOTA in 0.2M NaOAc. The pH of the mixture was ~4.0. Then, 20 μl 0.2M NaOAc to adjust the pH-6. The mixture was kept at 50° C. for an hour and purified by radio-HPLC using an isocratic method containing a mobile phase 90% water (containing 0.1% TFA) and 10% $CH_3CN$ (0.1% TFA); Flow rate: 1.0 mL/min; λ: 200 nm, and a $C_{18}$ column (25×4.6 mm), Varian microsob-MV 100-5. Radiolabeled [$^{111}$In]ZPC-01 was eluted at 14.9 min whereas unlabeled chelating agent was eluted at 32 min.

Scheme 7

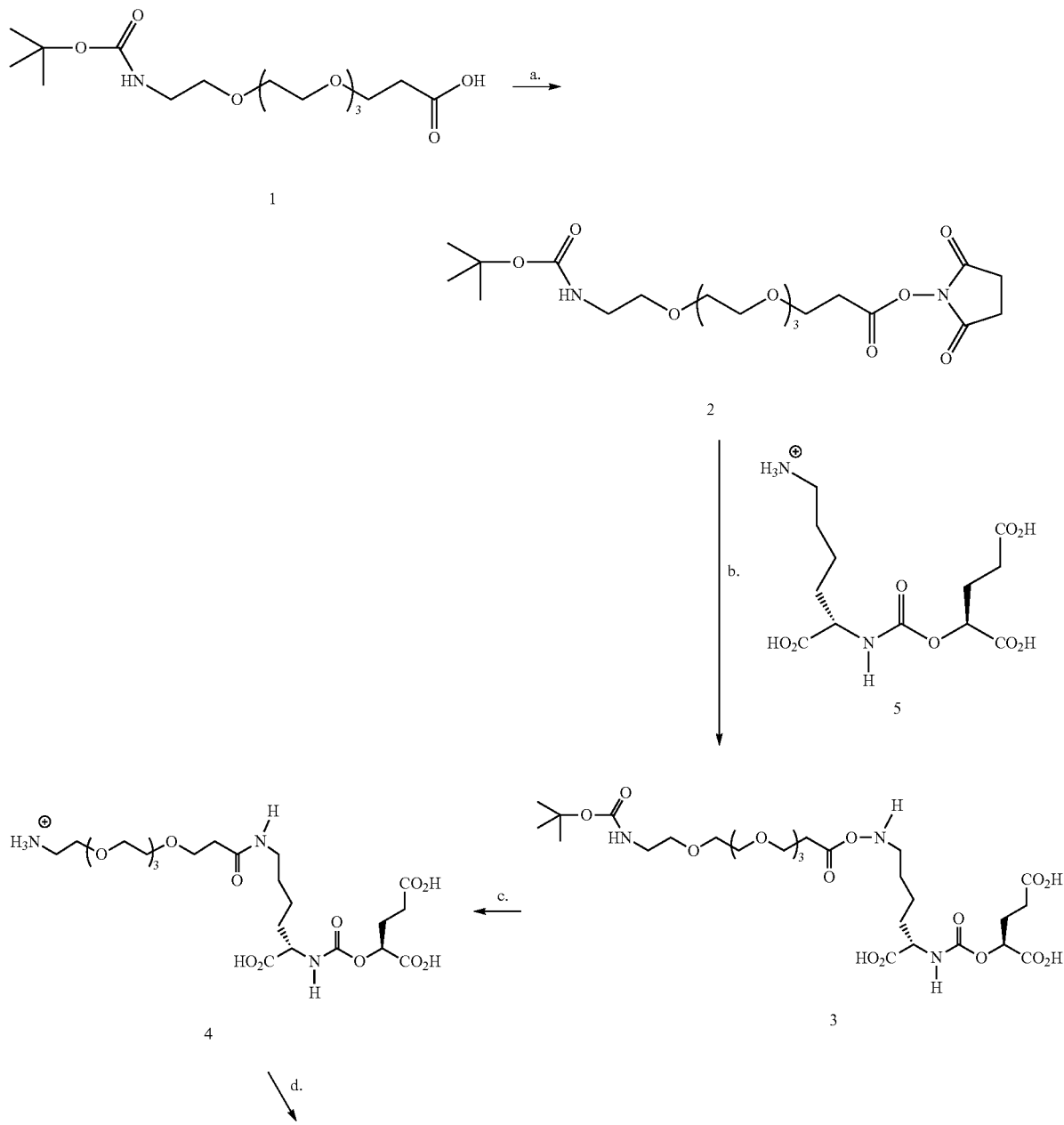

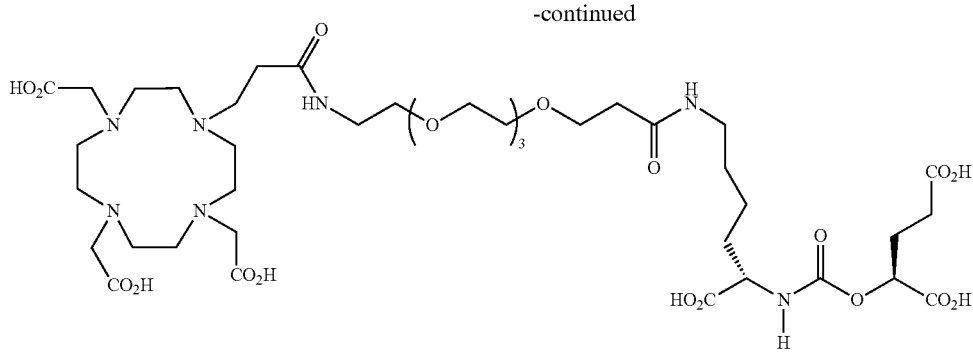

ZCP-01 a. DCC, N-hydroxysuccinimide, CH₂Cl₂; b. diisopropylethylamine, DMSO; TFA/water;
d. DO3A-NHS (Commerically available form Macrocylics)

Results

ZCP-01 and [In]-ZCP-01 displayed high-binding affinity, with Ki values ranging from 17.82 nM to 58.21 nM and 0.29 µM to 0.92 µM respectively (Table 8).

TABLE 11

PSMA inhibition data for ZCP-01 and [In]-ZCP-01

|  | In-ZCP-01 | ZCP-01 | ZJ43 |
|---|---|---|---|
| EC50 | 89 nM-291 nM | 1.43 µM-4.62 µM | 0.99 nM-2.40 nM |
| KI | 17.82 nM to 58.21 nM | 0.29 µM to 0.92 µM | 0.20 nM to 0.48 nM |
| 95% Confidence Intervals | 0.96 | 0.97 | 0.97 |

In vivo SPECT imaging of [In]-ZCP-01 was performed on mice bearing PSMA+PC3 PIP and PSMA−PC3 flu tumor xenografts implanted subcutaneously in the right and left flanks respectively, after the intravenous injection of [$^{111}$In]-ZCP-01 as shown on FIG. 34A, FIG. 34B and FIG. 34C. However, [$^{111}$I]-ZCP-01 enables visualization of PSMA+PC3 PIP tumor and kidneys, a known PSMA-expressing organ, at 2 h and 4 h post-injection, while the flu tumor received non-specific uptake. By 24 h-post-injection radioactivity was largely cleared from tumor and kidneys.

These results are quite promising with respect to the feasibility to prepare such low-molecular-weight theranostic agents with desired pharmacokinetics for the imaging and radiotherapy of tumors.

REFERENCES

All publications, patent applications, patents, and other references mentioned in the specification are indicative of the level of those skilled in the art to which the presently disclosed subject matter pertains. All publications, patent applications, patents, and other references are herein incorporated by reference to the same extent as if each individual publication, patent application, patent, and other reference was specifically and individually indicated to be incorporated by reference. It will be understood that, although a number of patent applications, patents, and other references are referred to herein, such reference does not constitute an admission that any of these documents forms part of the common general knowledge in the art.

International PCT Patent Application Publication No. PCT/US2008/007947 to Pomper, M. G., Ray, S., Mease, R. C., Foss, C. for Labeled inhibitors of prostate specific membrane antigen (PSMA), biological evaluation, and use as imaging agents, published 2008 Dec. 31 (WO 2009/002529 A2).

International PCT Patent Application Publication No. PCT/US2010/028020 to Pomper, M. G., Mease, R. C.; Ray, S., Chen, Y. for PSMA-targeting compounds and uses thereof, published 2010 Sep. 23 (WO2010/108125 A2).

International PCT Patent Application Publication No. PCT/US2008/013158 to Chandran, S. S., Ray, S., Denmeade, S. R., Pomper, M. G., Mease, R. C. for Prostate specific membrane antigen (PSMA) targeted nanoparticles for therapy of prostate cancer, published 2009 Jun. 4 (WO2009/070302 A1).

Aime, S., et al. Curr Pharm Biotechnol 2004, 5, 509-518.

Artemov, D. Molecular magnetic resonance imaging with targeted contrast agents. J. Cell. Biochem. Oct. 15, 2003; 90(3):518-524.

Artemov, D., Mori N., Okollie, B., Bhujwalla, Z. M. Magn Reson Med 2003, 49, 403-408.

Artemov, D., Mori N., Ravi, R., Bhujwalla, Z. M. Cancer Res 2003, 63, 2723-2727.

Babich, J. W., Zimmerman, C., Joyal, J., Lu, G. Radiolabeled prostate specific membrane antigen inhibitors. US 2013/0034494 A1.

Baechler, S., et al. Three-dimensional radiobiological dosimetry of kidneys for treatment planning in peptide receptor radionuclide therapy. Med. Phys. 2012; 39:6118-6128.

Bander, N. H., et al. Phase I trial of $^{177}$lutetium-labeled J591, a monoclonal antibody to prostate-specific membrane antigen, in patients with androgen-independent prostate cancer. J. Clin. Oncol. 2005; 23:4591-4601.

Banerjee, S. R., et al. Synthesis and evaluation of technetium-99m- and rhenium-labeled inhibitors of the prostate-specific membrane antigen (PSMA). J. Med. Chem. 2008; 51:4504-4517.

Banerjee, S. R., Pullambhatla, M., Byun, Y., et al. $^{68}$Ga-labeled inhibitors of prostate-specific membrane antigen (PSMA) for imaging prostate cancer. J. Med. Chem. 2010; 53:5333-5341.

Banerjee, S. R., Pullambhatla, M., Shallal, H., et al. Sequential SPECT and Optical Imaging of Experimental Models of Prostate Cancer with a Dual Modality Inhibitor of the Prostate-Specific Membrane Antigen. *Angew. Chem. Int. Ed. Engl.* Sep. 19, 2011; 50(39):9167-9170.

Banerjee, S. R., et al. A modular strategy to prepare multivalent inhibitors of prostate-specific membrane antigen (PSMA). *Oncotarget.* 2011; 2:1244-1253.

Banergee, S. R., Pullambhatla, M., Foss, C. A., Falk, A., Byun, Y., Nimmagadda, S., Mease, R. C., Pomper, M. G. Effect of chelators on the pharmacokinetics of 99mTc-labeled imaging agents for the prostate-specific membrane antigen (PSMA). *J. Med. Chem.* 2013; 56: 6108-6121.

Banergee, S. R., Pullambhatla, M., Foss, C. A., Nimmagadda, S., Ferdani, R., Anderson, C. J., Mease, R. C., Pomper, M. G. 64Cu-Labeled inhibitors of prostate-specific membrane antigen for PET imaging of prostate cancer. *J. Med. Chem.* 2014; 57: 2657-2669.

Banerjee, S. R., Foss, C. A., Pullambhatla, M., Wang, Y., Srinivasan, S. R. F. K. E. Hobbs, M. Baidoo, R. C. Brechbiel, Mease, G. Sgouros, M. G. Pomper, Preclinical evaluation of $^{86}$Y-labeled inhibitors of prostate specific membrane antigen for dosimetry estimates. *J Nucl Med* 2015.

Baur, B., et al. Synthesis, radiolabelling and in vitro characterization of the Gallium-68-, Yttrium-90- and Lutetium-177-labelled PSMA ligand, CHX-A"-DTPA-DUPA-Pep. *Pharmaceuticals.* 2014; 7:517-529.

Behnam Azad, B., et al. *Nanoscale* 2015, 7, 4432-4442.

Bodei, L., et al. Receptor radionuclide therapy with 90Y-[DOTA]0-Tyr3-octreotide (90Y-DOTATOC) in neuroendocrine tumours. *Eur. J. Nucl. Med. Mol. Imaging.* 2004; 31:1038-1046.

Bolch, W. E., et al., MIRD pamphlet No. 21: a generalized schema for radiopharmaceutical dosimetry—standardization of nomenclature. *J. Nucl. Med.* 2009; 50:477-484.

Boros, E., et al. *J Am Chem Soc* 2012, 134, 19858-19868.

Caravan, P., et al. *Inorg Chem* 2007, 46, 6632-6639.

Caravan, P., et al. *Contrast Media Mol Imaging* 2009, 4, 89-100.

Chandran, S. S., et al., Characterization of a targeted nanoparticle functionalized with a urea-based inhibitor of prostate-specific membrane antigen (PSMA). *Cancer Biol. Therapy.* 2008; 7:974-982.

Chappell, L. L. et al. Synthesis, characterization, and evaluation of a novel bifunctional chelating agent for the lead isotopes 203Pb and 212Pb, Nucl Med Biol, 27 (2000) 93-100.

Chen, Z., Penet, et al. PSMA-targeted theranostic nanoplex for prostate cancer therapy. *ACS Nano.* 2012; 6:7752-7762.

Cheng, Y. and Prusoff, W. H. Relationship between the inhibition constant (K1) and the concentration of inhibitor which causes 50 percent inhibition (I50) of an enzymatic reaction. *Biochem. Pharmacol.* 1973; 22:3099-3108.

Cho, S. Y. et al. Biodistribution, tumor detection, and radiation dosimetry of $^{18}$F-DCFBC, a low-molecular-weight inhibitor of prostate-specific membrane antigen, in patients with metastatic prostate cancer. *J. Nucl. Med.* 2012; 53:1883-1891.

Davis, S. L., et al. Bacterial thymidine kinase as a non-invasive imaging reporter for *Mycobacterium tuberculosis* in live animals. *PloS one* 2009; 4:e6297.

De Leon-Rodriguez, L. M., et al. MRI detection of VEGFR2 in vivo using a low molecular weight peptoid-(Gd)8-dendron for targeting. *J. Am. Chem. Soc.* Sep. 22, 2010; 132(37):12829-12831.

Evans, M. J., et al. *Proc Natl Acad Sci USA* 2011, 108, 9578-9582.

Frenzel, T., et al. *Invest Radiol* 2008, 43, 817-828.

Geninatti-Crich, S. *Contrast Media Mol Imaging* 2011, 6, 421-425.

Ghosh, A. and Heston, W. D. Tumor target prostate specific membrane antigen (PSMA) and its regulation in prostate cancer. *J. Cell. Biochem.* 2004; 91:528-539.

Haffner, M. C., et al. *Hum Pathol* 2009, 40, 1754-1761

Haffner, M. C., et al. *Mod Pathol* 2012, 25, 1079-1085.

Hanaoka, K., et al. *Magn Reson Imaging* 2008, 26, 608-617.

Helisch, A., et al. Pre-therapeutic dosimetry and biodistribution of $^{86}$Y-DOTAPhe1-Tyr3-octreotide versus 111In-pentetreotide in patients with advanced neuroendocrine tumours. *Eur. J. Nucl. Med. Mol. Imaging.* 2004; 31:1386-1392.

Hillier, S. M., et al. *J Nucl Med* 2011, 52, 1087-1093.

Hobbs, R. F., et al. $^{124}$I PET-based 3D-RD dosimetry for a pediatric thyroid cancer patient: real-time treatment planning and methodologic comparison. *J. Nucl. Med.* 2009; 50:1844-1847.

Huang, C. H. and Tsourkas, A. *Curr Top Med Chem* 2013, 13, 411-421.

Kaiser, E., et al. Color test for detection of free terminal amino groups in the solid-phase synthesis of peptides. *Anal Biochem* 1970; 34:595-598.

Kam, B. L., et al. Lutetium-labelled peptides for therapy of neuroendocrine tumours. *Eur. J. Nucl. Med. Mol. Imaging.* 2012; 39 Suppl 1:S103-112.

Konda, et al. *Magma* 2001, 12, 104-113.

Kulkarni, H. M. W., et al. First clinical results with Lu-177 PSMA-TUM1 for the treatment of castrate-resistant metastatic prostate cancer. *J. NUCL. Med.* Meeting Abstract Vol 55; 2014.

Lanza, M., et al. *J Nucl Cardiol* 2004, 11, 733-743.

Low, P. S., Chelvam, V., Kim, Y. PSMA binding linker conjugates and methods for using WO2011/106639, WO 2010/045598 A2, WO 2009/026177A1.

Ma, D., et al. Radioimmunotherapy for model B cell malignancies using $^{90}$Y-labeled anti-CD19 and anti-CD20 monoclonal antibodies. *Leukemia.* 2002; 16:60-66.

Major, J. L. and Meade, T. *J. Acc Chem Res* 2009, 42, 893-903.

Mastarone, D. J., et al. A modular system for the synthesis of multiplexed magnetic resonance probes. *J Am Chem Soc.* Apr. 13, 2011; 133(14):5329-5337.

McDevitt, M. R. Radioimmunotherapy with alpha-emitting nuclides, *Eur J Nucl Med,* 25 (1998) 1341-1351.

Mease, R. C., et al. PET imaging in prostate cancer: focus on prostate-specific membrane antigen. *Curr. Top. Med. Chem.* 2013; 13:951-962.

Milowsky, M. I., et al. Vascular targeted therapy with anti-prostatespecific membrane antigen monoclonal antibody J591 in advanced solid tumors. *J. Clin. Oncol.* 2007; 25:540-547.

Nayak, T. K. and Brechbiel, M. W. $^{86}$Y based PET radiopharmaceuticals: radiochemistry and biological applications. *Med. Chem.* 2011; 7:380-388.

Olson, W. C., et al. Clinical trials of cancer therapies targeting prostate specific membrane antigen. *Rev. Recent Clin. Trials.* 2007; 2:182-190.

Olszewski, R. T., et al. NAAG peptidase inhibition reduces locomotor activity and some stereotypes in the PCP model of schizophrenia via group II mGluR. *J. Neurochem.* 2004; 89:876-885.

Palm, S., et al. Pharmacokinetics and biodistribution of (86)Ytrastuzumab for (90)Y dosimetry in an ovarian carcinoma model: correlative MicroPET and MRI. *J. Nucl. Med.* 2003; 44:1148-1155.

Pomper, M. G., Ray, S., Mease, R. C., Foss, C. Labeled inhibitors of prostate specific membrane antigen (PSMA), biological evaluation, and use as imaging agents. WO 2009/002529 A2.

Rooney, W. D., et al. *Magn Reson Med* 2007, 57, 308-318.

Schulke, N., et al. The homodimer of prostate-specific membrane antigen is a functional target for cancer therapy. *Proc. Natl. Acad. Sci. USA.* 2003; 100:12590-12595.

Schwartz, J., et al. Renal uptake of bismuth-213 and its contribution to kidney radiation dose following administration of actinium-225-labeled antibody. *Phys. Med. Biol.* 2011; 56:721-733.

Silver, D. A., et al. Prostate-specific membrane antigen expression in normal and malignant human tissues. *Clin. Cancer Res.* 1997; 3:81-85.

Song, Y., et al. *J Am Chem Soc* 2008, 130, 6662-6663.

Stabin, M. G., et al. OLINDA/EXM: the second-generation personal computer software for internal dose assessment in nuclear medicine. *J. Nucl. Med.* 2005; 46:1023-1027.

Tagawa, S. T., et al. Bone marrow recovery and subsequent chemotherapy following radiolabeled anti-prostate-specific membrane antigen monoclonal antibody j591 in men with metastatic castration-resistant prostate cancer. *Front. Oncol.* 2013; 3:1-6.

Tagawa, S. T., et al. Phase II study of Lutetium-177-labeled anti-prostate specific membrane antigen monoclonal antibody J591 for metastatic castration-resistant prostate cancer. *Clin. Cancer Res.* 2013; 19:5182-5191.

Tse, B. W., et al. *Nanomedicine* 2015, 10, 375-386.

Vallabhajosula, S., et al. Pharmacokinetics and biodistribution of $^{111}$In- and $^{177}$Lu-labeled J591 antibody specific for prostate-specific membrane antigen: prediction of $^{90}$YJ591 radiation dosimetry based on $^{111}$In or $^{177}$Lu? *J. Nucl. Med.* 2005; 46:634-641.

Witzig, T. E., et al. Safety of yttrium-90 ibritumomab tiuxetan radioimmunotherapy for relapsed low-grade, follicular, or transformed non-Hodgkin's lymphoma. *J. Clin. Oncol.* 2003; 21:1263-1270.

Woodard, H. Q., et al. Letter: Expression of tissue isotope distribution. *J. Nucl. Med.* 1975; 16:958-959.

Wu, X. et al. *Bioconjug Chem* 2012; 23, 1548-1556.

Yong, K. and Brechbiel, M. W. Towards translation of 212Pb as a clinical therapeutic; getting the lead in!, Dalton Trans, 40 (2011) 6068-6076.

Yong, K. J. et al. (212)Pb-radioimmunotherapy induces G(2) cell-cycle arrest and delays DNA damage repair in tumor xenografts in a model for disseminated intraperitoneal disease, Mol. Cancer Ther., 11 (2012) 639-648.

Yong, K. J. et al. 212Pb-radioimmunotherapy potentiates paclitaxel-induced cell killing efficacy by perturbing the mitotic spindle checkpoint, Br. J. Cancer, 108 (2013) 2013-2020.

Yoo, J., et al. Preparation of high specific activity (86)Y using a small biomedical cyclotron. *Nucl. Med. Biol.* 2005; 32:891-897.

Zechmann, C. M., et al. Radiation dosimetry and first therapy results with a (124)I/(131)I-labeled small molecule (MIP-1095) targeting PSMA for prostate cancer therapy. *Eur. J. Nucl. Med. Mol. Imaging.* 2014; 41:1280-292.

Although the foregoing subject matter has been described in some detail by way of illustration and example for purposes of clarity of understanding, it will be understood by those skilled in the art that certain changes and modifications can be practiced within the scope of the appended claims.

That which is claimed:

1. A compound of formula (I):

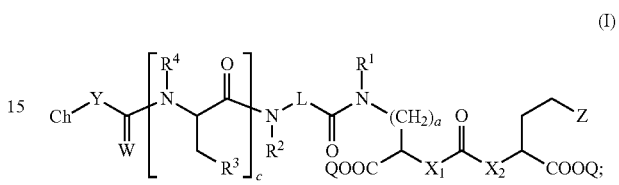

Z is tetrazole or $CO_2Q$;

Q is H or a protecting group;

$X_1$ and $X_2$ are each independently NH or O;

a is an integer selected from the group consisting of 1, 2, 3 and 4;

c is an integer selected from the group consisting of 0, 1, 2, 3 and 4;

each $R^1$, $R^2$ and $R^4$ is independently H or $C_1$-$C_4$ alkyl;

each $R^3$ is independently H, $C_1$-$C_6$ alkyl or $C_2$-$C_{12}$ aryl;

W is independently O or S;

Y is —NH— and can be present or absent;

L is a linker selected from the group consisting of:

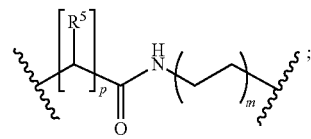

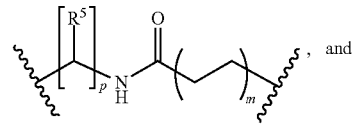

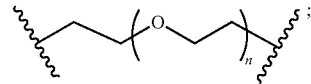

wherein:

m is an integer selected from the group consisting of 1, 2, 3, 4, 5, 6, 7 and 8;

each $R^5$ is independently H or —COOR$^6$ wherein each $R^6$ is independently H or a $C_1$-$C_6$ alkyl;

n is an integer selected from the group consisting of 1, 2, 3, 4, 5, 6, 7, 8, 9, 10, 11 and 12;

p is an integer selected from the group consisting of 1, 2, 3, 4, 5, 6, 7 and 8;

Ch is a chelating moiety that can comprise one or more metals or radiometals, wherein the chelating moiety is selected from the group consisting of:

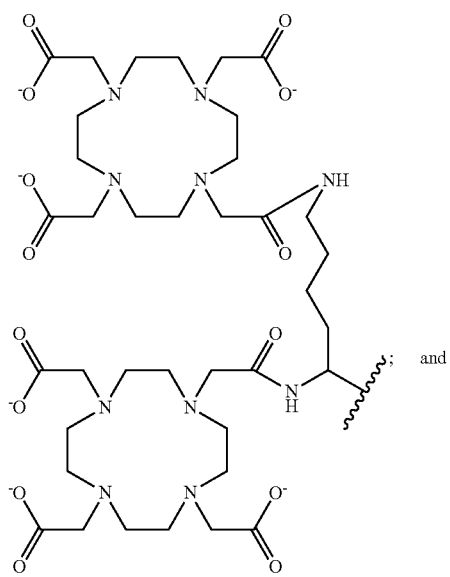

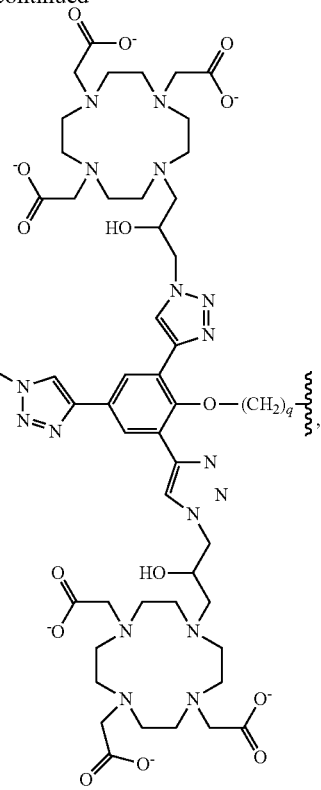

wherein q is an integer selected from the group consisting of 1, 2, 3, 4, 5, 6, 7, and 8;

or a pharmaceutically acceptable salt thereof.

2. The compound of Formula (I), wherein the compound is selected from the group consisting of:

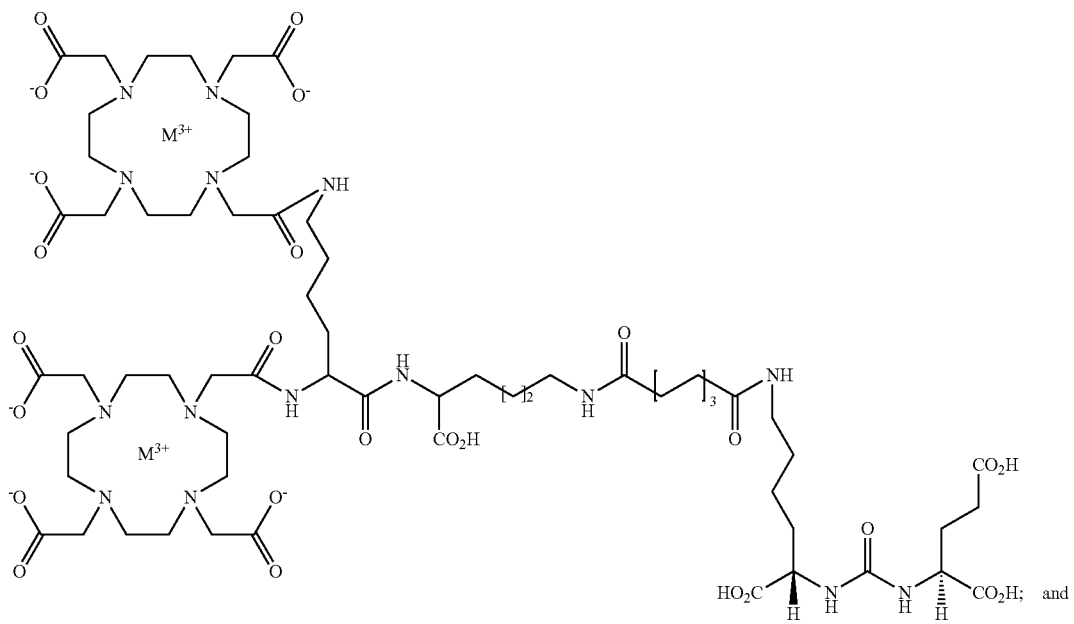

-continued

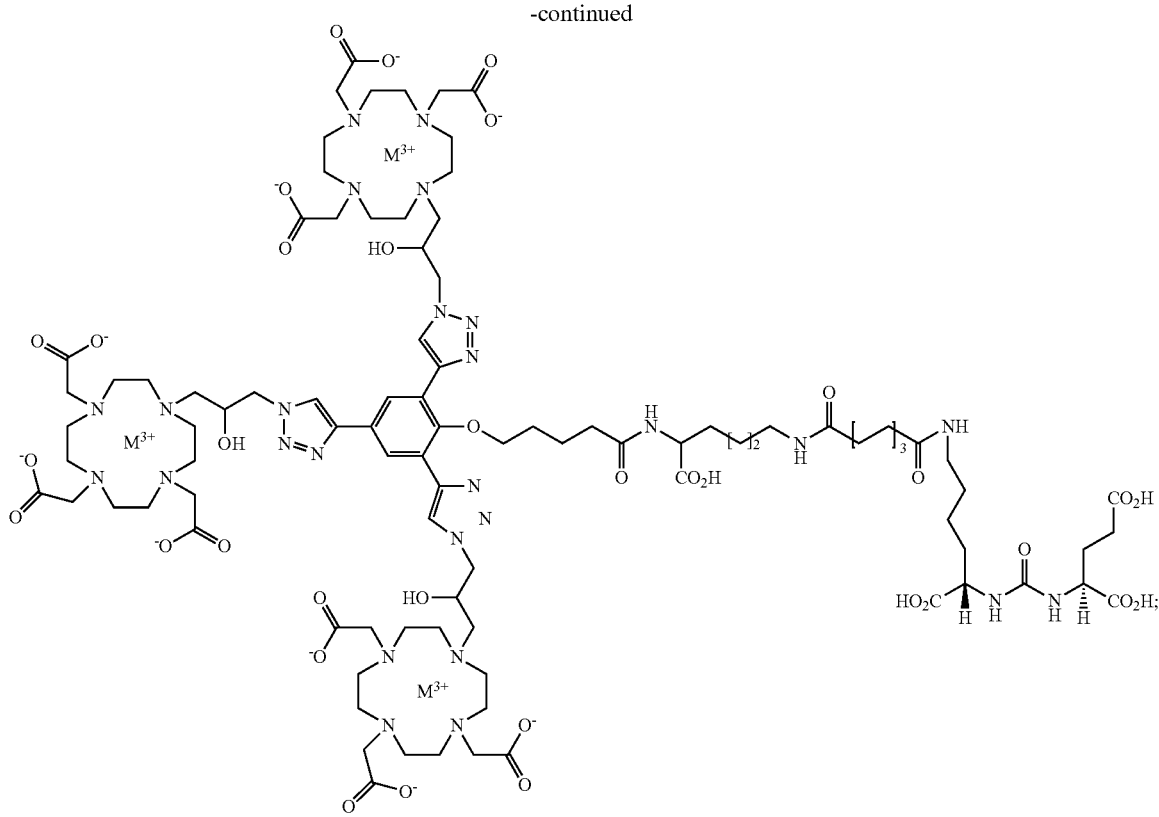

wherein:
M is a metal or a radiometal; or
a pharmaceutically acceptable salt thereof.

3. The compound of claim 1 wherein the metal is selected from the group consisting of Gd, Lu, Ac, Bi, Pb, Cu, In, Sc, and Y.

4. The compound of claim 1, wherein the nonradioactive metal is Gd-157 (stable isotope).

5. The compound of claim 1, wherein the radiometal is selected from the group consisting of Lu-177, Ac-225, Bi-213, Bi-212, Pb-212, Cu-67, In-111, Sc-47, and Y-90.

6. The compound of claim 1, wherein the radiometal is selected from the group consisting of Y-86 and Sc-44.

7. The compound of claim 1, wherein the radiometal is selected from the group consisting of Lu-177 and In-111.

8. A method for imaging or treating one or more prostate-specific membrane antigen (PSMA) tumors or cells, the method comprising contacting the one or more tumors or cells with an effective amount of a compound of formula (I) and making an image, the compound of formula (I) comprising:

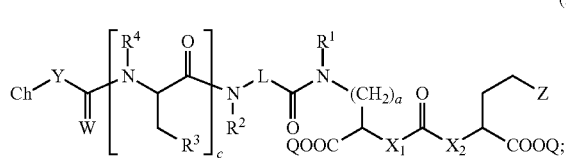

(I)

Z is tetrazole or $CO_2Q$;
Q is H or a protecting group;

$X_1$ and $X_2$ are each independently NH or O;
a is an integer selected from the group consisting of 1, 2, 3 and 4;
c is an integer selected from the group consisting of 0, 1, 2, 3 and 4;
each $R^1$, $R^2$ and $R^4$ is independently H or $C_1$-$C_4$ alkyl;
each $R^3$ is independently H, $C_1$-$C_6$ alkyl or $C_2$-$C_{12}$ aryl;
W is independently O or S;
Y is —NH— and can be present or absent;
L is a linker, wherein the linker is selected from the group consisting of:

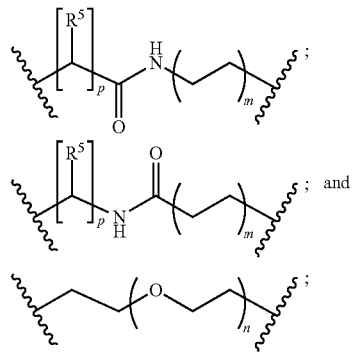

wherein:
m is an integer selected from the group consisting of 1, 2, 3, 4, 5, 6, 7 and 8;
each $R^5$ is independently H or —$COOR^6$ wherein each $R^6$ is independently H or a $C_1$-$C_6$ alkyl;

n is an integer selected from the group consisting of 1, 2, 3, 4, 5, 6, 7, 8, 9, 10, 11, and 12; p is an integer selected from the group consisting of 1, 2, 3, 4, 5, 6, 7 and 8;

Ch is a chelating moiety which comprises one or more metals or radiometals, wherein the chelating moiety is selected from the group consisting of:

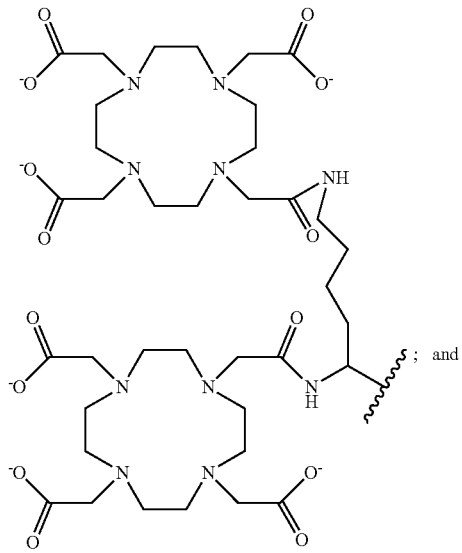
; and

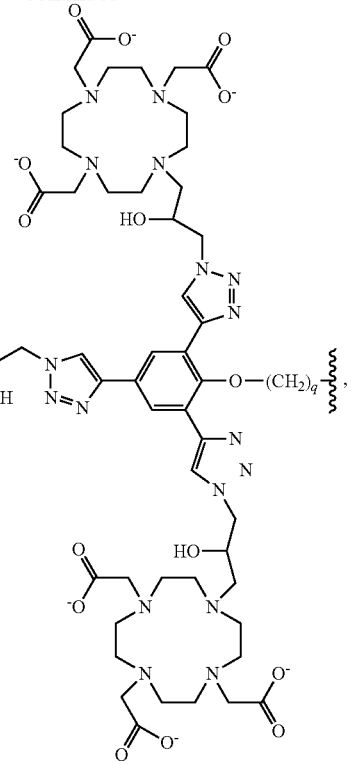

wherein q is an integer selected from the group consisting of 1, 2, 3, 4, 5, 6, 7, and 8; or a pharmaceutically acceptable salt thereof.

9. The method of claim 8, wherein the compound is selected from the group consisting of:

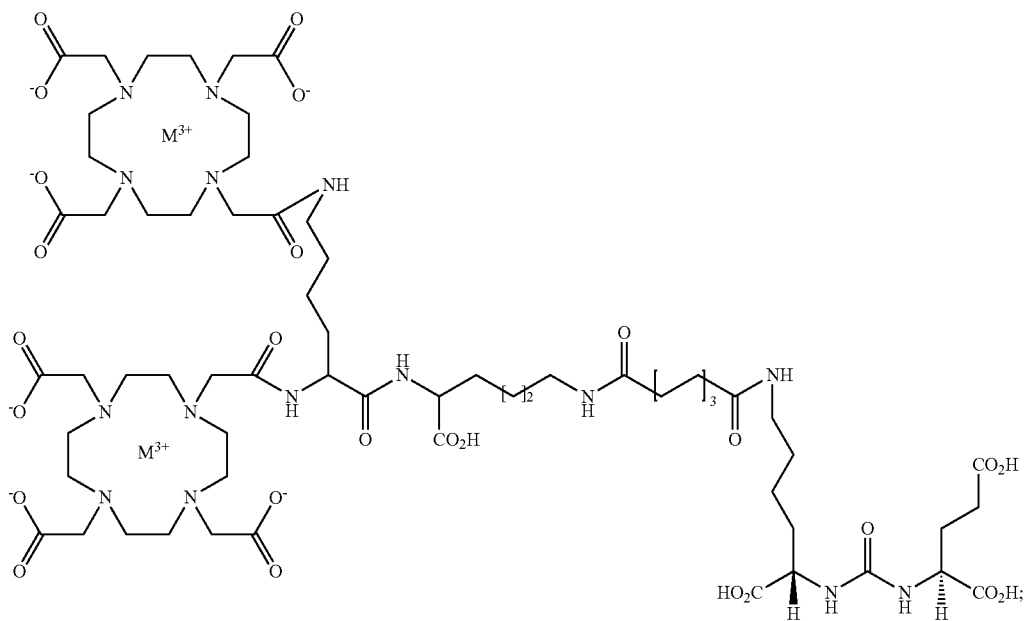

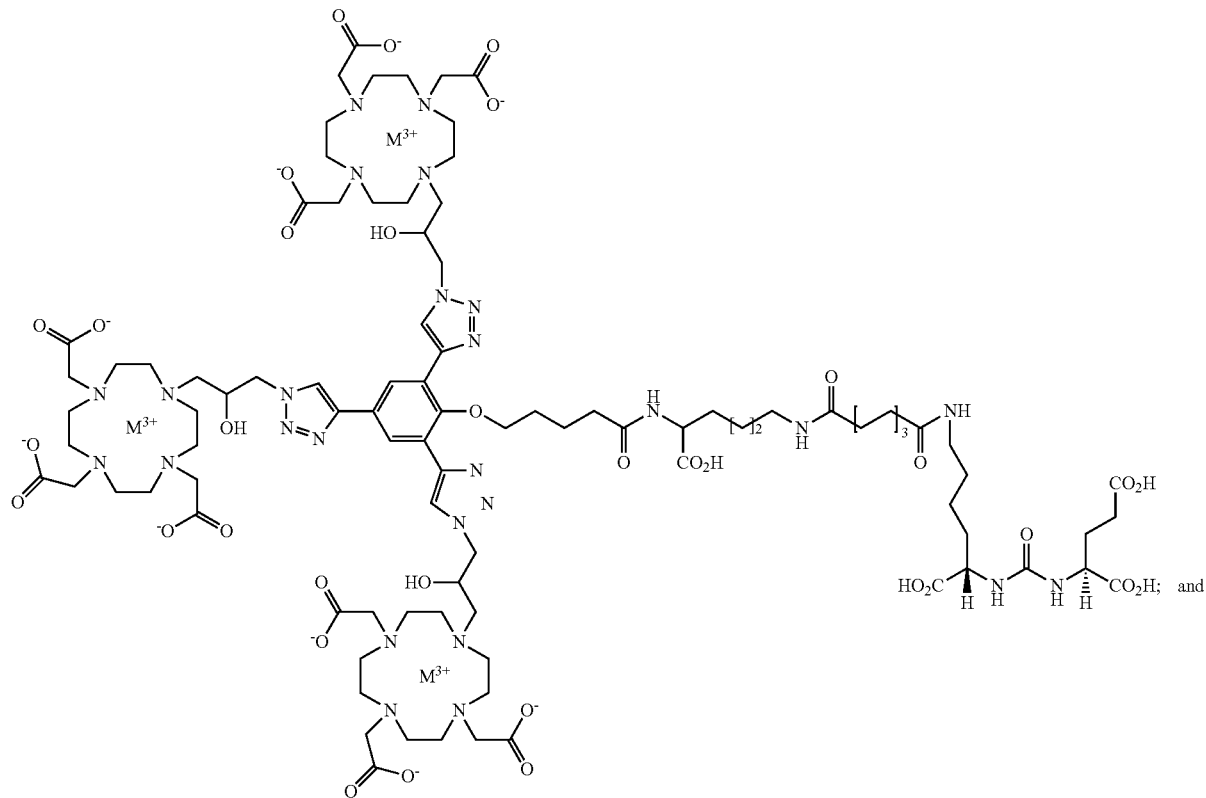

wherein:

M is a metal or a radiometal; or a pharmaceutically acceptable salt thereof.

10. The method of claim 8, wherein the metal is selected from the group consisting of Gd, Lu, Ac, Bi, Pb, Cu, In, Sc and Y.

11. The method of claim 8, wherein imaging comprises magnetic resonance imaging (MM) and the nonradioactive metal is Gd-157 (stable isotope).

12. The method of claim 8, wherein the method comprises treating one or more prostate-specific membrane antigen (PSMA) tumors or cells and the radiometal is selected from the group consisting of Lu-177, Ac-225, Bi-212, Bi-213, Pb-212, Cu-67, In-111, Sc-47, and Y-90.

13. The method of claim 8, wherein the imaging comprises positron emission tomography (PET) imaging and the radiometal is selected from the group consisting of Y-86 and Sc-44.

14. The method of claim 8, wherein the imaging comprises single-photon emission computed tomography (SPECT) imaging and the radiometal is selected from the group consisting of Lu-177 and In-111.

15. The method of claim 8, wherein the one or more PSMA-expressing tumors or cells is selected from the group consisting of: a prostate tumor or cell, a metastasized prostate tumor or cell, a lung tumor or cell, a renal tumor or cell, a glioblastoma, a pancreatic tumor or cell, a bladder tumor or cell, a sarcoma, a melanoma, a breast tumor or cell, a colon tumor or cell, a germ cell, a pheochromocytoma, an esophageal tumor or cell, a stomach tumor or cell, and combinations thereof.

16. The method of claim 8, wherein the one or more PSMA-expressing tumors or cells is a prostate tumor or cell.

17. The method of claim 8, wherein the one or more PSMA-expressing tumors or cells is in vitro, in vivo, or ex vivo.

18. The method of claim 8, wherein the one or more PSMA-expressing tumors or cells is present in a subject.

19. The method of claim 18, wherein the compound comprising the imaging agent is cleared from the tumor or cell in the subject.

20. The method of claim 18, wherein the compound comprising the imaging agent is selected from the group consisting of:

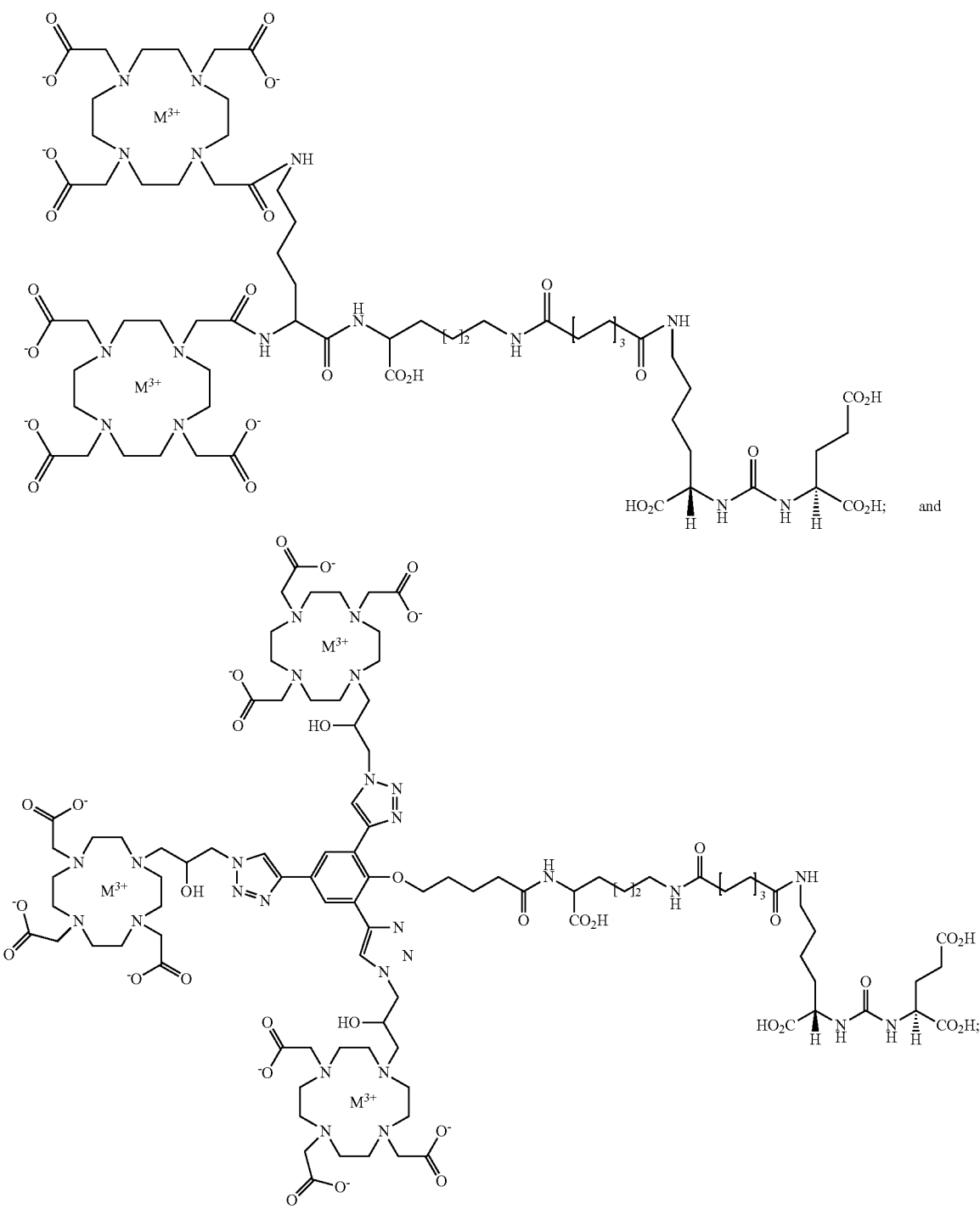
wherein M is a metal or a radiometal; or
a pharmaceutically acceptable salt thereof;
and is cleared more rapidly from a subject's kidneys than from a tumor of the subject.
* * * * *